US012644001B2

(12) United States Patent
Mao et al.

(10) Patent No.: US 12,644,001 B2
(45) Date of Patent: Jun. 2, 2026

(54) FLUORENYL CYANINE DYES

(71) Applicant: Biotium, Inc., Fremont, CA (US)

(72) Inventors: Fei Mao, Fremont, CA (US); Wai-Yee Leung, San Ramon, CA (US); Patrick Mcgarraugh, San Francisco, CA (US)

(73) Assignee: Biotium, Inc., Fremont, CA (US)

( * ) Notice: Subject to any disclaimer, the term of this patent is extended or adjusted under 35 U.S.C. 154(b) by 742 days.

(21) Appl. No.: 18/011,149

(22) PCT Filed: Jun. 7, 2021

(86) PCT No.: PCT/US2021/036201

§ 371 (c)(1),
(2) Date: Dec. 16, 2022

(87) PCT Pub. No.: WO2021/252368

PCT Pub. Date: Dec. 16, 2021

(65) Prior Publication Data

US 2023/0257587 A1 Aug. 17, 2023

Related U.S. Application Data

(60) Provisional application No. 63/036,131, filed on Jun. 8, 2020.

(51) Int. Cl.

*C07D 209/70* (2006.01)
*C09B 23/06* (2006.01)
*C09B 23/08* (2006.01)
*C09B 23/10* (2006.01)

(52) U.S. Cl.

CPC .......... *C09B 23/102* (2013.01); *C07D 209/70* (2013.01); *C09B 23/06* (2013.01); *C09B 23/083* (2013.01)

(58) Field of Classification Search

CPC .... C07D 209/70; C09B 23/102; C09B 23/083
See application file for complete search history.

(56) References Cited

U.S. PATENT DOCUMENTS

| | | | |
|---|---|---|---|
| 4,520,110 | A | 5/1985 | Stryer et al. |
| 4,683,195 | A | 7/1987 | Mullis et al. |
| 4,683,202 | A | 7/1987 | Mullis |
| 4,711,955 | A | 12/1987 | Ward et al. |
| 4,889,818 | A | 12/1989 | Gelfand et al. |
| 5,047,519 | A | 9/1991 | Hobbs, Jr. et al. |
| 5,234,903 | A | 8/1993 | Nho et al. |
| 5,298,643 | A | 3/1994 | Greenwald |
| 5,321,095 | A | 6/1994 | Greenwald |
| 5,324,844 | A | 6/1994 | Zalipsky |
| 5,338,671 | A | 8/1994 | Scalice et al. |
| 5,349,001 | A | 9/1994 | Greenwald et al. |
| 5,405,877 | A | 4/1995 | Greenwald et al. |
| 5,478,805 | A | 12/1995 | Shorr et al. |
| 5,494,810 | A | 2/1996 | Barany et al. |
| 5,567,422 | A | 10/1996 | Greenwald |
| 5,605,976 | A | 2/1997 | Martinez et al. |
| 5,612,460 | A | 3/1997 | Zalipsky |
| 5,637,749 | A | 6/1997 | Greenwald |
| 5,650,388 | A | 7/1997 | Shorr et al. |
| 5,681,567 | A | 10/1997 | Martinez et al. |
| 5,686,110 | A | 11/1997 | Greenwald et al. |
| 5,714,327 | A | 2/1998 | Houthoff et al. |
| 5,714,386 | A | 2/1998 | Roederer |
| 5,756,593 | A | 5/1998 | Martinez et al. |
| 5,773,258 | A | 6/1998 | Birch et al. |
| 5,808,096 | A | 9/1998 | Zalipsky |
| 5,824,477 | A | 10/1998 | Stanley |
| 5,871,928 | A | 2/1999 | Fodor et al. |
| 5,880,131 | A | 3/1999 | Greenwald et al. |
| 5,981,747 | A | 11/1999 | Mujumdar et al. |
| 5,986,093 | A | 11/1999 | Mujumdar et al. |
| 6,013,283 | A | 1/2000 | Greenwald et al. |
| 6,033,850 | A | 3/2000 | Purvis |
| 6,040,193 | A | 3/2000 | Winkler et al. |
| 6,207,464 | B1 | 3/2001 | Karandikar et al. |
| 6,251,382 | B1 | 6/2001 | Greenwald et al. |
| 6,262,776 | B1 | 7/2001 | Griffits |
| 6,277,984 | B1 | 8/2001 | Mujumdar et al. |
| 6,403,320 | B1 | 6/2002 | Read et al. |
| 6,479,303 | B1 | 11/2002 | Waggoner et al. |

(Continued)

FOREIGN PATENT DOCUMENTS

| | | | |
|---|---|---|---|
| WO | WO-0013026 | A1 | 3/2000 |
| WO | WO-2006081249 | A2 | 8/2006 |
| WO | WO-2021252368 | A1 | 12/2021 |

OTHER PUBLICATIONS

Balakrishnan et al.: Chemical modification of poly(vinyl chloride) resin using poly(ethylene glycol) to improve blood compatibility. Biomaterials. 26(17):3495-3502. doi:10.1016/j.biomaterials.2004.09.032 (2005).
Browne et al.: Emerging Technologies. BioProbes. 52:2-11 (2007).
Chatterjee et al.: Cloning and overexpression of the gene encoding bacteriophage T5 DNA polymerase. Gene 97: 13-19 (1991).
Davey et al.: Flow cytometry and cell sorting of heterogeneous microbial populations: the importance of single-cell analyses. Microbiol Rev. 60(4):641-696. doi:10.1128/mr.60.4.641-696.1996 (1996).
De Mesmaeker, et al. Backbone modifications for antisense oligonucleotides. Pure & Appl. Chem. 1997;69(3):437-440.

(Continued)

*Primary Examiner* — Shawquia Jackson

(74) *Attorney, Agent, or Firm* — WILSON SONSINI GOODRICH & ROSATI

(57) ABSTRACT

The present invention relates to fluorescent dyes in general. The present invention provides a wide range of fluorescent dyes and kits containing the same, which are applicable for labeling a variety of biomolecules, cells and microorganisms. The present invention also provides various methods of using the fluorescent dyes for research and development, forensic identification, environmental studies, diagnosis, prognosis, and/or treatment of disease conditions.

47 Claims, 10 Drawing Sheets

(56) References Cited

U.S. PATENT DOCUMENTS

| | | | |
|---|---|---|---|
| 6,576,424 B2 | 6/2003 | Fodor et al. |
| 6,824,782 B2 | 11/2004 | Whitlow et al. |
| 6,917,726 B2 | 7/2005 | Levene et al. |
| 6,974,873 B2 | 12/2005 | Leung et al. |
| 7,013,054 B2 | 3/2006 | Levene et al. |
| 7,161,010 B2 | 1/2007 | Kobayashi et al. |
| 7,170,050 B2 | 1/2007 | Turner et al. |
| 7,181,122 B1 | 2/2007 | Levene et al. |
| 7,267,673 B2 | 9/2007 | Pilcher et al. |
| 7,292,742 B2 | 11/2007 | Levene et al. |
| 7,465,810 B2 | 12/2008 | Divu et al. |
| 2006/0019274 A1 | 1/2006 | Goel |
| 2015/0185182 A1 | 7/2015 | Mao et al. |

OTHER PUBLICATIONS

Herzenberg et al.: The history and future of the fluorescence activated cell sorter and flow cytometry: a view from Stanford. Clin Chem. 48(10):1819-1827. PMID: 12324512 (2002).

Jacobsen et al.: The N-terminal amino-acid sequences of DNA polymerase I from *Escherichia coli* and of the large and the small fragments obtained by a limited proteolysis. Eur. J Biochem. 45: 623-627 (1974).

Jung et al. Bacteriophage PRD1 DNA polymerase: evolution of DNA polymerases. PNAS USA 84:8287-8291 (1987).

Kaboord et al.: Accessory proteins function as matchmakers in the assembly of the T4 DNA polymerase holoenzyme. Curr Biol. 5: 149-157 (1995).

Matsumoto, et al. Primary structure of bacteriophage M2 DNA polymerase: conserved segments within protein-priming DNA polymerases and DNA polymerase I of *Escherichia coli*. Gene. Dec. 14, 1989;84(2):247-55.

Mehvar R. Modulation of the pharmacokinetics and pharmacodynamics of proteins by polyethylene glycol conjugation. J. Pharm Pharm Sci. 2000;3(1):125-136.

PCT/US2021/036201 International Search Report and Written Opinion dated Oct. 22, 2021.

Pubchem, SID 316095774 (2019).

Rigler, et al. Differences in the mechanism of stimulation of T7 DNA polymerase by two binding modes of *Escherichia coli* single-stranded DNA-binding protein. J. Biol. Chem. 1995;;270(15):8910-9.

Siegal et al.: A novel DNA helicase from calf thymus. J Biol Chem. 267(19): 13629-13635 (1992).

Skaliter, et al. Rolling circle DNA replication in vitro by a complex of herpes simplex virus type 1-encoded enzymes. Proc. Natl, Acad. Sci. USA. 1994;91(22):10665-9.

Stewart: Lucifer dyes—highly fluorescent dyes for biological tracing. Nature. 292(5818):17-21. doi: 10.1038/292017a0 (1981).

Tsurumi, et al. Functional interaction between Epstein-Barr virus DNA polymerase catalytic subunit and its accessory subunit in vitro. J. Virology. 1993;67(12):7648-53.

Veiseh, et al. Tumor paint: a chlorotoxin:Cy5.5 bioconjugate for intraoperative visualization of cancer foci. Cancer Res. Jul. 15, 2007;67(14):6882-8.

Wang et al.: Eukaryotic elongation factor 2 kinase activity is controlled by multiple inputs from oncogenic signaling. Mol Cell Biol. 34(22):4088-4103. doi:10.1128/MCB.01035-14 (2014).

Zhu, et al. Purification and characterization of PRD1 DNA polymerase. Biochim Biophys Acta. Oct. 18, 1994;1219(2):267-76.

Zijderveld, et al. Helix-destabilizing properties of the adenovirus DNA-binding protein. J. Virology. 1994;68(2):1158-64.

CF700 GAM, DOL 6.4

CF700 GAM, DOL 3.1

FLUORENYL CYANINE DYES

CROSS REFERENCE TO RELATED APPLICATIONS

This application was filed pursuant to 35 U.S.C. § 371 as a United States National Phase Application of International Application No. PCT/US2021/036201, filed on Jun. 7, 2021, which claims the benefit of U.S. Provisional Patent Application No. 63/036,131, filed Jun. 8, 2020, each of which is incorporated in its entirety by reference in the disclosure of this application.

BACKGROUND OF THE INVENTION

Fluorescent dyes are widely used in biological research and medical diagnostics. Fluorescent dyes are superior to conventional radioactive materials because fluorescent dyes are less expensive and less toxic, and can typically be detected with sufficient sensitivity. Further, the availability of a diversity of fluorophores with distinguishable color ranges has made it more practical to perform multiplexed assays capable of detecting several biological targets at the same time. The ability to visualize multiple targets in parallel is often required for delineating the spatial and temporal relationships amongst different biological targets in vitro and in vivo. Techniques such as spectrum imaging and spectrum flow cytometry are able to resolve even more optical signals than traditional wavelength band-based detection methods by advanced deconvolution of spectral shapes and peak positions. Because infra-red radiation can penetrate deeper into living tissues than visible light, fluorescent dyes are used in vivo if their characteristic wavelengths are sufficiently long. Dyes that absorb or emit in the infra-red region also generally provide superior signal to noise ratio because the background fluorescence associated with biological samples is usually stronger in the visible spectrum. Generally, the availability of a wide range of fluorescent dyes has opened a new avenue for conducting high-throughput and automated assays, thus dramatically reducing the unit cost per assay. Moreover, the low toxicity of fluorescent dyes provides ease of handling in vitro and enables imaging biological activities in vivo.

SUMMARY OF THE INVENTION

Further improvements in the properties of the dyes are needed in order to meet the increasing demands of new instruments and new biological applications. Specifically, additional strategies are necessary to allow fine-tuning of the wavelengths of the dyes for maximal signal detection and for providing additional colors and spectral shapes currently unattainable using known synthetic methods. Moreover, it is desirable to provide new dyes that offer a combination of optimal wavelengths for instrument compatibility and improved brightness, photostability and water-solubility for labeling biomolecules. The present invention addresses this need and provides additional advantages.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
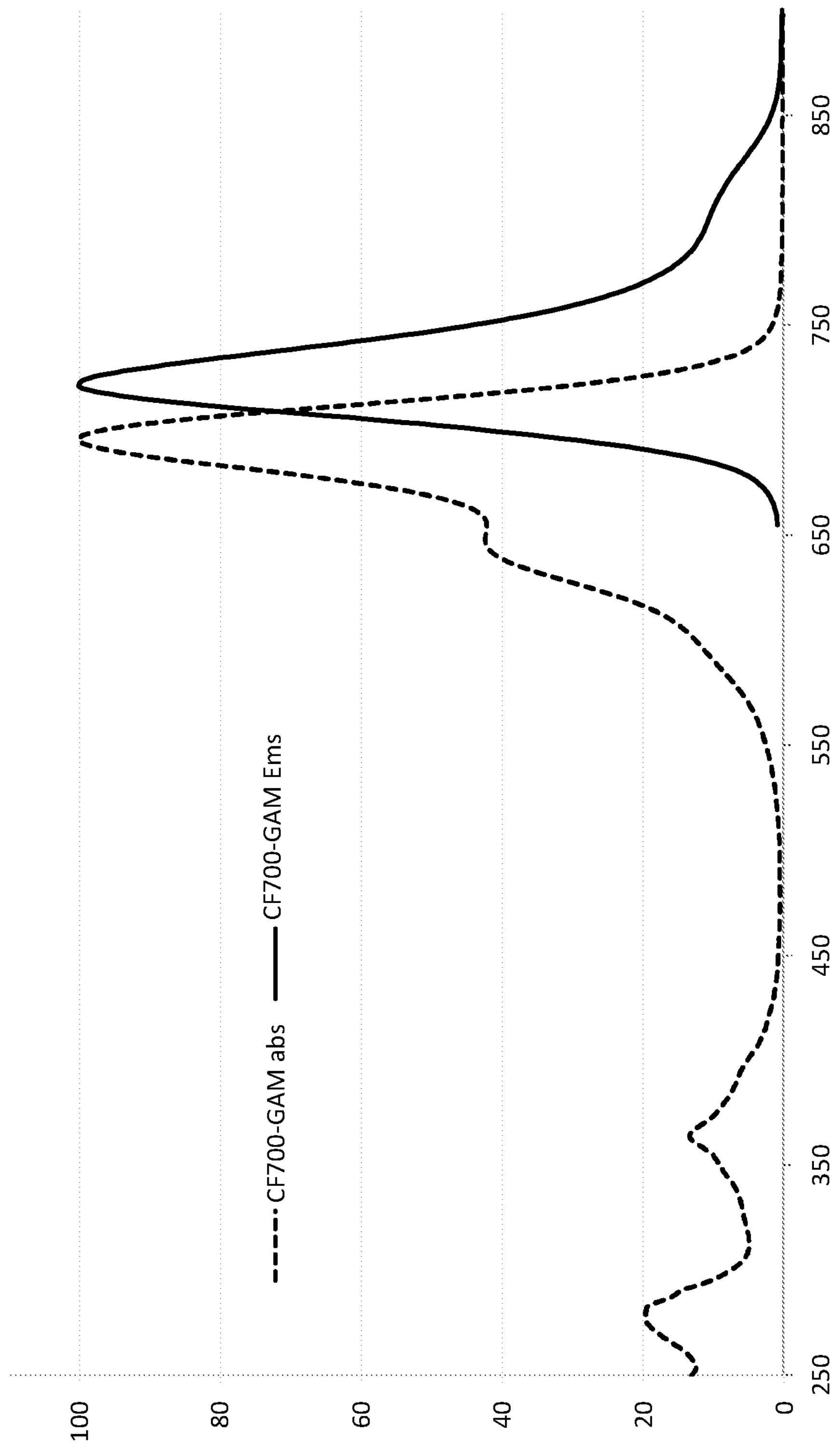
FIG. 1 shows absorption (dashed line) and emission (solid line) spectra of a compound of the invention conjugated to goat anti-mouse IgG.

The present invention discloses novel cyanine dyes which may be used for any application, including the labeling of molecules and biomolecules such as polypeptides, polynucleotides and/or metal chelators and are also suitable for use in a wide range of other applications, including diagnostic and imaging systems. In some aspect of the invention, the dyes are used for labeling proteins, such as primary or secondary antibodies in biological detection schemes such as flow cytometry or microscopy.

Definitions

The compounds of the present invention may have asymmetric centers, chiral axes, and chiral planes (as described in: E. L. Eliel and S. H. Wilen, Stereo-chemistry of Carbon Compounds, John Wiley & Sons, New York, 1994, pages 1119 1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted.

When any variable (e.g. $R_x$, L, Q) occurs more than one time in any constituent, its definition on each occurrence is independent at every other occurrence. Combinations of substituents and variables are permissible when such combinations result in stable compounds. Lines drawn into the ring systems from substituents indicate that the indicated bond may be attached to any of the substitutable ring carbon or nitrogen atoms or a ring nitrogen that can be quarternized. If the ring system is polycyclic, it is intended that the bond be attached to any of the suitable carbon or nitrogen atoms on the proximal ring only. Substitution of a ring by a substitutent generally allows the substituent to be a cyclic structure fused to the ring.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, "alkyl" is intended to include both branched, straight-chain, and cyclic saturated aliphatic hydrocarbon groups. Alkyl groups specifically include methyl, ethyl, propyl, butyl, pentyl, hexyl, heptyl, octyl, nonyl, decyl, and so on, as well as cycloalkyls such as cyclopropyl, cyclobutyl, cyclopentyl, cyclohexyl, tetrahydronaphthalene, methylenecylohexyl, and so on. For example, an alkyl chain designated as $C_1$-$C_{20}$ may have from 1 to 20 carbon atoms. "Alkoxy" represents an alkyl group attached through an oxygen bridge.

The term "alkenyl" refers to a non-aromatic hydrocarbon group, straight, branched or cyclic, containing at least one carbon to carbon double bond. Alkenyl groups include, but are not limited to, ethenyl, propenyl, butenyl and cyclohexenyl. For example, an alkenyl chain designated as $C_2$-$C_{20}$ may have from 2 to 20 carbon atoms. The straight, branched or cyclic portion of the alkenyl group may contain double bonds and may be substituted if a substituted alkenyl group is indicated.

The term "alkynyl" refers to a hydrocarbon group, straight, branched or cyclic, containing at least one carbon to carbon triple bond. Alkynyl groups include, but are not limited to, ethynyl, propynyl and butynyl. For example, an alkynyl chain designated as $C_2$-$C_{20}$ may have from 2 to 20 carbon atoms. The straight, branched or cyclic portion of the alkynyl group may contain triple bonds and may be substituted if a substituted alkynyl group is indicated.

As used herein, "aryl" is intended to mean any stable monocyclic or polycyclic carbon ring of up to 7 atoms in each ring, wherein at least one ring is aromatic. Examples of such aryl elements include phenyl, naphthyl, tetrahydronaphthyl, indanyl, biphenyl, phenanthryl, anthryl or acenaphthyl. For example, an aryl group may be a 6-carbon monocyclic or 10-carbon bicyclic aromatic ring system wherein 0, 1, 2, 3, or 4 atoms of each ring may be substituted by a substituent. In cases where the aryl substituent is bicyclic and one ring is non-aromatic, it is understood that attachment is via the aromatic ring.

The term "heteroaryl", as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to imidazolyl, benzimidazolyl, acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, tetrahydroquinoline, xanthenyl, and coumarinyl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing at least one heteroatom which is O, N or S. This definition includes bicyclic groups. "Heterocyclyl" therefore includes the above mentioned heteroaryls, as well as dihydro and tetrahydro analogs thereof. Further examples of "heterocyclyl" include, but are not limited to the following: benzimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

The alkyl, alkenyl, alkynyl, cycloalkyl, aryl, heteroaryl and heterocyclyl substituents may be unsubstituted or unsubstituted, unless specifically defined otherwise. For example, an alkyl group may be substituted with one or more substituents selected from OH, oxo, halo, alkoxy, dialkylamino, $-PO_3^-$, $-SO_3^{2-}$, $-CO_2^-$, a reactive group, or heterocyclyl, such as morpholinyl or piperidinyl.

The terms "halo" and "halogen" are intended to include chloro, fluoro, bromo and iodo groups.

The term "aromatic" is used in its usual sense, including unsaturation that is essentially delocalized across multiple bonds, such as around a ring.

The term "substituent" refers to an atom, radical or chemical group which replaces a hydrogen in a substituted chemical group, radical, molecule, moiety or compound. In some cases, "substituent" may refer to an atom, radical or chemical group which replaces a lone-pair electron on a nitrogen. In such cases, the substituent may alternatively be referred to as a quarternizing group or quarternizing substituent.

Unless otherwise stated, the term "radical", as applied to any molecule or compound, is used to refer to a part, fragment or group of the molecule or compound rather than to a "free radical". A radical may be linked to another moiety through a covalent bond.

The term "reactive group" refers to a chemical moiety capable of reacting with a reaction partner on a substrate or substrate molecule to form a covalent bond. A compound of the invention can be used to label a wide variety of molecules or substrates that contain a suitable reaction partner or are derivatized to contain a suitable reaction partner. "Reactive group" and "reaction partner" may refer to groups on a compound of the present invention, or to groups on a molecule to be labeled. Here, by way of convenience, but not limitation, a bond-forming group on a compound will generally be referred to as a reactive group and a bond-forming group on the substrate molecule will generally be referred to as a reaction partner. "Reaction substrate", "substrate" and "reaction partner" are used interchangeably throughout this document.

The term "biopolymer" refers to a biological substance having a molecular weight of greater than 1000 daltons and capable of forming a conjugate with dyes of the invention. Suitable biopolymers include proteins, carbohydrates (including polysaccharides), nucleic acids, lipids (including phospholipids), microparticles such as vesicles (e.g. liposomes), polymeric microparticles, animal or plant cells, bacteria, or viruses. When the biopolymer is a protein, it may be an antibody, for example a monoclonal or polyclonal antibody.

The terms "polynucleotides", "nucleic acids", "nucleotides", "probes" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. "Polynucleotide" may also be used to refer to peptide nucleic acids (PNA), locked nucleic acids (LNA), threofuranosyl nucleic acids (TNA) and other unnatural nucleic acids or nucleic acid mimics. Other base and backbone modifications known in the art are encompassed in this definition. See, e.g. De Mesmaeker et al (1997) Pure & Appl. Chem., 69, 3, pp 437-440.

The terms "polypeptide", "peptide" and "protein" are used interchangeably herein to refer to polymers of amino acids of any length. The polymer may be linear, cyclic, or branched, it may comprise modified amino acids, and it may be interrupted by non-amino acids. The terms also encompass amino acid polymers that have been modified, for example, via sulfonation, glycosylation, lipidation, acetylation, phosphorylation, iodination, methylation, oxidation, proteolytic processing, phosphorylation, prenylation, racemization, selenoylation, transfer-RNA mediated addition of amino acids to proteins such as arginylation, ubiquitination, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The term "antibody" as used herein refers to immunoglobulin molecules and immunologically active portions of immunoglobulin molecules, i.e., molecules that contain an antigen-binding site which specifically binds ("immunoreacts with") an antigen. Structurally, the simplest naturally occurring antibody (e.g., IgG) comprises four polypeptide chains, two heavy (H) chains and two light (L) chains inter-connected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. It has been shown that the antigen binding function of an antibody can be performed by fragments of a naturally-occurring antibody. These fragments are collectively termed "antigen-binding units". Antigen binding units can be broadly divided into "single-chain" ("Sc") and "non-single-chain" ("Nsc") types based on their molecular structures.

Also encompassed within the terms "antibodies" are immunoglobulin molecules of a variety of species origins including invertebrates and vertebrates. The term "human" as applies to an antibody or an antigen binding unit refers to an immunoglobulin molecule expressed by a human gene or fragment thereof. The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin.

A "water-soluble group" refers to a chemical group which increases the solubility of the chemical entity it is attached to, and includes groups such as $-L-SO_3^-$, $-L-PO_3^{2-}$, or water-soluble polymers.

The term “stable” refers to compositions and compounds which have sufficient chemical stability to survive isolation from a reaction mixture to a useful degree of purity for use in a desired application.

The terms “fluorescent group”, “fluorophore”, “dye” or “fluorescent group” refer interchangeably to molecules, groups or radicals which are fluorescent. The term “fluorescent” as applied to a molecule of compound is used to refer to the property of the compound of absorbing energy (such as UV, visible or IR radiation) and re-emitting at least a fraction of that energy as light over time. Fluorescent groups, compounds or fluorophores include, but are not limited to discrete compounds, molecules, proteins and macromolecular complexes. Fluorophores also include compounds that exhibit long-lived fluorescence decay such as lanthanide ions and lanthanide complexes with organic ligand sensitizers.

A “subject” as used herein refers to a biological entity containing expressed genetic materials. The subject is in various embodiments, a vertebrate. In some embodiments, the subject is a mammal. In other embodiments, the subject is a human.

A “control” is an alternative subject or sample used in an experiment for comparison purposes. A control can be “positive” or “negative”. For example, where the purpose of the experiment is to detect a differentially expressed transcript or polypeptide in cell or tissue affected by a disease of concern, it is generally preferable to use a positive control (a subject or a sample from a subject, exhibiting such differential expression and syndromes characteristic of that disease), and a negative control (a subject or a sample from a subject lacking the differential expression and clinical syndrome of that disease.

The term “FRET” refers to fluorescence resonance energy transfer. In the present invention, FRET refers to energy transfer processes occurring between at least two fluorescent compounds, between a fluorescent compound and a non-fluorescent component or between a fluorescent component and a non-fluorescent component.

A “binding agent” is a molecule that exhibits binding selectivity towards a binding partner or a target molecule to which it binds. A binding agent may be a biomolecule such as a polypeptide such as an antibody or protein, polypeptide-based toxin, amino acid, nucleotide, polynucleotides including DNA and RNA, lipids, and carbohydrates, or a combination thereof. A binding agent may also be a hapten, drug, ion-complexing agent such as metal chelators, microparticles, synthetic or natural polymers, cells, viruses, or other fluorescent molecules including the dye molecule according to the invention.

A “targeting moiety” is the portion of the binding agent that binds to a binding partner. A targeting moiety may be, without limitation, a nucleotide sequence within a polynucleotide that selectively binds to another polynucleotide or polypeptide. Another nonlimiting example of a targeting moiety may be a polypeptide sequence within a larger polypeptide sequence which binds specifically to a polynucleotide sequence or a second polypeptide sequence. A targeting moiety may be a small molecule or structural motif which will bind to a protein receptor, another small molecule motif, or complexing agent, without limitation. The selective binding may be a specific binding event.

A “binding partner” is a molecule or particle which is bound by the targeting moiety. It can be a cell, virus, fragment of a cell, antibody, fragment of an antibody, peptide, protein, polynucleotide, antigen, small molecule, or a combination thereof. It may be bound selectively or specifically by the binding agent.

The term “signal to noise ratio” of fluorescence as referred to herein in the context of a polypeptide-antibody complex, is the ratio of (fluorescent signal from a complex comprising a polypeptide bound by a primary antibody which in turn is bound to a binding agent labeled with a compound of the invention)/(fluorescent signal from a mixture of the polypeptide, an isotype control primary antibody, and the labeled binding agent).

“Degree of labeling” or “DOL” as used herein herein refers to the number of dye molecules which are attached per target molecule (including but not limited to polypeptide and polynucleotide). For example, a single dye molecule per a polypeptide such as an antibody represents a 1.0 degree of labeling (DOL). If more than one dye molecule, on average, reacts with and is crosslinked to a polypeptide such as an antibody, the degree of labeling is greater than 1 and may further be a number other than a whole integer. The higher the number of DOL, the greater extent of labeling.

“Intracellular” as used herein refers to the presence of a given molecule in a cell. An intracellular molecule can be present within the cytoplasm, attached to the cell membrane, on the surface of an organelle, or within an organelle of a cell.

“Substrate” or “solid substrate” when used in the context of a reaction surface refers to the material that certain interaction is assayed. For example, a substrate in this context can be a surface of an array or a surface of microwell. It may also be a solid such as a polymer which does not form a specific shape but has attachment points on its surface. In some cases, “substrate” may refer to an enzyme substrate, which is a molecule or biomolecule capable of being chemically transformed by an enzyme.

The terms “wavelength of maximum excitation” and “maximal fluorescence excitation wavelength” are used herein interchangeably. These terms refer to the wavelength at which a fluorescent compound is excited to emit maximal fluorescence. The term “absorption maximal wavelength” as applied to a dye refers the wavelength at which a fluorescent dye or nonfluorescent dye has maximal absorption. A fluorescent dye has a “maximal fluorescence emission wavelength” which is the wavelength at which the dye most intensely fluoresces. When a single wavelength is referred to for any dye, it refers to the maximal wavelength of excitation, absorption, or emission, according to the context of the term, for example, an absorption wavelength refers to the wavelength at which the compound has maximal absorption, and an emission wavelength refers to the wavelength at which the dye most intensely fluoresces.

Compounds of the Invention:

The invention provides compounds of Formula 1a or 1b:

Formula 1a

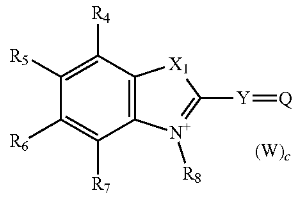

-continued

Formula 1b

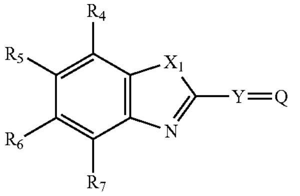

wherein:

$X_1$ is O, S, $NR_1$ or $CR_2R_3$;

$R_1$, $R_2$ and $R_3$ are independently substituted or unsubstituted alkyl, $(R)_p$-$(L)_q$-, or $R_2$ and $R_3$ taken together form a 3-8 membered ring optionally substituted by $(R)_p$-$(L)_q$-;

$R_4$, $R_5$, $R_6$, and $R_7$ are independently hydrogen, halo, —CN, alkoxy, alkyl, aryl, heteroaryl, amino, alkylamino, dialkylamino, alkanecarboxamido, alkanesulfonamido, aminocarbonyl, N-alkylaminocarbonyl, N,N-dialkylaminocarbonyl, N,N,N-trialkylammoniumalkyl, aminosufonyl, N-alkylaminosulfonyl, N,N-dialkylaminosulfonyl, phosphonyl, carboxylate, azide, nitro, arylazo, or $(R)_p$-$(L)_q$-;

at least one substituent pair of $R_4$ and $R_5$, $R_5$ and $R_6$, or $R_6$ and $R_7$, taken together with the atoms it is attached to, is a substituent pair forming a fused ring system according to Formula 1c:

Formula 1c

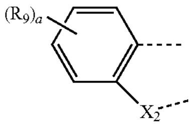

where the dashed lines represent the bonds of the substituent pair connecting to Formula 1a or 1b;

$R_9$ is halo, —CN, alkoxy, alkyl, aryl, heteroaryl, amino, alkylamino, dialkylamino, alkanecarboxamido, alkanesulfonamido, aminocarbonyl, N-alkylaminocarbonyl, N,N-dialkylaminocarbonyl, N,N,N-trialkylammoniumalkyl, aminosufonyl, N-alkylaminosulfonyl, N,N-dialkylaminosulfonyl, phosphonyl, sulfonate, carboxylate, azide, nitro, arylazo, or $(R)_p$-$(L)_q$-;

a is 0, 1, 2, 3, or 4;

$X_2$ is O, S, $NR_{10}$, $SiR_{11}R_{12}$, or $CR_{11}R_{12}$, where each $R_{10}$, $R_{11}$ and $R_{12}$ is substituted or unsubstituted alkyl, $(R)_p$-$(L)_q$, or $R_{11}$ and $R_{12}$ taken together form a 3-8 membered ring, optionally substituted by $(R)_p$-$(L)_q$;

Y is a bridge unit that permits electron delocalization;

Q is optionally substituted aryl or heteroaryl;

$R_8$ is H, substituted or unsubstituted alkyl, substituted or unsubstituted aryl, substituted or unsubstituted heteroaryl, or $(R)_p$-$(L)_q$-; or $R_8$ taken together with $R_7$ forms a saturated or unsaturated 5- or 6-membered ring, optionally substituted; or $R_8$, taken together with a substituent on the moiety Y, forms a 5- or 6-membered saturated or unsaturated ring; or $R_8$, taken together with a substituent on the moiety Q, forms a macrocycle;

W is a counter ion;

c is an integer indicating the number of W such that the overall charge of Formula 1 is zero;

each R of each $(R)_p$-$(L)_q$- substituent is independently i) a reactive group capable of forming a covalent bond upon reacting with a reaction substrate; ii) a water-soluble group; or iii) a biopolymer;

each L of each $(R)_p$-$(L)_q$- substituent is independently a linking moiety formed of one or more chemical bonds and containing about 1-100 atoms;

each p of each $(R)_p$-$(L)_q$- is independently an integer of about 1 to about 20;

each q of each $(R)_p$-$(L)_q$- of $R_1$ or $R_2$ is independently an integer of 0 to about 20; and the compound of Formula 1 comprises at least one substituent which is $(R)_p$-$(L)_q$-.

In some embodiments of the compounds of the invention, $X_1$ is O. In other embodiments, $X_1$ is S. In still other embodiments, $X_1$ is —$CR_2R_3$—. For example, $X_1$ is —$C(CH_3)R_3$—.

In some embodiments, $R_1$, $R_2$ and $R_3$ are independently substituted or unsubstituted alkyl.

In some embodiments, $X_1$ is —$CR_2R_3$—, $R_2$ is —$CH_3$— and $R_3$ is alkyl, for example $C_2$-$C_{20}$ alkyl, optionally substituted by $(R)_p$-$(L)_q$-. In still other embodiments, $X_1$ is —$C(CH_3)_2$—.

In still other embodiments, $R_2$ and $R_3$ taken together form a 3-8 membered ring optionally substituted by $(R)_p(L)_q$-. For example, $R_2$ and $R_3$ taken together are cyclopropyl, cyclobutyl or cyclopentyl, optionally substituted by $(R)_p$-$(L)_q$-. In other embodiments, $R_1$, $R_2$ and $R_3$ are $(R)_p$-$(L)_q$-.

In some embodiments, $R_4$, $R_5$, $R_6$, and $R_7$ are independently hydrogen, halo, —CN, alkoxy, alkyl, aryl, heteroaryl, amino, alkylamino, dialkylamino, alkanecarboxamido, alkanesulfonamido, aminocarbonyl, N-alkylaminocarbonyl, N,N-dialkylaminocarbonyl, N,N,N-trialkylammoniumalkyl, aminosufonyl, N-alkylaminosulfonyl, N,N-dialkylaminosulfonyl, phosphonyl, carboxylate, azide, nitro, arylazo, or $(R)_p$-$(L)_q$-. In some embodiments, $R_4$, $R_5$, $R_6$, or $R_7$ is hydrogen.

In some embodiments, at least one substituent pair of $R_4$ and $R_5$, $R_5$ and $R_6$, or $R_6$ and $R_7$, taken together with the atoms it is attached to, is a substituent pair forming a fused ring system. In some embodiments, $R_5$ and $R_6$, taken together with the atoms it is attached to, is a substituent pair forming a fused ring system according to Formula 1c. Such compounds include compounds of Formula 1c-1 and 1c-2:

Formula 1c-1

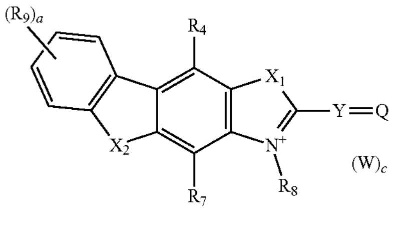

Formula 1c-2

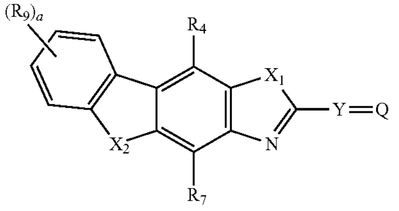

In some embodiments, $R_4$ and $R_7$ are hydrogen.

In some embodiments, $R_9$ is halo, —CN, alkoxy, alkyl, aryl, heteroaryl, amino, alkylamino, dialkylamino, alkanecarboxamido, alkanesulfonamido, aminocarbonyl, N-alkylaminocarbonyl, N,N-dialkylaminocarbonyl, N,N,N-trialkylammoniumalkyl, aminosufonyl, N-alkylaminosulfonyl, N,N-dialkylaminosulfonyl, phosphonyl, sulfonate, carboxylate, azide, nitro, arylazo, or $(R)_p$-$(L)_q$-. In some embodiments, $R_9$ is sulfonate. The variable a indicates the number of $R_9$ substituents as chemically permissible and is 0, 1, 2, 3, or 4. For example, a is 0 when no $R_9$ substituents are present. In some embodiments, a is 0 or 1. In some embodiments, a is 1. In some embodiments, a is 1 and $R_9$ is sulfonate.

In some embodiments, $X_2$ is O, S, $NR_{10}$, $SiR_{11}R_{12}$, or $CR_{11}R_{12}$, where each $R_{10}$, $R_{11}$ and $R_{12}$ is substituted or unsubstituted alkyl, $(R)_p$-$(L)_q$-, or $R_{11}$ and $R_{12}$ taken together form a 3-8 membered ring, optionally substituted by $(R)_p$-$(L)_q$-. In some embodiments, $X_2$ is $CR_{11}R_{12}$. For instance, $X_2$ is $CR_{11}R_{12}$ and $R_{11}$ and $R_{12}$ are independently alkyl, unsubstituted or substituted by $(R)_p$-$(L)_q$-. For example, each $R_{11}$ and $R_{12}$ is independently $C_2$-$C_{20}$ alkyl. In some embodiments, $X_2$ is $CR_{11}R_{12}$ and $R_{11}$ and $R_{12}$ are methyl. In some embodiments, $X_2$ is $CR_{11}R_{12}$ and $R_{11}$ and $R_{12}$ taken together form a 3-8 membered ring, optionally substituted by $(R)_p$-$(L)_q$-. For instance, $R_{11}$ and $R_{12}$ form a 6-membered ring, optionally substituted by $(R)_p(L)_q$-.

Y is a bridge unit permitting electron delocalization across the compound of the invention. In some embodiments, Y is a methine or polymethine unit, such as a tri-, penta-, or heptamethine unit. Y may also be a cyclic group, including but not limited to a heterocyclic group. In some embodiments, Y is a 4, 5, or 6-membered ring.

In some embodiments, Y is:

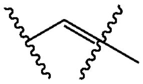
,
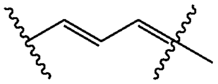
,
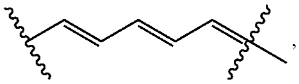
,
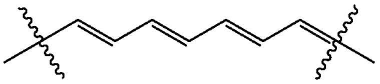
,
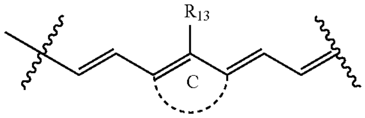
,
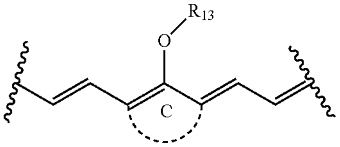
,
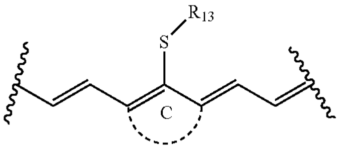
,
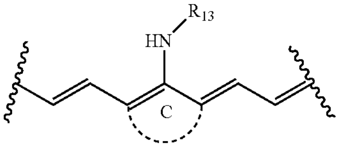
,
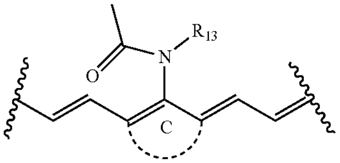
, -continued

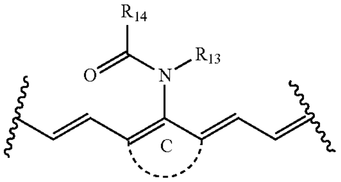
or
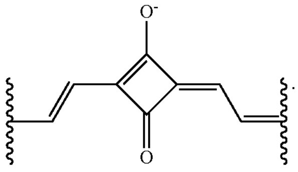

wherein C is a five- or six-membered cyclic group;

$R_{13}$ is H, alkyl, aryl, heteroaryl, or $(R)_p$-$(L)_q$-; and $R_{14}$ is alkyl, aryl, heteroaryl, or $(R)_p(L)_q$-.

In some embodiments, Y is

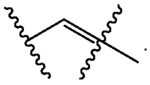 [SMILES: *C=*]
.

In other embodiments, Y is

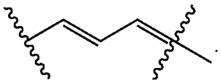 [SMILES: */C=C/C=*]
.

In still other embodiments, Y is

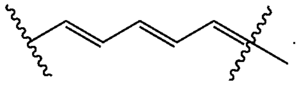 [SMILES: */C=C/C=C/C=*]
.

In still other embodiments, Y is

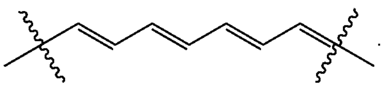 [SMILES: */C=C/C=C/C=C/C=*]
.

In yet other embodiments, Y is

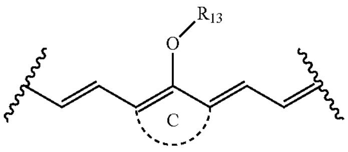

where $R_{13}$ is H, alkyl, aryl, heteroaryl, or $(R)_p$-$(L)_q$-. For example, $R_{13}$ is $(R)_p$-$(L)_q$-. In still other embodiments, Y is

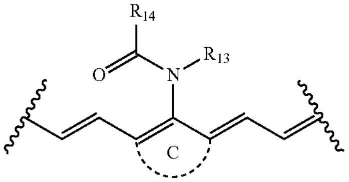

where $R_{13}$ and $R_{14}$ are independently $(R)_p(L)_q$-, for example where $R_{13}$ is $(R)_p(L)_q$- where $R_{13}$ is a water-soluble group, and $R_{14}$ is $(R)_p(L)_q$- where R is a reactive group capable of forming a covalent bond upon reacting with a reaction substrate.

The substituent Q is optionally substituted aryl or heteroaryl. In some embodiments, Q is substituted with $R_9$. In some embodiments, Q is one of the following structures:

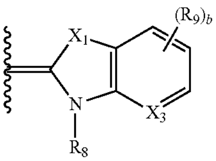
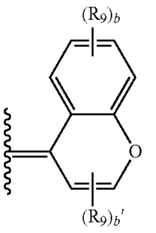
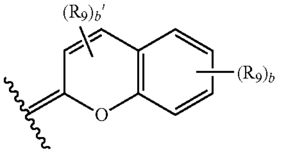
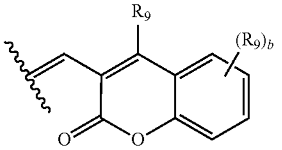
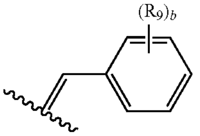
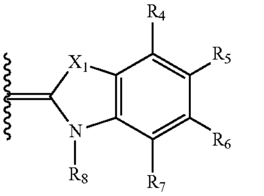

where each substituent $R_4$, $R_5$, $R_6$, $R_7$, $R_8$, or $R_9$, and each b or b' is independently chosen.

In some embodiments, Q is

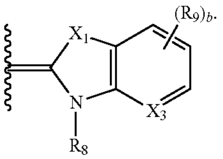

The substituent $X_3$ is

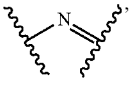, 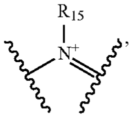, or 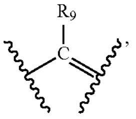, where $R_{15}$ is H, alkyl or $(R)_p$-$(L)_q$-. In some embodiments, $X_3$ is

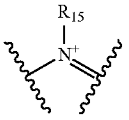

and $R_{15}$ is H. In other embodiments, $X_3$ is

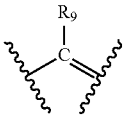

and $R_9$ is H.

In some embodiments, Q is

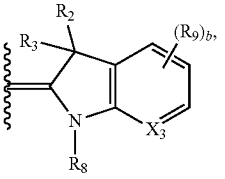

where $X_3$ is

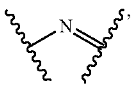, 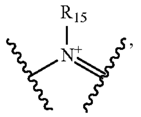, or 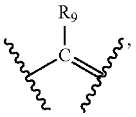, where $R_{15}$ is H, alkyl or $(R)_p$-$(L)_q$-. For example, Q is

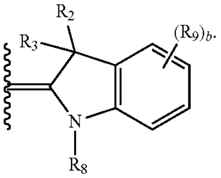

In some embodiments, Q is

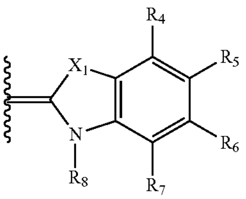

where $X_1$, $R_4$, $R_5$, $R_6$, $R_7$ and $R_8$ are as previously defined. In some embodiments, $R_4$, $R_5$, $R_6$, and $R_7$ are independently hydrogen, halo, —CN, alkoxy, alkyl, aryl, heteroaryl, amino, alkylamino, dialkylamino, alkanecarboxamido, alkanesulfonamido, aminocarbonyl, N-alkylaminocarbonyl, N,N-dialkylaminocarbonyl, N,N,N-trialkylammoniumalkyl, aminosufonyl, N-alkylaminosulfonyl, N,N-dialkylamino-sulfonyl, phosphonyl, carboxylate, azide, nitro, arylazo, or $(R)_p$-$(L)_q$-. In some embodiments, $R_4$, $R_5$, $R_6$, or $R_7$ is hydrogen. In some embodiments, $R_5$ and $R_6$, taken together with the atoms it is attached to, is a substituent pair forming a fused ring system according to Formula 1d:

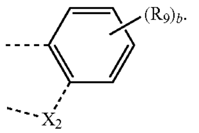

Such embodiments of Q include Formulas 1d-1:

Formula 1d-1

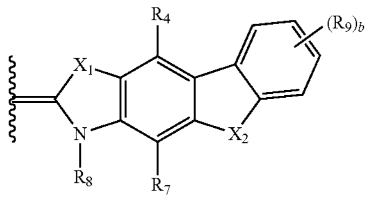

In some embodiments of Formula 1d-1, $X_1$ is O. In other embodiments, $X_1$ is S. In still other embodiments, $X_1$ is —$CR_2R_3$—. For example, $X_1$ is —$C(CH_3)R_3$—. In some embodiments of Formula 1d-1, $X_2$ is O, S, $NR_{10}$, $SiR_{11}R_{12}$, or $CR_{11}R_{12}$, where each $R_{10}$, $R_{11}$ and $R_{12}$ is substituted or unsubstituted alkyl, $(R)_p(L)_q$-, or $R_{11}$ and $R_{12}$ taken together form a 3-8 membered ring, optionally substituted by $(R)_p$-$(L)_q$-. In some embodiments, $X_2$ is $CR_{11}R_{12}$. For instance, $X_2$ is $CR_{11}R_{12}$ and $R_{11}$ and $R_{12}$ are independently alkyl, unsubstituted or substituted by $(R)_p$-$(L)_q$-. For example, each $R_{11}$ and $R_{12}$ is independently $C_2$-$C_{20}$ alkyl. In some embodiments, $X_2$ is $CR_{11}R_{12}$ and $R_{11}$ and $R_{12}$ are methyl. In some embodiments, $X_2$ is $CR_{11}R_{12}$ and $R_{11}$ and $R_{12}$ taken together form a 3-8 membered ring, optionally substituted by $(R)_p(L)_q$-. For instance, $R_{11}$ and $R_{12}$ form a 6-membered ring, optionally substituted by $(R)_p$-$(L)_q$-.

In general, each L of each $(R)_p(L)_q$- substituent is independently a linking moiety formed of one or more chemical bonds and containing about 1-100 atoms. In some embodiments, linking moieties are formed of 1-50 non-hydrogen atoms as well as additional hydrogen atoms. Such atoms may be, for example, C, N, O, P or S. In other embodiments, a linker moiety connecting two groups comprises 1 to 50 consecutive bonds between the groups. Some linker moieties may have 1 to 40, 1 to 30, 1 to 20, 1 to 10, 1 to 5, 5 to 25, or 5 to 20 such consecutive bonds. If the subscript q is indicated to be 0, the entity -$(L)_q$- is understood to represent a bond.

Non-limiting exemplary linking moieties are illustrated below:

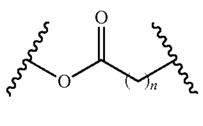

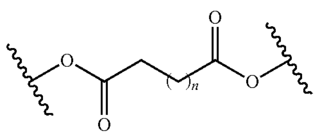

-continued

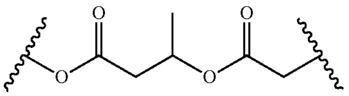

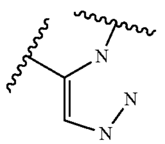

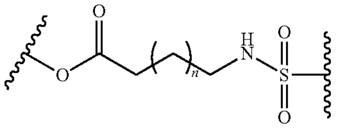

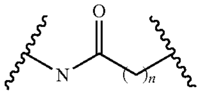

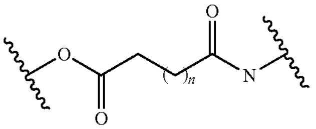

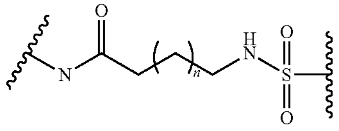

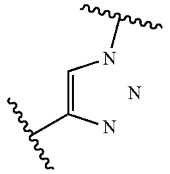

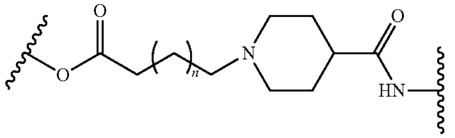

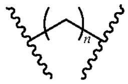

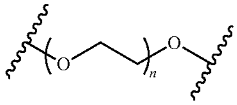

In the above image, n represents a number of repeating methylene units which can be varied such as to provide a desired length of the linker. Typically, n ranges from 1 to about 50. Some linkers will have an n of 1 to 40, 1 to 30, 1 to 20, 1 to 10, 1 to 5, 5 to 30, 5 to 20, or 5 to 15.

In some cases, the L of an $(R)_p(L)_q$- group is a bond. In other cases, L is polymethylene —$(CH_2)_n$—, where n is from 1 to about 6. In other cases, the L of an $(R)_p(L)_q$- group may comprise a water-soluble moiety, such as a polyethylene glycol (or PEG) unit, where the number of ethylene glycol unit may be from 1 to about 30, for example. More typically, the number of ethylene glycol unit is from 1 to about 24. In some cases, the L of $(R)_p(L)_q$- comprises a PEG moiety of 8 ethylene glycol units. In other cases, the PEG moiety comprises 12 ethylene units.

Some but not all of compounds of the invention may comprise at least one $(R)_p(L)_q$- where R is a reactive group capable of forming a covalent bond upon reacting with a reaction substrate. A reactive group is a chemical moiety capable of reacting with a reaction partner on a substrate or substrate molecule to form a covalent bond. A compound of the invention can be used to label a wide variety of molecules or substrates that contain a suitable reaction partner or are derivatized to contain a suitable reaction partner. "Reactive group" and "reaction partner" may refer to groups on a compound of the present invention, or to groups on a molecule to be labeled. Here, by way of convenience, but not limitation, a bond-forming group on a compound will generally be referred to as a reactive group and a bond-forming group on the substrate molecule will generally be referred to as a reaction partner.

In any of the structural formulas shown herein, "R" may be any reactive group that confers a desirable functional property to the compound of the invention. The reactive group and its reaction partner may be an electrophile and a nucleophile, respectively, that can form a covalent bond with or without a coupling agent or catalyst. According to one embodiment, the reactive group is a photoactivatable group capable of reacting with a hydrocarbon molecule upon ultraviolet photoactivation or photolysis. According to another embodiment, the reactive group is a dienophile capable of reacting with a conjugated diene via a Diels-Alder reaction. According to yet another embodiment, the reactive group is a 1,3-diene capable of reacting with a dienophile. According to still another embodiment, the reactive group is an alkyne capable of reacting with an azido functional group to form a 1,2,3-triazole linkage. According to still another embodiment, the reactive group is a 2-(diphenylphosphino)benzoic acid methyl ester capable of reacting with an azido functional group to form an amide linkage via so-called Staudinger reaction. Merely by way of example, examples of useful reactive groups, functional groups, and corresponding linkages according to the present invention are listed below in Table 1.

TABLE 1

Examples of Reactive Groups, Functional Groups, and Covalent Linkages

| Reactive Group | Reaction Partner/ Substrate | Resulting Covalent Linkage |
|---|---|---|
| activated esters * | amines/anilines | Carboxamides |
| acrylamides | Thiols | Thioethers |
| acyl azides** | amines/anilines | Carboxamides |
| acyl halides | amines/anilines | Carboxamides |
| acyl halides | Alcohols/phenols | Esters |
| acyl nitriles | Alcohols/phenols | Esters |
| acyl nitriles | amines/anilines | Carboxamides |
| aldehydes | amines/anilines | Imines |
| aldehydes or ketones | Hydrazines | Hydrazones |
| aldehydes or ketones | Hydroxylamines | Oximes |
| alkyl halides | amines/anilines | alkyl amines |
| alkyl halides | Thiols | Thioethers |
| alkyl halides | alcohols/phenols | Esters |
| alkyl sulfonates | Thiols | Thioethers |
| alkyl sulfonates | carboxylic acids | Esters |
| alkyl sulfonates | alcohols/phenols | Esters |
| anhydrides | alcohols/phenols | Esters |
| anhydrides | amines/anilines | Carboxamides |
| aryl halides | Thiols | Thiophenols |
| aryl halides | Amines | aryl amines |
| aziridines | Thiols | Thioethers |
| boronates | Glycols | boronate esters |
| epoxides | Thiols | Thioethers |
| haloacetamides | Thiols | Thioethers |
| halotriazines | amines/anilines | Aminotrizaines |
| halotriazines | alcohols/phenols | triazinyl ethers |
| imido esters | amines/anilines | Amidines |
| isocyanates | amines/anilines | Ureas |
| isocyanates | alcohols/phenols | Urethanes |
| isothiocyanates | amines/anilines | Thioureas |
| maleimides | Thiols | Thioethers |
| phosphoramidites | Alcohols | phosphite esters |
| silyl halides | Alcohols | silyl ethers |
| sulfonate esters | amines/anilines | alkyl amines |
| sulfonate esters | Thiols | Thioethers |
| sulfonate esters | Alcohols | Ethers |
| sulfonyl halides | amines/anilines | Sulfonamides |
| sulfonyl halides | phenols/alcohols | sulfonate esters |
| azide | alkyne | 1,2,3-triazole |

TABLE 1-continued

Examples of Reactive Groups, Functional Groups, and Covalent Linkages

| Reactive Group | Reaction Partner/ Substrate | Resulting Covalent Linkage |
|---|---|---|
| Cis-platinum | guanosine | Platinum-guanosine complex |

* Activated esters, as understood in the art, generally have the formula —COΩ, where Ω is a good leaving group, such as succinimidyloxy (—$OC_4H_4O_2$), sulfosuccinimidyloxy (—$OC_4H_3O_2$—$SO_3H$), or -1-oxybenzotriazolyl (—$OC_6H_4N_3$), for example; or an aryloxy group or aryloxy substituted one or more times by electron-withdrawing substituent(s), such as nitro, fluoro, chloro, cyano, trifluoromethyl, or combinations thereof, for example, used to form activated aryl esters; or a carboxylic acid activated by a carbodiimide to form an anhydride or mixed anhydride —$OCOR^a$ or —$OCNR^aNHR^b$, where $R^a$ and $R^b$, which may be the same or different, are independently $C_1$-$C_6$ alkyl, $C_1$-$C_6$ perfluoroalkyl, or $C_1$-$C_6$ alkoxy; or cyclohexyl, 3-dimethylaminopropyl, or N-morpholinoethyl.
**Acyl azides can also rearrange to isocyanates.

The reactive group may be one that will react with an amine, a thiol, a hydroxyl or an aldehyde. The reactive group may be an amine-reactive group, such as a succinimidyl ester (SE), for example, or a thiol-reactive group, such as a maleimide, a haloacetamide, or a methanethiosulfonate (MTS), for example, or an aldehyde-reactive group, such as an amine, an aminooxy, or a hydrazide, for example.

Choice of the reactive group used to attach the fluorophore to the substance to be conjugated typically depends on the functional group on the substance to be conjugated and the type or length of covalent linkage desired. The types of functional groups typically present on the organic or inorganic substances include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the substance (typical for polysaccharides), or a variety of sites may occur (e.g. amines, thiols, alcohols, phenols), as is typical for proteins. A conjugated substance may be conjugated to more than one fluorophore, which may be the same or different, or to a substance that is additionally modified by a hapten, such as biotin. Although some selectivity can be obtained by careful control of the reaction conditions, selectivity of labeling is best obtained by selection of an appropriate reactive dye.

In some embodiments, R will react with an amine, a thiol, an alcohol, an aldehyde or a ketone. In one embodiment, R is an acrylamide, an activated ester of a carboxylic acid, an acyl azide, an acyl nitrile, an aldehyde, an alkyl halide, an amine, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a sulfonyl halide, or a thiol group. In other embodiments, R is a carboxylic acid, a succinimidyl ester, an azidoperfluorobenzamido group, a pyrrole-2,5-dione, a tetrafluorophenol ester, an imido ester, an azidonitrophenyl, an alkyne, a 3-(2-pyridyl dithio)-propionamide, a glyoxal or an aldehyde. Where the reactive group is a photoactivatable group, such as an azide, diazirinyl or azidoaryl derivative, the dye becomes chemically reactive only after illumination with light of an appropriate wavelength. Where R is a succinimidyl ester of a carboxylic acid, the reactive dye is particularly useful for preparing dye-conjugates of proteins or oligonucleotides. Where R is a maleimide, the reactive dye is particularly useful for conjugation to thiol-containing substances. Where R is a hydrazide, the reactive dye is particularly useful for conjugation to periodate-oxidized carbohydrates and glycoproteins, and in addition is an aldehyde-fixable polar tracer for cell microinjection.

The compounds of the invention may also comprise at least one $(R)_p(L)_q$- where R is a water-soluble group. According to the invention, water soluble groups may significantly reduce the intramolecular mobility of the fluorescent group core structure and may thus improve the fluorescent group's fluorescence quantum yield. Such groups may also confer other properties to the compounds to which they are attached, such as improvements of the photostability of the fluorescent group, reduced fluorescent group aggregation for biomolecule labeling, increased staining specificity of fluorescently labeled biomolecules (such as antibodies); and reduced immunogenicity and antigenicity of labeled biomolecules (such as antibodies) in vivo.

Water soluble groups include water soluble polymer groups which are generally substantially unreactive and water-soluble moieties sufficiently large to improve the fluorescence properties of a compound. The term "polymer" used in this context does not require the presence of strictly repeating units. A molecule of sufficient molecular size and solubility but without repeating units is considered a "water soluble polymer group" for the purposes of the invention.

Water soluble groups include, but are not limited to, organic polymers and biomolecules such as polypeptides and carbohydrates. Water soluble polymers may comprise ether groups, hydroxyl groups, tertiary amine groups, quaternized amine groups, and/or guanidine groups. Each water soluble polymer may be linear, branched, cyclic or a combination thereof. Water soluble polymers of the invention may comprise a single chain or alternatively one, two, three, four or more chains. Water soluble polymers with one, two, three, four or more branches may be used. The compounds of the invention may comprise any number of water soluble polymer groups. Generally, compounds of the invention comprise at least 1 water soluble polymer groups up to about 8 water soluble polymer groups. In one embodiment, a compound comprises at least 2 water soluble polymer groups to about 8 water soluble polymer groups. In another embodiment, a compound comprises at least 3 water soluble polymer groups up to about 8 water soluble groups. Suitable molecular weights of each water soluble polymer group or, alternatively, of all water soluble polymer groups in one compound may be about 100, 200, 300, 400, 500, 600, 700, 800, 900, 1000, 1500, 2000, 2500, 3000, 3500, 4000, 4500, 5000, 10000, 15000, 20000 Da or greater. In one embodiment, the water soluble polymer group of the invention has a molecular weight between 450 and 5000 Da. In another embodiment, the water soluble polymer group of the invention has a molecular weight between about 800 and about 3000 Da. In yet another embodiment, the combined molecular weight of all water soluble polymer groups within a compound is from about 450 to about 5,000 Da. In still another embodiment, the combined molecular weight of all water soluble polymer groups within a compound is from about 1,000 to about 3,000 Da.

In one embodiment, the water soluble polymer of the invention is a polyalkylene oxide. Suitable polyalkylene oxides include polyethylene glycol (PEG), polypropylene glycol (PPG), polyethylene glycol-polypropylene glycol (PEG-PPG) copolymers, and N-substituted methacrylamide-containing polymers and copolymers. Various polyalkylene oxides suitable for the present invention, as well as methods of making and using them are described in the following references: U.S. Pat. Nos. 5,637,749; 5,650,388; 5,298,643; 5,605,976; 5,567,422; 5,681,567; 5,321,095; 5,349,001; 5,405,877; 5,234,903; 5,478,805; 5,324,844; 5,612,460; 5,756,593; 5,686,110; 5,880,131; 6,824,782; 5,808,096; 6,013,283; 6,251,382. Commercial sources of polyalkylene oxide reagents include Sigma-Aldrich, Nanocs, Creative Biochem, Pierce, Enzon, Nektar and Nippon Oils and Fats. Exemplary polyalkylene oxide groups are shown below:

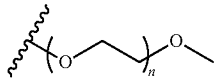

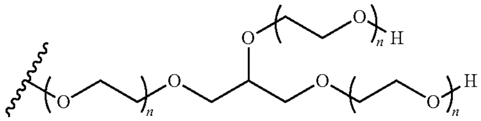

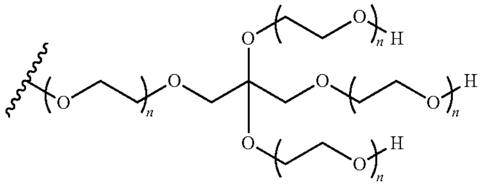

Polyalkylene oxides may be additionally substituted as necessary to confer other desired properties to the polymer. Such modifications may comprise, for example, chemical linkages that increase or decrease the chemical stability of the polymer, which would allow tuning of the chemical or biological stability of the half-life of the polymer. In some cases, polyalkylene oxide molecules are terminated or "capped" with various groups. Examples of such groups are hydroxy, alkyl ether (e.g. methyl, ethyl, propyl ethers), carboxymethyl ether, carboxyethyl ether, benzyl ether, dibenzylmethylene ether or dimethylamine. A polyalkylene oxide may have one of many possible terminals, including but not limited to hydroxyl, methyl ether, ethyl ether, carboxymethyl ether, and carboxyethyl ether. In one embodiment, a polyalkylene oxide is a polyethylene glycol polymer terminated with a methyl ether. Such a group may be referred to as an mPEG. An mPEG generally has the formula of $—(CH_2CH_2O)_nCH_3$, wherein n is the number of ethylene glycol units and is determined by the size of said mPEG.

Other suitable polymers include derivatives and conjugates of poly(2-hydroxyethyl methacrylate), polyhydroxypropyl methacrylamide, poly(styrene sulfonic acid), poly (vinyl alcohol), or poly(2-vinyl N-methyl pyridinium iodide).

In another embodiment, the water soluble polymer of the invention is a carbohydrate. Such carbohydrates include monosaccharides or polysaccharides and may be, for example, soluble starch, glycogen, dextran, pectin, mannan, galactan, hydroxymethylcellulose, hydroxyethylcellulose and other derivatized celluloses. When the water soluble polymer is a carbohydrate, at least 30% of the hydroxyl groups present in the carbohydrate may be masked as methyl ethers, sulfonatoalkyl ethers, and/or acetate esters.

In yet another embodiment, the water soluble polymer of the invention is a polypeptide. Suitable polypeptides may comprise, for example, serine, arginine, polylysine with modified epsilon amino groups, or cysteinic acid. Other examples of such polypeptides are disclosed, for example, in WO 2006/081249. It is contemplated that such polypeptides may be used as the water soluble polymer of the invention.

Water soluble polymers of the invention also comprise combinations of the different classes described above. For example, such a water soluble polymer would be a polypeptide linked to a polyalkylene oxide moiety.

Water soluble polymers do not generally comprise any group or groups that are incompatible with the chemistry of the reactive group or groups included in the compound of the invention. For example, a water soluble polymer should not comprise strong nucleophiles if a reactive group is an electrophile. In a more specific example, a water soluble polymer should not comprise primary or secondary amines if a reactive group is an N-hydroxysuccinimidyl ester. As another specific example, a water soluble polymer should not comprise a thiol when a reactive group is a maleimide. Likewise, a water soluble polymer should generally not comprise a strong electrophile if a reactive group is a nucleophile. However, a water soluble may comprise a minimal number of weak nucleophiles or a minimal number of weak electrophiles such that the chemistry of the reactive group is not significantly affected, or the stability of the compound of the invention is not affected during storage and handling. Examples of weak nucleophiles are hydroxyl groups, which are commonly present in carbohydrate molecules. Thus, in some embodiments, when a water soluble polymer is a carbohydrate molecule, at least 30% of the hydroxyl groups are preferably masked as ethers, such as methyl ether, and/or as esters, such as acetate esters. In other embodiments, all of the hydroxyl groups may be masked as ethers and/or esters.

In general, additional water soluble groups R can in some cases be groups such as sulfonate ($—SO_3^-$), phosphonate ($—PO_3^{2-}$), and ammonium groups. Herein, the term ammonium means $NH_4$+, a trialkylammonium, or a tetraalkylammonium. One of skills can appreciate that an ionic group requires a counter ion to balance its charge. For example, each negatively charged $—SO_3^-$ or $—PO_3^{2-}$ may necessitate one or two cations to balance the negative charge. Likewise, a positively charged ammonium may require an anion to maintain neutrality. In general, the nature of the counter ion is not critical as long as the counter ion does not lower the solubility of said fluorescent group. In some embodiments, when a substituent is $—SO_3^-$ or $—PO_3^{2-}$, the counter ion is $H^+$, $Na^+$, $K^+$ or an ammonium. In other embodiments, when the substituent is ammonium, the counter ion is preferably chloride, fluoride, bromide, sulfate, phosphate, acetate or the like. Some fluorescent groups may intrinsically possess a positive charge or negative charge. In such a case, the intrinsic charge may act as a counter ion. Alternatively, the intrinsic charge may require a counter ion for maintaining neutrality. The rule for selecting a counter ion for any intrinsic charge is as previously described. In some embodiments of the invention, at least one sulfonate group is present ($—SO_3^-$) and any necessary counter ion is selected from $H^+$, $Na^+$, $K^+$ and an ammonium. For reason of simplicity, any dissociable counter ion or counter ions for most of the fluorescent group structures depicted herein may not be shown.

Such substituents may increase a compound's water solubility and/or its fluorescent quantum yield. However, a relatively high number of charged groups is generally not desirable because it would result in a highly charged fluorophore, which on conjugation to a protein, for example, may significantly change the isoelectric point of the protein, thus possibly affecting the biological properties of the labeled protein. For example, an antibody labeled with a highly charged fluorescent molecule may show high background in staining. In some embodiments, the number of such charged water-soluble R groups is 0-4, or 0-3. Because the fluorescent group of the invention has at least one water soluble polymer group, which is also capable of increasing the water solubility and/or the quantum yield of the fluorescent group, the number of charged R groups, such as sulfonate groups, can be kept to a minimum, thereby minimizing the loss of biological specificity of labeled proteins.

Exemplary compounds of the invention along with their known fluorescence properties are shown in Table 2 where $\lambda^{ex}$ denotes excitation wavelength and $\lambda^{em}$ denotes emission wavelength:

| No. | Structure | $\lambda^{ex}$ (nm) | $\lambda^{em}$ (nm) |
|---|---|---|---|
| E1 | 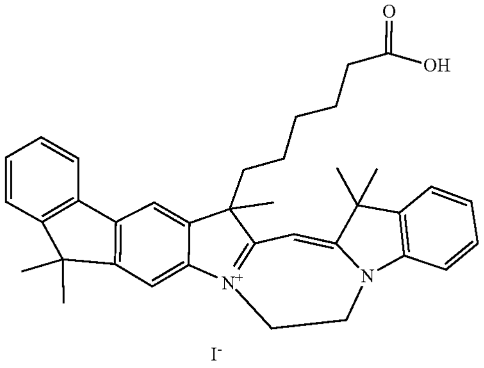 [SMILES: CC1(C)C2=CC3=[N+](CCN2c2ccccc21)c1cc2c(cc1C3(C)CCCCCC(=O)O)-c1ccccc1C2(C)C ; [I-]] | 445 | 518 |

-continued
| No. | Structure | $\lambda^{ex}$ (nm) | $\lambda^{em}$ (nm) |
|---|---|---|---|
| E2 | 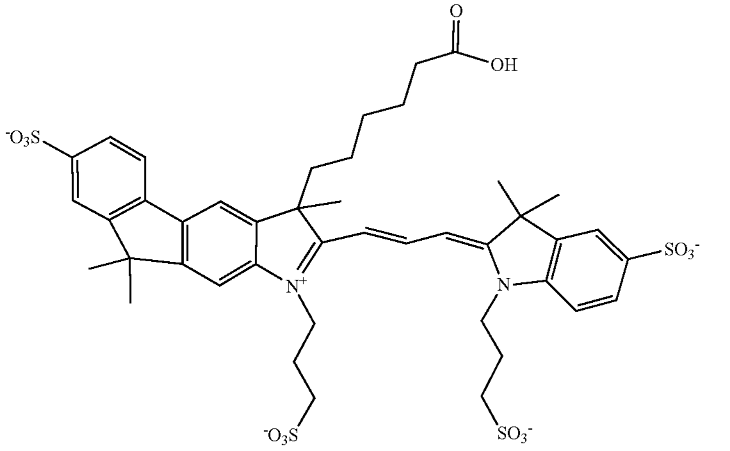 | 572 | 602 |
| E3 | 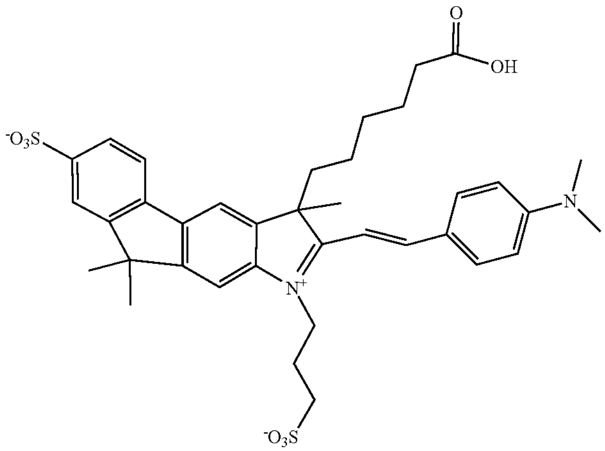 | | |
| E4 | 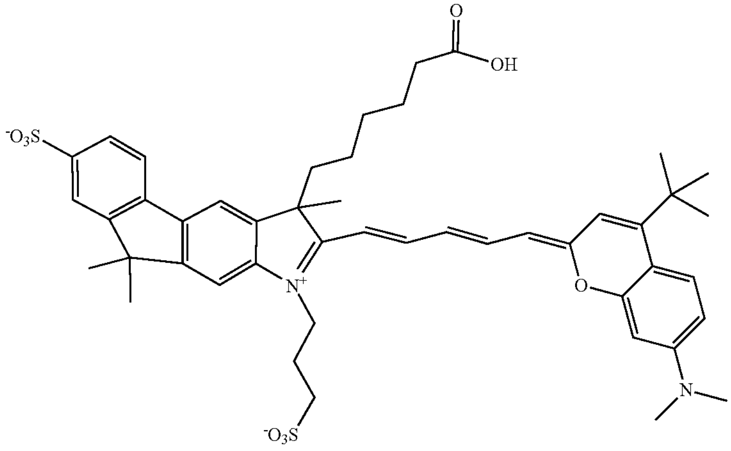 | | |

-continued
| No. | Structure | $\lambda^{ex}$ (nm) | $\lambda^{em}$ (nm) |
|---|---|---|---|
| E5 | 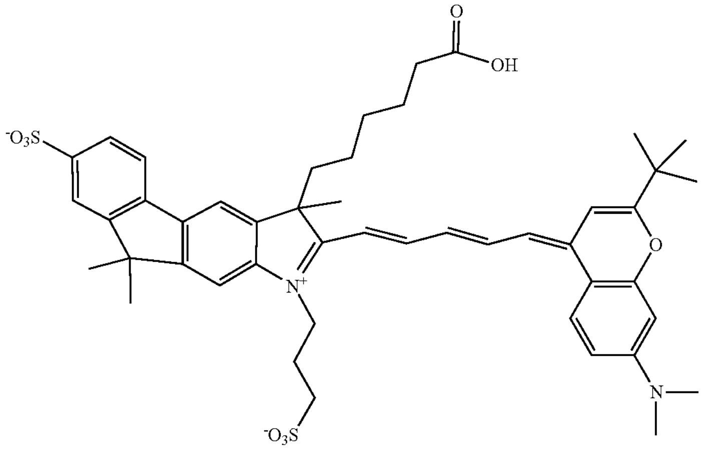 | | |
| E6 | 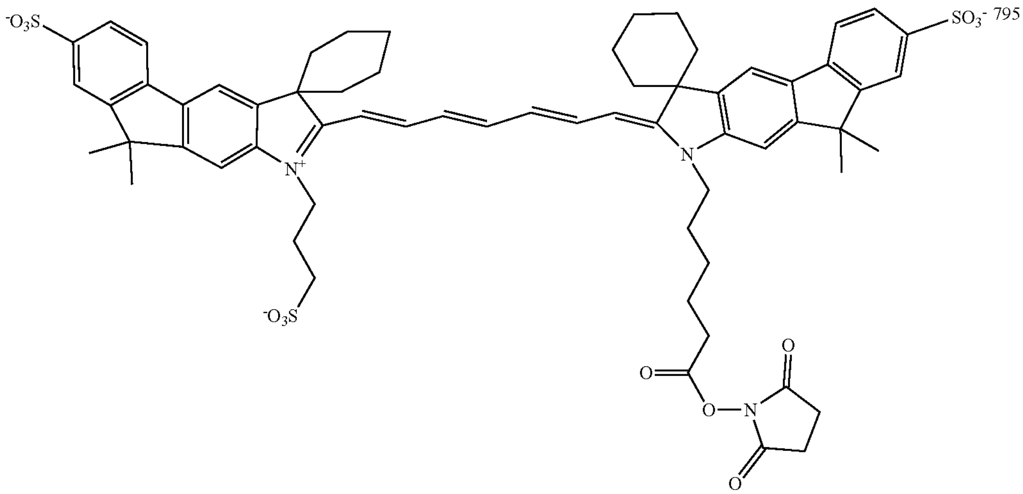 | 795 | 820 |
| E7 | 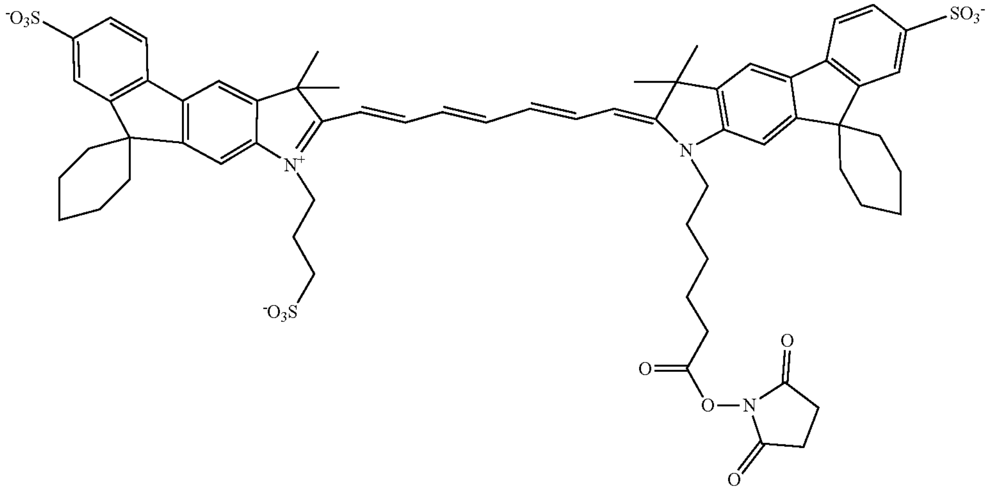 | 793 | 817 |

-continued
| No. | Structure | $\lambda^{ex}$ (nm) | $\lambda^{em}$ (nm) |
|---|---|---|---|
| E8 | 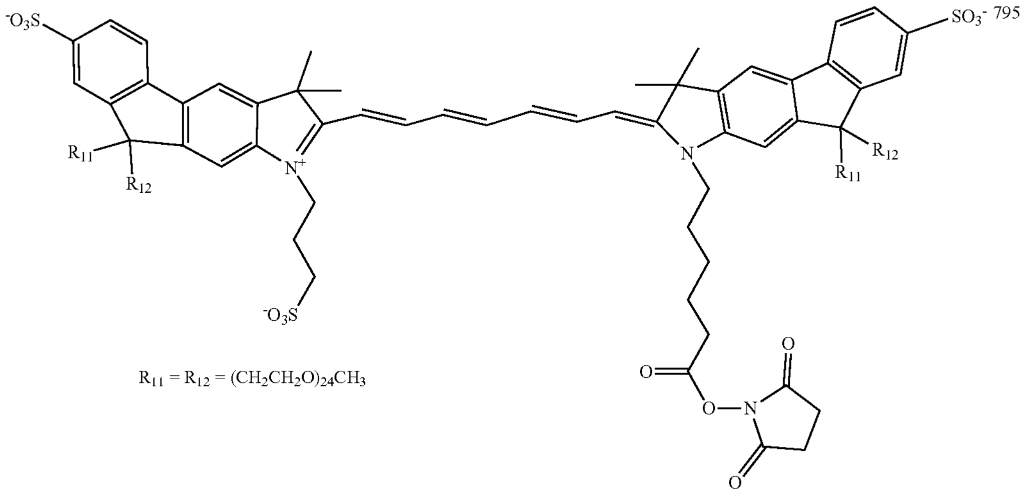 $R_{11} = R_{12} = (CH_2CH_2O)_{24}CH_3$ | 795 | 820 |
| E9 | 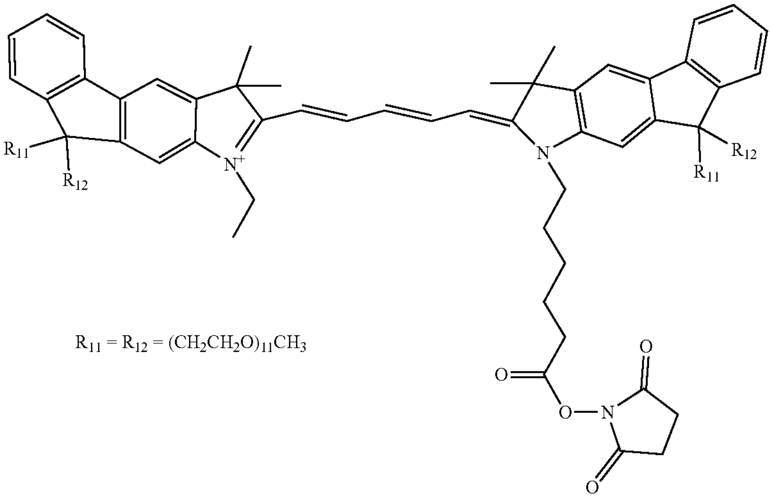 $R_{11} = R_{12} = (CH_2CH_2O)_{11}CH_3$ | 697 | 717 |
| E10 | 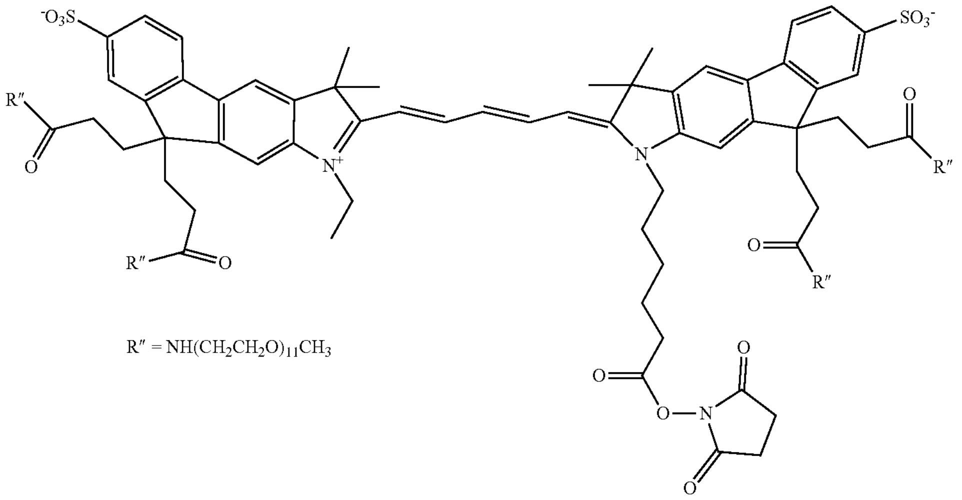 $R'' = NH(CH_2CH_2O)_{11}CH_3$ | 695 | 720 |

-continued
| No. | Structure | $\lambda^{ex}$ (nm) | $\lambda^{em}$ (nm) |
|---|---|---|---|
| E11 | 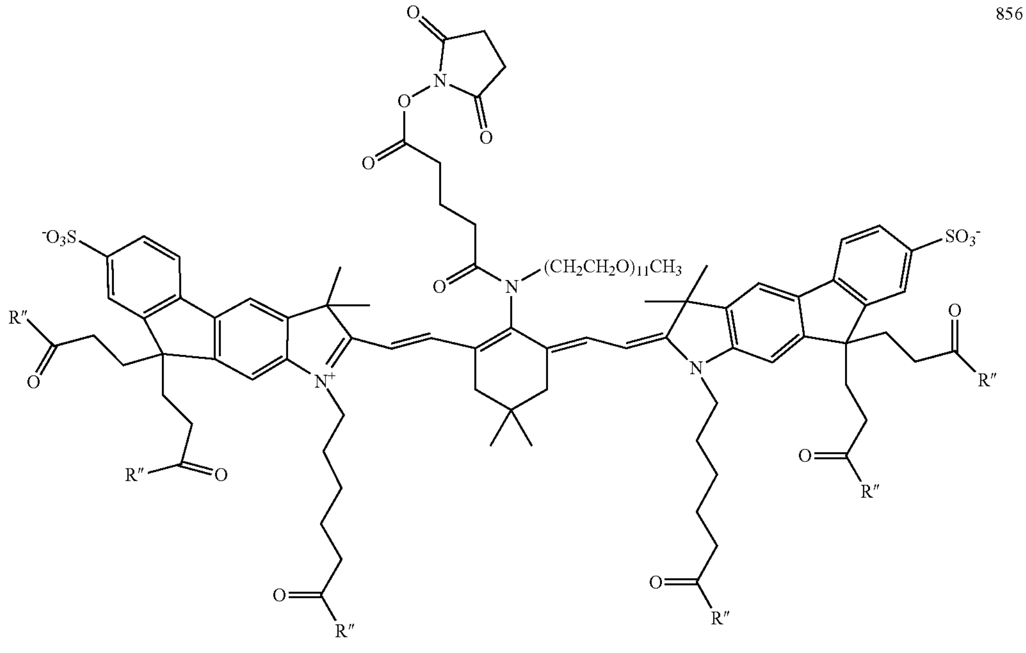 $R'' = NH(CH_2CH_2O)_6CH_3$ | 856 | 871 |
| E12 | 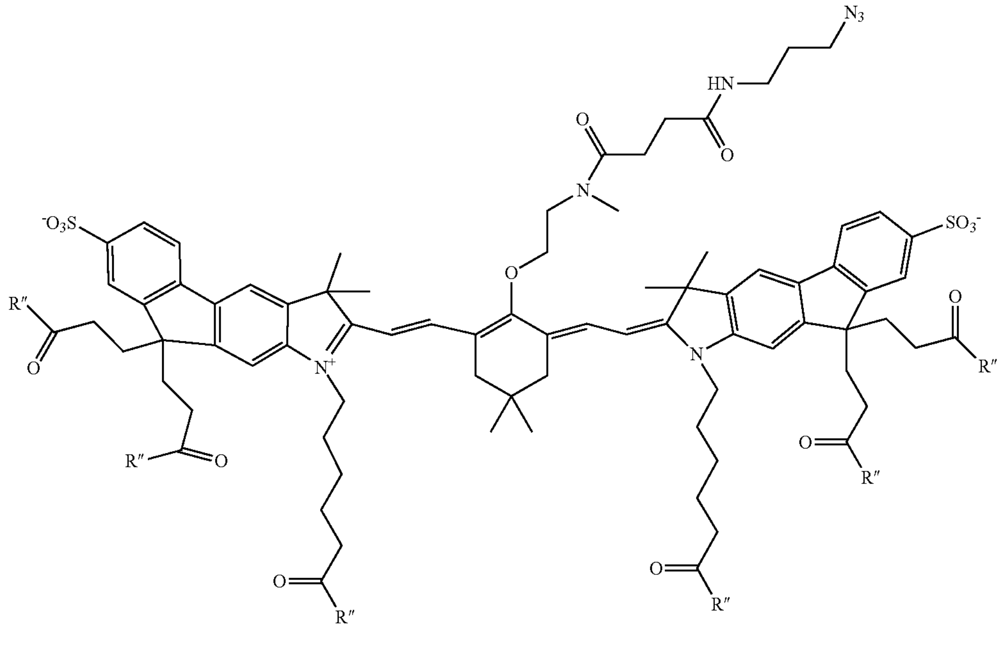 $R'' = NH(CH_2CH_2O)_4CH_3$ | 849 | 860 |

-continued
| No. | Structure | $\lambda^{ex}$ (nm) | $\lambda^{em}$ (nm) |
|---|---|---|---|
| E13 | 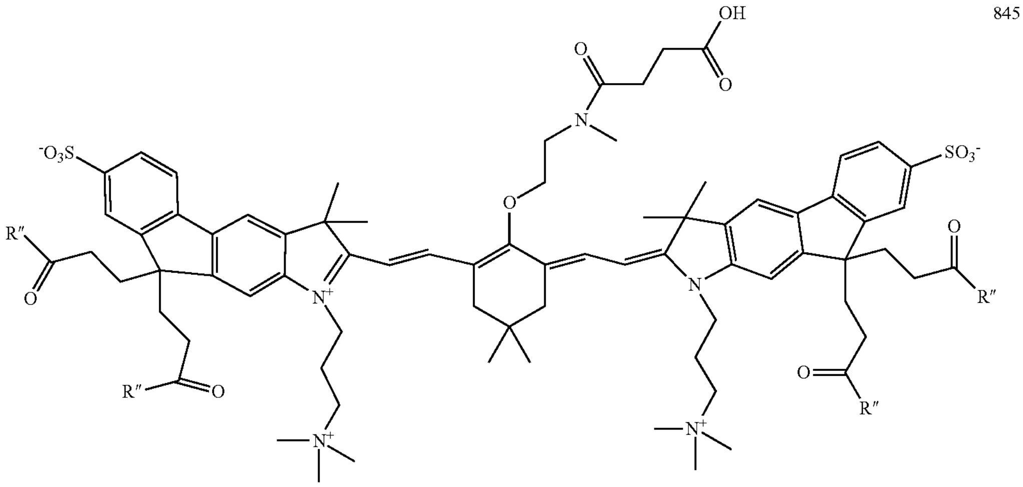 $R'' = NH(CH_2CH_2O)_{11}CH_3$ | 845 | 856 |
| E14 | 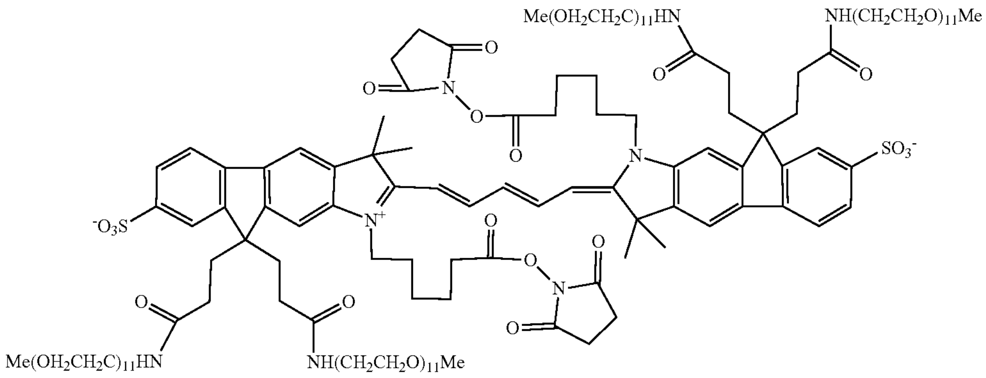 | 696 | 721 |
| E15 | 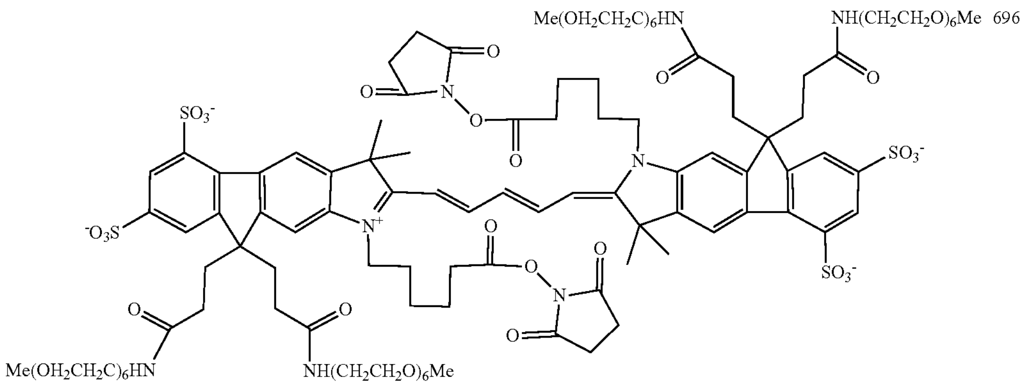 | 696 | 721 |

-continued
| No. | Structure | $\lambda^{ex}$ (nm) | $\lambda^{em}$ (nm) |
|---|---|---|---|
| E16 | 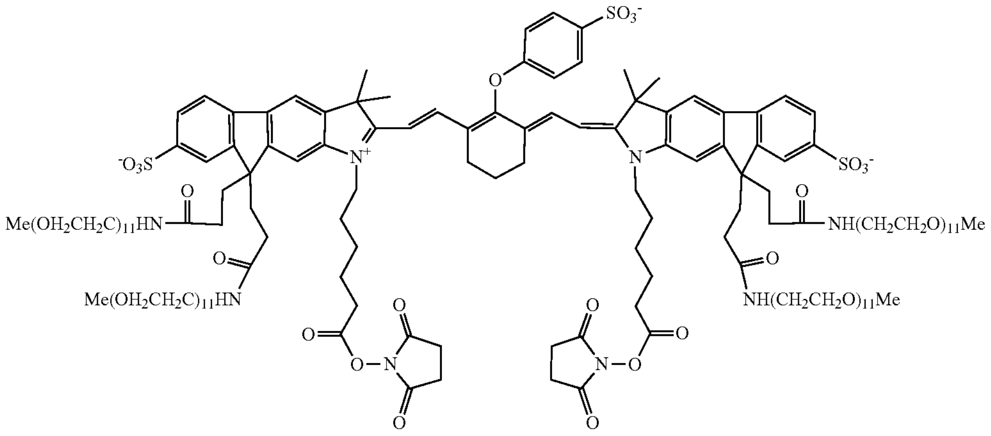 | 823 | 832 |
| E17 | 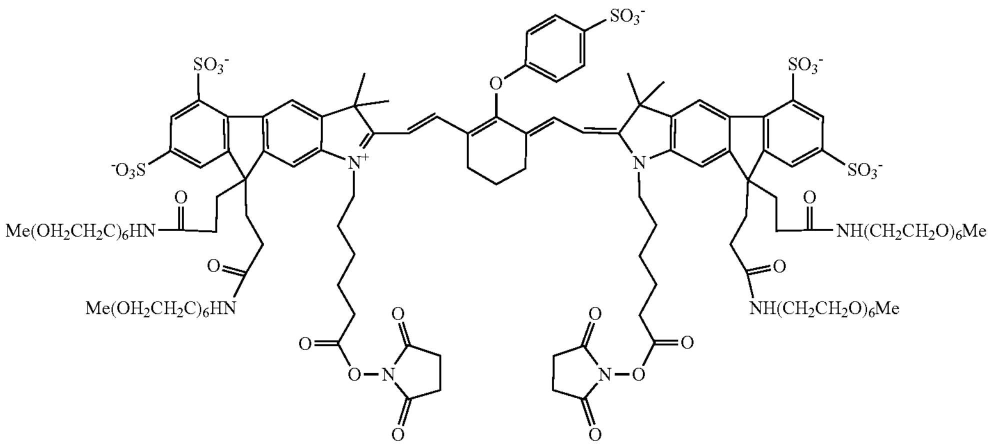 | 823 | 832 |
| E18 | 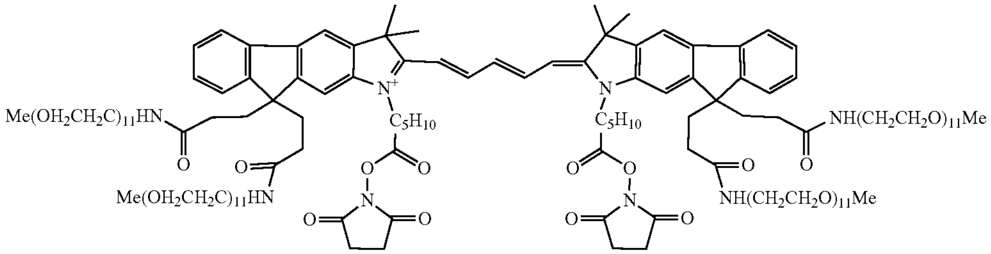 | 696 | 722 |
| E19 | 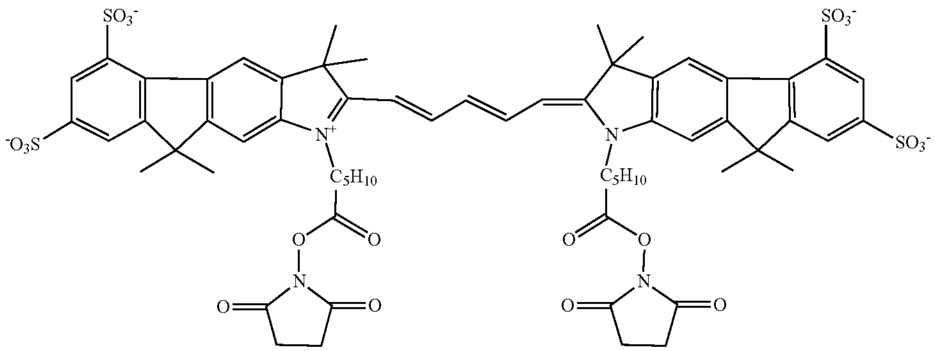 | 686 | 720 |

-continued
| No. | Structure | $\lambda^{ex}$ (nm) | $\lambda^{em}$ (nm) |
|---|---|---|---|
| E20 | 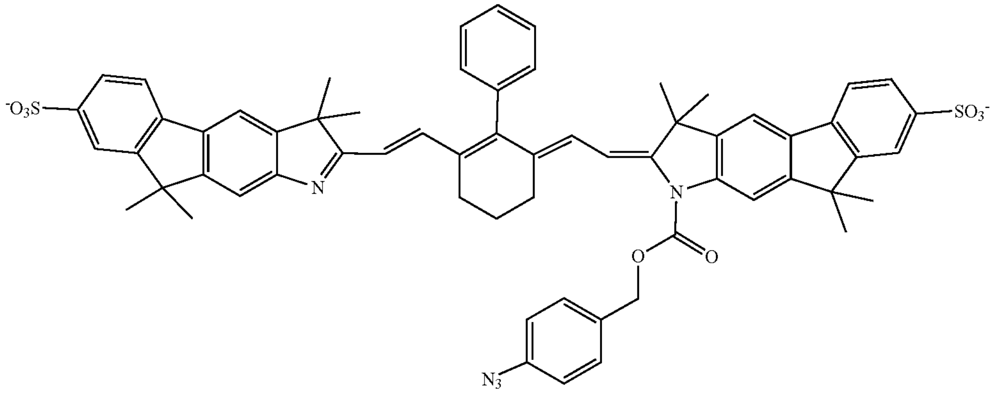 | | |
| E21 | 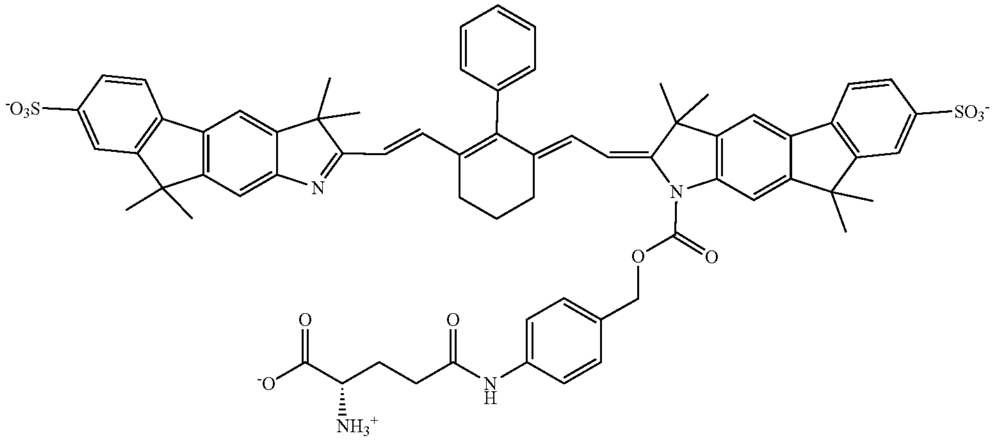 | | |
| E22 | 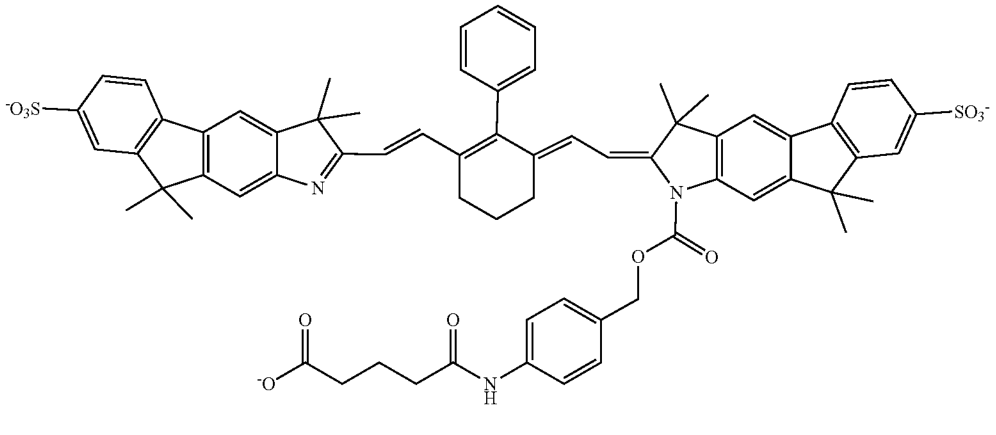 | | |

-continued

| No. | Structure | $\lambda^{ex}$ (nm) | $\lambda^{em}$ (nm) |
|---|---|---|---|
| E23 | 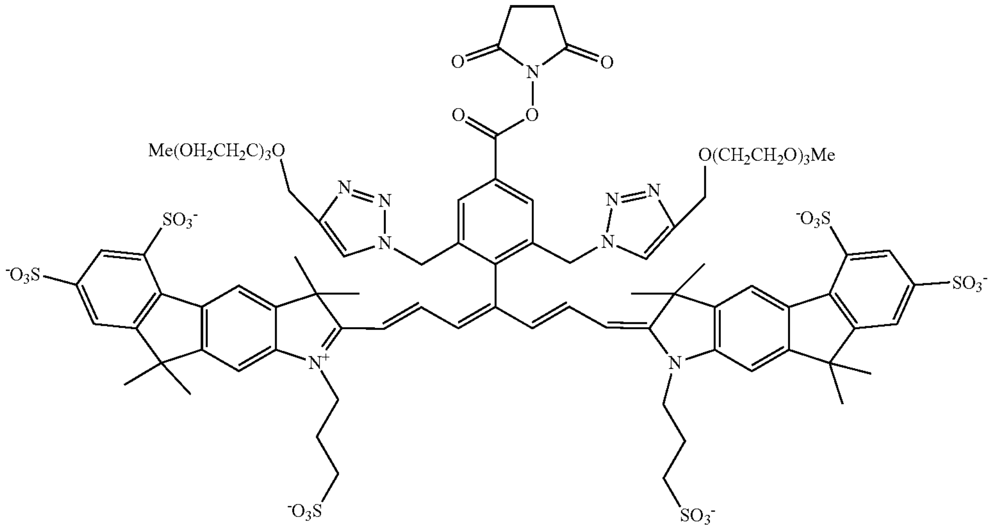 | 838 | 870 |

Synthesis of the Compounds of the Invention

In another aspect, the invention provides methods of synthesizing compounds of the invention.

Generally, the synthesis of compounds of the invention can proceed through the use of intermediates according to Formulas 3a or 3b:

Formula 3a

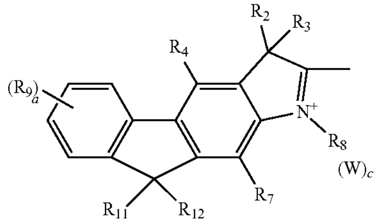

Formula 3b

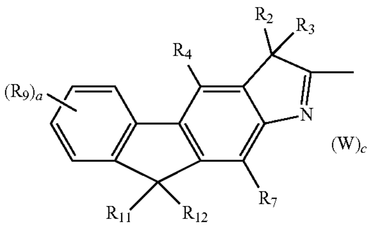

wherein the substituents are as defined above.

Such compounds are readily synthesized by methods analogous to Fischer indole synthesis (see Sundberg R J, THE CHEMISTRY OF INDOLES, Organic chemistry, a series of monographs, 1970, Academic Press). Additional procedures for preparing a variety of fluorescent cyanine dyes from the intermediates of Formula 3a and 3b are known to one of skill in the art, as exemplified e.g. in Hamer, The cyanine dyes and related compounds (John Wiley & Sons, New York 1964). Typical procedures for preparing fluorescent dyes comprising macrocyclic rings are described in U.S. Pat. Nos. 5,981,747; 5,986,093; 6,207,464; 6,277,984; and 7,465,810.

(1) Uses of the Subject Compounds.

The subject compounds find use in a variety of different applications. One application of interest is the use of the subject compounds comprising a reactive group as labeling agents which are capable of imparting a fluorescent property to a particular composition of matter. The compounds of the present invention comprising a reactive group R can be used to react with any of a broad range of molecules, including but not limited to, biomolecules such as polypeptides, polypeptide-based toxins, amino acids, nucleotides, polynucleotides including DNA and RNA, lipids, and carbohydrates, or a combination thereof. Additionally, the compounds of the invention comprising a reactive group R can be used to react with haptens, drugs, ion-complexing agents such as metal chelators, microparticles, synthetic or natural polymers, cells, viruses, other fluorescent molecules including the dye molecule according to the invention, or surfaces. The substrate molecules (i.e., the molecules to be covalently labeled) typically comprise one or more functional groups, which react with the reactive group of the subject compounds to form covalent or linkage. In one aspect, the reactive group of a compound of the invention is an activated ester (such as a succinimidyl ester, or SE), a maleimide, a hydrazide or an aminooxy group. Accordingly, in some aspects, functional group from a substrate molecule is an amine, a thiol, an aldehyde or ketone. The resulting fluorescently labeled substrate molecules may be referred to as conjugates or labeled substrate molecules. Any methods practiced in the art (e.g., Brinkley, Bioconjugate Chem. 3, 2(1992), incorporated herein by reference) for preparing fluorescent group-substrate conjugates are applicable for practicing the subject invention.

Conjugates of biomolecules and compounds of the invention usually have high fluorescence yield while typically retaining the critical parameters of unlabeled biomolecules, such as solubility, selective binding to a receptor or nucleic acid, activation or inhibition of a particular enzyme or the ability to incorporate into a biological membrane. Nevertheless, conjugates with the highest degree of labeling may still precipitate or bind nonspecifically. As necessary, a less-than-maximal degree of labeling may be acceptable in order to preserve function or binding specificity. Preparing the conjugates of the invention may involve experimentation to optimize properties. Following conjugation, unconjugated labeling reagent may be removed by techniques known in the art such as by gel filtration, dialysis, conjugate precipitation and resolubilization, HPLC or a combination of these techniques. The presence of free dye, particularly if it remains chemically reactive, may complicate subsequent experiments with the bioconjugate.

Compounds of the inventions can also be used to stain biological targets via physical interactions, such as hydrophobic interaction or electrostatic interaction or both, or via physical entrapment. In such cases, compounds of the invention are not required comprise a reactive group R.

In another embodiment, the subject compounds can be used to conjugate with a nucleoside, a nucleotide, or a polynucleotide, wherein any of such molecules may be natural or synthetic, modified or unmodified. The compound of the invention used for labeling may comprise a reactive group which is a phosphoramidite, an activated ester (such as a succinimidyl ester), an alkylating group or a reactive platinum complex. Such molecules may contain or are derivatized to contain one or more reaction partners for the reactive groups on the compounds of the invention. A reactive group of a compound of the invention may react with a suitable reaction partner on said molecule to form a covalent linkage. For example, a phosphoramidite group may react with a hydroxyl group to form a phosphate linkage after deprotection; a succinimidyl ester or the like may react with an amine group to form an amide linkage; and a reactive platinum complex may react with a guanosine base to form a platinum complex linkage. In one embodiment, a reactive compound of the invention comprising an activated ester is reacted with a nucleotide triphosphate comprising abase comprising an aminoalkynyl group, an aminoallyl group or an aminoalkyl group to form a fluorescently labeled nucleotide triphosphate. Such a labeled nucleotide triphosphate is often used to prepare a fluorescently labeled nucleic acid polymer via enzymatic incorporation.

In some embodiments, the fluorescent compound of the invention is reacted with a group or linker attached to the C-5 position of a uridine or cytidine residue. This position is not involved in Watson-Crick base-pairing and interferes little with hybridization to complementary sequences. An aminoalkynyl or aminoallyl linker may be introduced between a fluorescent moiety and the nucleotide in order to reduce fluorophore interaction with enzymes or target binding sites. In addition to this four-atom bridge, seven- to 10-atom spacers may be introduced that further separate the fluorophore from the base. The use of longer spacers may result in brighter conjugates and increased hapten accessibility for secondary detection reagents.

Alternatively, deoxycytidine triphosphates may be prepared which are modified at the N-4 position of cytosine using a 2-aminoethoxyethyl (OBEA) linker. Possible steric interference caused by the presence of the fluorescent fluorophore may be reduced by the use of additional spacers.

Fluorescently labeled DNA may be prepared from a fluorescently labeled nucleotide triphosphate by PCR reaction, terminal transferase-catalyzed addition or nick translation. Various polymerases may be used in such reactions. Such polymerases include Taq polymerase (useful e.g. in polymerase chain reaction (PCR) assays), DNA polymerase I (useful e.g. in nick-translation and primer-extension assays), Klenow polymerase (useful e.g. in random-primer labeling), Terminal deoxynucleotidyl transferase (TdT) (useful e.g. for 3'-end labeling), Reverse transcriptase (e.g. for synthesizing DNA from RNA templates) or other polymerases such as SP6 RNA polymerase, T3 RNA polymerase and T7 RNA polymerase for in vitro transcription.

Alternatively, a fluorescently labeled nucleic acid polymer may be prepared by first enzymatically incorporating an amine-labeled nucleotide into a nucleic acid polymer to result in an amine-labeled nucleic acid polymer, followed by the labeling of said amine-labeled polymer with a compound of the invention. More information on the preparation and use of fluorescently labeled nucleotide triphosphates can be found in U.S. Pat. Nos. 4,711,955 and 5,047,519. Still alternatively, a nucleic acid polymer, such as a DNA, may be directly labeled with a compound of the invention comprising a reactive platinum complex as the reactive group, wherein the platinum complex forms a coordinative bond with a nitrogen atom of a guanosine base such as described in U.S. Pat. No. 5,714,327.

In another embodiment, the subject compounds can be used to conjugate with an aminoacid, aminoacid analog or a polypeptide. Labeled aminoacids, aminoacid analogs and polypeptides may be labeled by reacting the compounds of the invention with aminoacids, aminoacid analogs and polypeptides comprising reaction partners for the reactive groups on said compounds. Such reaction partners may be natural or unnatural groups present in said polypeptides. By way of example, reaction partners may be the natural residues such as amino groups, which are part of natural lysine residues, or thiol groups, which are part of natural cysteine groups.

In order to achieve the maximal fluorescence possible, a protein may be labeled with as many molecules of the same fluorescent group as possible, to the degree that the biological activity of the protein is minimally affected by the labeling. In other cases it may be desirable to avoid fluorescence quenching resulting from multiple fluorescent group molecules on the protein interacting with each other. Dye-dye interactions may be physical, such as dye aggregation, or may be a spectral, such as FRET-based energy transfer, or a combination of both. Either type of interaction may lead to fluorescence quenching, which can be characterized by a slow rise and then a rapid drop of the total fluorescence of the labeled protein as the degree of labeling increases.

Certain compounds of the invention can also stain cellular targets via non-covalent labeling, such as via hydrophobic interaction with cell membranes. Compounds of the invention that are capable of acting as cell membrane stains, particularly mitochondrial membrane stains, generally have an overall positive charge.

Compounds of the invention can also be used to stain aqueous cellular compartments via physical trapping or confinement by the cellular membranes. Suitable dyes for this application generally have at least two negative charges, making the dyes highly polar and water-soluble. This type of fluorescent dyes is typically referred to as fluorescent polar tracers for tracing the morphology of cells, such as neurons, or for tracing cell lineage as cells divide and differentiate. Because this type of dyes are generally small in size, highly water soluble and nontoxic, they can rapidly diffuse into the entire cell cytoplasm, making it possible for one to visualize the morphology of one single cell or a few selected cells in a complex environment, such as in a tissue. For example, fluorescent polar tracers enable one to visualize the fine structures of dendrites and axon of a neuron and its interaction with another neighboring neuron in a cell culture or tissue. A polar tracer is usually introduced into cells via microinjection or other suitable techniques. One of the early generation of fluorescent polar tracers is Lucifer Yellow (Stewart, W W, Nature 292, 17(1981)). More recently, Alexa Fluor 488 hydrazide (available from Invitrogen Co., cat #10436) and CF647 hydrazide (available from Biotium, Inc. cat #92136).

(2) Uses of Covalently Labeled Biomolecules of the Invention

The subject compounds provide an effective tool for labeling biomolecules for a wide variety of applications. Labeling allows one to discern interactions involving biomolecules such as proteins, glycoproteins, nucleic acids, and lipids, as well as inorganic chemicals, or any combinations thereof. The interactions may be between nucleic acid molecules, between nucleic acid and protein, and between protein and small molecules. The interactions may be discerned in a cell-free biological system, in a cellular system (including intracellular and extracellular systems), or in vivo, which encompasses activities within a cell that is within a tissue or organ or a subject. Delineating the various interactions is often a significant step in scientific research and development, drug design, screening and optimization, phylogenetic classification, genotyping individuals, parental and forensic identification, environmental studies, diagnosis, prognosis, and/or treatment of disease conditions.

Biomolecules labeled according to the methods of the invention may be used as binding agents to detect their binding partners, the targets of their biological interaction, as described above. For example, a protein can be labeled with a dye of the invention and used to bind to a cell surface receptor. In some embodiments of the invention, a binding agent is labeled with a substituted cyanine dye having maximal fluorescence excitation wavelength of equal or greater than 660 nm, a water soluble group, and a reactive group under conditions effective to crosslink the dye and the binding agent. In some embodiments, the substituted cyanine dye is substituted by a non-spiro substituent. A binding agent so labeled is contacted with its binding partner, and the fluorescent label is detected. In other embodiments, a binding agent is reacted with a compound of the invention under conditions effective to crosslink the compound with the binding agent.

Labeled molecules of the invention may be used as part of FRET pairs in a variety of biological assays and methods, whether as donor or acceptor molecules. A person skilled in the art will know to select a suitable FRET partner based on the specific application. Such applications include, but are not limited to, assays involving molecular beacons, FRET protease assays, flow cytometry, nucleic acid hybridization and any other applications where the relative spatial localization of two or more moieties must be probed. FRET is generally useful on scales of 10 to 100 Å. In one embodiment, both the donor and the acceptor of a FRET pair are labeled molecules of the invention. In another embodiment, one member of a FRET pair is a labeled oligonucleotide of the invention which is capable of annealing to a complementary oligonucleotide labeled with a second member of the FRET pair, such that annealing leads to an increase in the efficiency of energy transfer. In this example, the second member of the FRET pair may be a fluorophore of the invention or may be a different fluorophore.

In some applications, it is desirable to quench the labeled molecules of the invention. A variety of quenchers known in the art may be used. Non-limiting examples include Black Hole Quencher™ moieties, DABCYL, Reactive Red 4 (Cibacron Brilliant Red 3B-A), Malachite Green, 4-Dimethylaminophenylazophenyl-4'-isothiocyanate (DABITC), and 4,4'-Diisothiocyanaitodihydro-stilbene-2,2'-disulfonic acid. By way of example, a molecular beacon may be labeled with a compound of the invention as well as with a suitable quencher. In the closed conformation of the beacon, the fluorophore is quenched. When the beacon opens as a result of a recognition or binding event, the fluorescence of the fluorophore increases significantly.

In still another embodiment, the invention provides an energy transfer fluorescent group comprising a first donor fluorescent group and second acceptor fluorescent group wherein: the donor fluorescent group and acceptor fluorescent group are covalently linked to form a FRET pair; at least one of the donor fluorescent group and acceptor fluorescent group is a fluorescent group of the invention; and the energy transfer fluorescent group optionally comprises a reactive group. Methods for preparing energy transfer fluorescent groups and uses thereof have been previously described. See U.S. Pat. No. 6,479,303 and WO 00/13026.

In one embodiment, a fluorescent group of the invention is used to label a fluorescent protein to form a so-called tandem dye, wherein the fluorescent group of the invention and the fluorophore of the fluorescent protein form an energy transfer pair (i.e., FRET pair). In such a FRET pair, the fluorescent group of the invention is either the donor fluorescent group or the acceptor fluorescent group and, likewise, the fluorophore of the protein is either the acceptor fluorescent group or the donor fluorescent group, such that the FRET pair can be excited at or near the absorption maxima of the donor fluorescent group and the fluorescence collected at the emission maxima of the acceptor fluorescent group, resulting in a large Stokes shift. Suitable fluorescent proteins for preparing tandem dyes include, but are not limited to, various phycobiliproteins such as Allophycocyanin B, Allophycocyanin (APC), C-Phycocyanin, R-Phycocyanin, Phycoerythrocyanin, C-Phycoerythrin, b-Phycoerythrin, B-Phycoerythrin, R-Phycoerythrin (R-PE), and the likes. Phycobiliproteins are proteins comprising bilin as prosthetic groups, which are also the fluorophores of the proteins. Preferably, the phycobiliproteins are R-PE or APC. To achieve suitable FRET efficiency, one may choose a fluorescent group of proper wavelengths so that the emission of the donor fluorescent group and the absorption of the acceptor fluorescent group have sufficient spectral overlap. Detailed methods for fluorescent group selection and for preparing tandem dyes are disclosed in U.S. Pat. Nos. 4,520,110 and 5,714,386. Because of their large Stokes shift, tandem dyes of the invention may be useful for multi-color detections where only a limited number of excitation light sources may be available. In particular, tandem dyes of the invention may be useful for fluorescence-activated cell sorting (FACS) or flow cytometry studies. Commercial flow cytometers are typically equipped with 1 to 3 excitation light sources, more commonly 1 to 2 excitation light sources. For example, some of the commercial flow cytometers are equipped with a 488 nm argon laser and a 633 nm He—Ne laser or a 635 nm red diode laser, and a significant number of flow cytometers have only the 488 nm argon laser. Thus, in order to detect multiple targets, each target may be stained with a different fluorescent group having a different emission and the different fluorescent groups all need to be efficiently excited by a common excitation source. Tandem dyes of the invention can fill this need as different tandem dyes having the same excitation maxima but different emission maxima can be readily prepared.

In one embodiment, a compound of the invention is applied to a biological sample comprising a plurality of polypeptides and optionally other biological molecules under a condition facilitating the covalent labeling of said polypeptides. In some embodiments, the reactive group of the compound is an activated ester, a maleimide, an iodoacetamide, a bromoacetamide, a hydrazide, an amine or an aminooxy group. The biological sample may be a cell lysate or a tissue lysate. The resulting labeled polypeptides or cellular components may be analyzed and/or purified by any of a variety of known tools or techniques, including, but not limited to, protein microarrays, chromatography and gel electrophoresis.

The present invention also provides kits comprising compounds of the invention and/or fluorescent group-substrate conjugates of the invention for various assays as selectively described above. A kit of the invention may comprise one or more compounds of the invention and instructions instructing the use of said compound. For example, a kit may comprise one or more compounds of the invention for labeling a substrate, one or more buffers for the labeling reaction and product purification, a chromatography column for purifying the resulting fluorescent group-substrate conjugate, a protocol for carrying out the procedure, optionally any additional reagents and optionally any reference standard. In another embodiment, a kit comprises one or more fluorescent group-substrate conjugates of the invention, one or more buffers, a protocol for the use of said conjugate(s), optionally any other reagents for an assay, and optionally any calibration standard(s). The kit may further contain other materials or devices of use in purifying the conjugation products.

The signals produced by the fluorescent groups of the invention may be detected in a variety of ways. Generally, a change of signal intensity can be detected by any methods known in the art and is generally dependent on the choice of fluorescent group used. It can be performed with the aid of an optical system. Such system typically comprises at least two elements, namely an excitation source and a photon detector. Numerous examples of these elements are available in the art. An exemplary excitation source is a laser, such as a polarized laser. The choice of laser light will depend on the fluorescent group attached to the probe. For most of the fluorescent groups, the required excitation light is within the range of about 300 nm to about 1200 nm, or more commonly from about 350 nm to about 900 nm. Alternatively, compounds of the invention may be excited using an excitation wavelength of about 300 to about 350 nm, 350 to 400 nm, 400 to 450 nm, 450 to 500 nm, 500 to 550 nm, 550 to 600 nm, 600 to 650 nm, 650 to 700 nm, 750 nm to 800 nm, or from 800 nm to 850 nm, merely by way of example. Those skilled in the art can readily ascertain the appropriate excitation wavelength to excite a given fluorophore by routine experimentation (see e.g., The Handbook—'A Guide to Fluorescent Probes and Labeling Technologies, Tenth Edition' (2005) (available from Invitrogen, Inc./Molecular Probes) previously incorporated herein by reference). Where desired, one can employ other optical systems. These optical systems may comprise elements such as optical reader, high-efficiency photon detection system, photo multiplier tube, gate sensitive FET's, nano-tube FET's, photodiode (e.g. avalanche photo diodes (APD)), camera, charge couple device (CCD), electron-multiplying charge-coupled device (EMCCD), intensified charge coupled device (ICCD), and confocal microscope. These optical systems may also comprise optical transmission elements such as optic fibers, optical switches, mirrors, lenses (including microlens and nanolens), collimators. Other examples include optical attenuators, polarization filters (e.g., dichroic filter), wavelength filters (low-pass, band-pass, or high-pass), wave-plates, and delay lines. In some embodiments, the optical transmission element can be planar waveguides in optical communication with the arrayed optical confinements. See, e.g., U.S. Pat. Nos. 7,292,742, 7,181,122, 7,013,054, 6,917,726, 7,267,673, and 7,170,050. These and other optical components known in the art can be combined and assembled in a variety of ways to effect detection of distinguishable signals.

Fluorescently labeled polynucleotides of the invention find use in a variety of applications. Such applications can involve interactions between nucleic acids, e.g., interactions between DNA and DNA, DNA and RNA, and RNA and RNA, or any other non-naturally occurring nucleic acids PNA, LNA, and/or TNA. Various applications can also involve interactions between nucleic acids and proteins, lipids or combinations thereof. Non-limiting examples of specific nucleic acid assays include nucleic acid amplification, both quantitative or end-point amplification, hybridization in solution or on a substrate (e.g., array hybridization), gel shifts, and nucleic acid sequencing. The fluorescently labeled polynucleotides can be used in solution phase or immobilized on a substrate.

In one embodiment, the labeled polynucleotides are used as hybridization probes. One application of hybridization probes is fluorescent in situ hybridization (FISH). In this technique, a labeled polynucleotide complementary to a sequence of interest is annealed to fixed chromosomes preparations, and the presence of the sequence of interest as well as the chromosomal localization is detected by microscopy. FISH can be performed by immobilizing the nucleic acids of interest on a substrate including without limitation glass, silicon, or fiber. FISH may also be used quantitatively (Q-FISH) to detect the presence and length of repetitive sequences such as telomeres. This may be done by quantitating the intensity of emitted fluorescence as measured by microscopy. FISH assays utilizing the subject fluorescent compounds can be performed for detecting a specific segment of a DNA molecule or a chromosome. These features can be used in genetic counseling (e.g., prenatal-screens), medicine, and species identification.

In some embodiments, labeled polynucleotides can be used as primers in amplification reactions such as PCR. In yet another embodiment, a compound of the invention may be used to label a polynucleotide which is subsequently used as a probe may be a hybridization probe or a real-time PCR probe. Such a probe may be labeled with a second fluorescent group to form a FRET pair with the first fluorescent group of the invention. Methods for the preparation and use of PCR probes are well known to one skilled in the art.

In one embodiment of the invention, a method is provided for detecting or quantifying a target nucleic acid, the method comprising the steps of: a) providing a labeled polynucleotide ("probe") of the present invention; b) contacting said labeled polynucleotide with the nucleic acid target so as to allow for hybridization of the probe with the nucleic acid target; and c) detecting or quantifying said nucleic acid target by measuring a change in the fluorescence of the probe upon the hybridization of the nucleic acid probe with the nucleic acid target.

As used herein, hybridization occurs when the probe forms a complex with the target nucleic acid. In general, the complex is stabilized, at least in part, via hydrogen bonding between the bases of the nucleotide residues. The hydrogen bonding may occur by Watson-Crick base pairing, Hoogstein binding, or in any other sequence-specific manner. Hybridization may constitute a step in a more extensive process, such as the initiation of a PCR reaction, or the enzymatic cleavage of a polynucleotide by a ribozyme.

After hybridization between the probe and the target has occurred, a change in the intensity of the fluorescence of the probe may be measured. Such change before and after hybridization can yield a positive gain or negative reduction in the detected signal intensity. Depending on the specific hybridization assay that is run, more than one event after hybridization may contribute to the generation of a change in signal intensity. For example, an increase in reporter signal may result by way of spatial extension or separation of the reporter fluorescent group from the quencher group while both are still attached to the probe. In addition, either the reporter or the quencher of the probe can be separated by way of cleavage via an enzyme (e.g., a polymerase having a 5' to 3' exonuclease), thereby generating a reporter signal that is detected. As noted above, both the reporter and the quencher are defined in functional terms, such that these groups can be identical though serving, relative to each other, a different function when used in a hybridization reaction. For example, a group attached to a probe is a quencher because it reduces the emission of an optical signal when the probe is not hybridized with the target nucleic acid (typically when the probe assumes a random state). The same group can become a reporter fluorescent group upon being cleaved by an enzyme after hybridization with the target nucleic acid as the signal of the fluorescent group is now detected during the assay.

The signal detection methods described previously can be applied to nucleic acid amplification in which the target nucleic acid is increased in copy number. Such increase may occur in a linear or in an exponential manner. Amplification may be carried out by natural or recombinant DNA polymerases such as Taq polymerase, Pfu polymerase, T7 DNA polymerase, Klenow fragment of *E. coli* DNA polymerase, Tma DNA polymerase, exo-Tli DNA polymerase, exo-KOD DNA polymerase, exo-JDF-3 DNA polymerase, exo-PGB-D DNA polymerase, UITma (N-truncated) Thermatoga martima DNA polymerase, Sequenase, and/or RNA polymerases such as reverse transcriptase.

A preferred amplification method is polymerase chain reaction (PCR). General procedures for PCR are taught in U.S. Pat. No. 4,683,195 (Mullis) and 4,683,202 (Mullis et al.). Briefly, amplification of nucleic acids by PCR involves repeated cycles of heat-denaturing the DNA, annealing two primers to sequences that flank the target nucleic acid segment to be amplified, and extending the annealed primers with a polymerase. The primers hybridize to opposite strands of the target nucleic acid and are oriented so that the synthesis by the polymerase proceeds across the segment between the primers, effectively doubling the amount of the target segment. Moreover, because the extension products are also complementary to and capable of binding primers, each successive cycle essentially doubles the amount of target nucleic acids synthesized in the previous cycle. This results in exponential accumulation of the specific target nucleic acids at approximately a rate of $2^n$, where n is the number of cycles.

A typical conventional PCR thermal cycling protocol comprises 30 cycles of (a) denaturation at a range of 90° C. to 95° C. for 0.5 to 1 minute, (b) annealing at a temperature ranging from 50° C. to 65° C. for 1 to 2 minutes, and (c) extension at 68° C. to 75° C. for at least 1 minute. Other protocols including but not limited to universal protocol as well as fast cycling protocol can be performed the subject probes as well.

A variant of the conventional PCR is a reaction termed "Hot Start PCR". Hot Start PCR techniques focus on the inhibition of polymerase activity during reaction preparation. By limiting polymerase activity prior to PCR cycling, non-specific amplification is reduced and the target yield is increased. Common methods for Hot Start PCR include chemical modifications to the polymerase (see, e.g., U.S. Pat. No. 5,773,258), inhibition of the polymerase by a polymerase-specific antibody (see, e.g., U.S. Pat. No. 5,338,671), and introduction of physical barriers in the reaction site to sequester the polymerase before the thermal cycling takes place (e.g., wax-barrier methods). The reagents necessary for performing Hot Start PCR are conveniently packaged in kits that are commercially available (see, e.g., Sigma's JumpStart Kit).

Another variation of the conventional PCR that can be performed with the subject probes is "nested PCR" using nested primers. The method is preferred when the amount of target nucleic acid in a sample is extremely limited for example, where archival, forensic samples are used. In performing nested PCR, the nucleic acid is first amplified with an outer set of primers capable of hybridizing to the sequences flanking a larger segment of the target nucleic acid. This amplification reaction is followed by a second round of amplification cycles using an inner set of primers that hybridizes to target sequences within the large segment.

The subject probes can be employed in reverse transcription PCR reaction (RT-PCR), in which a reverse transcriptase first converts RNA molecules to double stranded cDNA molecules, which are then employed as the template for subsequent amplification in the polymerase chain reaction. In carrying out RT-PCR, the reverse transcriptase is generally added to the reaction sample after the target nucleic acids are heat denatured. The reaction is then maintained at a suitable temperature (e.g., 30° C.-45° C.) for a sufficient amount of time (e.g., 5-60 minutes) to generate the cDNA template before the scheduled cycles of amplification take place. Such reaction is particularly useful for detecting the biological entity whose genetic information is stored in RNA molecules. Non-limiting examples of this category of biological entities include RNA viruses such as HIV and hepatitis-causing viruses. Another important application of RT-PCR embodied by the present invention is the simultaneous quantification of biological entities based on the mRNA level detected in the test sample.

The subject probes can also be employed to perform ligase chain polymerase chain reaction (LCR-PCR). The method involves ligating the target nucleic acids to a set of primer pairs, each having a target-specific portion and a short anchor sequence unrelated to the target sequences. A second set of primers containing the anchor sequence is then used to amplify the target sequences linked with the first set of primers. Procedures for conducting LCR-PCR are well known to artisans in the field, and hence are not detailed herein (see, e.g., U.S. Pat. No. 5,494,810).

The subject probes can be used to detect single mutations. Accordingly, methods are provided to use the probes of the invention to detect as few as a single mismatch between the probe sequence and a target sequence. Such high specificity in nucleic acid detection by PCR is highly valuable in clinical diagnosis and genetic research. For example, many diseases are associated with single mutations at different sites in the human genome. Although in theory this type of genetic variations, also called single nucleotide polymorphism or SNP, may be detected by sequencing, such sequencing method is not expected to be practical on a large scale due to high cost and low efficiency. Detection of SNP by an amplification reaction is feasible with the use of the subject probes.

The subject probes are also suited for monitoring nucleic acid amplification reactions. In a related embodiment, the present invention provides a method of monitoring the increase in a target nucleic acid during amplification of said target. The method typically involves a) providing an amplification reaction mixture that comprises said target nucleic acid, at least one primer that hybridizes to the target nucleic acid, a labeled oligonucleotide probe of the present invention that provides a detectable signal, the intensity of which is proportional to the increase in the target nucleic acid in the amplification; (b) treating said mixture under conditions for amplifying said target nucleic acid; and (c) measuring the amount of said signal produced by said mixture during said treating step (c). Where desired, the amount of signal is determined continuously throughout the amplification reaction or determined intermittently during the amplification reaction. The amplification can be exponentially with the use of a primer pair or linearly with the use of one primer of the pair.

The increase in signal intensity during the amplification reaction may due to the step of hybridization of the probe to the target nucleic acid and also the step of cleavage via the action of the polymerase utilized in the amplification reaction.

In one aspect, the subject methods exploit the 5' to 3' nuclease activity of a polymerase when used in conjunction with PCR. When the subject probe is added concomitantly with the primer at the start of PCR, and the signal generated from hydrolysis of the labeled nucleotide(s) of the probe provides a means for detection of the target sequence during its amplification. Numerous polymerases are suited to catalyze primer and template-dependent nucleic acid synthesis and possess the 5' to 3' nuclease activity. Non-limiting examples include DNA polymerases such as *E. coli* DNA polymerase I, *Thermus thermophilus* (Tth) DNA polymerase, *Bacillus stearothermophilus* DNA polymerase, *Thermococcus littoralis* DNA polymerase, and *Thermus aquaticus* (Taq) DNA polymerase. Where desired, temperature stable polymerases can be employed in a nucleic acid amplification reaction. See, e.g., U.S. Pat. No. 4,889,818 that discloses a representative thermostable enzyme isolated from *Thermus aquaticus*. Additional representative temperature stable polymerases include without limitation, e.g., polymerases extracted from the thermostable bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima, Thermococcus littoralis*, and *Methanothermus fervidus*.

In another embodiment, nucleic acid amplification can be performed with polymerases that exhibit strand-displacement activity (also known as rolling circle polymerization). Strand displacement can result in the synthesis of tandem copies of a circular DNA template, and is particularly useful in isothermal PCR reaction. Non-limiting examples of rolling circle polymerases suitable for the present invention include but are not limited to T5 DNA polymerase (Chatterjee et al., Gene 97:13-19 (1991)), and T4 DNA polymerase holoenzyme (Kaboord and Benkovic, Curr. Biol. 5:149-157 (1995)), phage M2 DNA polymerase (Matsumoto et al., Gene 84:247 (1989)), phage PRD1 DNA polymerase (Jung et al., Proc. Natl. Aced. Sci. USA 84:8287 (1987), and Zhu and Ito, Biochim. Biophys. Acta. 1219:267-276 (1994)), Klenow fragment of DNA polymerase I (Jacobsen et al., Eur. J. Biochem. 45:623-627 (1974)).

A preferred class of rolling circle polymerases utilizes protein priming as a way of initiating replication. Exemplary polymerases of this class are modified and unmodified DNA polymerase, chosen or derived from the phages Φ29, PRD1, Cp-1, Cp-5, Cp-7, Φ15, Φ1, Φ21, Φ25, BS 32 L17, PZE, PZA, Nf, M2Y (or M2), PR4, PR5, PR722, B103, SF5, GA-1, and related members of the Podoviridae family. Specifically, the wildtype bacteriophage Φ29 genome consists of a linear double-stranded DNA (dsDNA) of 19,285 base pairs, having a terminal protein (TP) covalently linked to each 5'end. To initiate replication, a histone-like viral protein forms a nucleoprotein complex with the origins of replication that likely contributes to the unwinding of the double helix at both DNA ends (Serrano et al., The EMBO Journal 16(9): 2519-2527 (1997)). The DNA polymerase catalyses the addition of the first dAMP to the hydroxyl group provided by the TP. This protein-primed event occurs opposite to the second 3' nucleotide of the template, and the initiation product (TP-dAMP) slides back one position in the DNA to recover the terminal nucleotide After initiation, the same DNA polymerase replicates one of the DNA strands while displacing the other. The high processivity and strand displacement ability of Φ29 DNA polymerase makes it possible to complete replication of the Φ29 TP-containing genome (TP-DNA) in the absence of any helicase or accessory processivity factors (reviewed by Serrano et al., The EMBO Journal 16(9): 2519-2527 (1997)).

Strand displacement can be enhanced through the use of a variety of accessory proteins. They include but are not limited to helicases (Siegel et al., J. BioL Chem. 267:13629-13635 (1992)), herpes simplex viral protein ICP8 (Skaliter and Lehman, Proc. Natl, Acad. Sci. USA 91(22):10665-10669 (1994)), single-stranded DNA binding proteins (Rigler and Romano, J. Biol. Chem. 270:8910-8919 (1995)), adenovirus DNA-binding protein (Zijderveld and van der Vliet, J. Virology 68(2):1158-1164 (1994)), and BMRF1 polymerase accessory subunit (Tsurumi et al., J. Virology 67(12):7648-7653 (1993)).

The subject probes can be utilized in an isothermal amplification reaction. Such amplification reaction does not rely solely upon thermal cycling. The procedure can be applied at a wide range of ambient temperatures. In particular, denaturation of the double-stranded template sequence is not accomplished solely through an increase in temperature above the melting temperature of the double stranded sequence. Rather, the denaturation process involves physical or mechanical force that separates the strand to allow primer annealing and extension. Various mechanisms for conducting isothermal amplification reaction including isothermal PCR are described in US. Patent Publication No 20060019274 and U.S. Pat. Nos. 5,824,477 and 6,033,850, which are incorporated herein by reference.

Nucleic acid amplification is generally performed with the use of amplification reagents. Amplification reagents typically include enzymes, aqueous buffers, salts, primers, target nucleic acid, and nucleoside triphosphates. Depending upon the context, amplification reagents can be either a complete or incomplete amplification reaction mixture.

The choice of primers for use in nucleic acid amplification will depend on the target nucleic acid sequence. Primers used in the present invention are generally oligonucleotides, e.g., 10 to 100 or 10 to 25 bases in length, that can be extended in a template-specific manner via the action of a polymerase. In general, the following factors are considered in primer design: a) each individual primer of a pair preferably does not self-hybridize in an amplification reaction; b) the individual pairs preferably do not cross-hybridize in an amplification reaction; and c) the selected pair must have the appropriate length and sequence homology in order to anneal to two distinct regions flanking the nucleic acid segment to be amplified. However, not every nucleotide of the primer must anneal to the template for extension to occur. The primer sequence need not reflect the exact sequence of the target nucleic acid. For example, a non-complementary nucleotide fragment may be attached to the 5' end of the primer with the remainder of the primer sequence being complementary to the target. Alternatively, non-complementary bases can be interspersed into the primer, provided that the primer sequence has sufficient complementarily with the target for annealing to occur and allow synthesis of a complementary nucleic acid strand.

A nucleic acid amplification reaction typically comprises a target nucleic acid in a buffer compatible with the enzymes used to amplify the target. The buffer typically contains nucleotides or nucleotide analogs (ATP, TTP, CTP, GTP, or analogs thereof including without limitation pentaphosphates having the respective base unit) that are capable of being incorporated into a replica strand of the template sequence.

Where desired, amplification reaction is carried out as an automated process. Numerous thermocyclers are available in the art that are capable of holding 48, 96 or more samples. A suitable optical system moves the excitation light from the source to the reaction sites and measures the emission light from each sample. For example, multiple fiber optic leads simultaneously read all PCR tubes undergoing thermocycling. However, only a single fluorometer may be needed to read fluorescence from the reaction sites. An analogous detection scheme is suitable in a 96-well microtiter format. This type of format is frequently desirable in clinical laboratories for large scale sample screening, for example, for genetic analysis such as screening for AIDS virus in blood bank screening procedures.

Accordingly, the present invention also provides an apparatus for detecting the signal generated by the subject probe, which can be used to detect, measure, and quantify the signal before, during, and after amplification. The apparatus comprises a thermal unit (e.g., a thermocycler) capable of holding an amplification reaction mixture comprising the subject probes and effecting an amplification of the target sequence, and a detector that detects the signal generated from the subject probes.

In another embodiment of the present invention, the subject probes are employed in assays that are conducted on nucleic acid microarrays to detect or quantify nucleic acid targets. In such assays, a fluorescent signal is generated on a nucleic acid microarray upon the presence of a complementary target nucleic acid.

Nucleic acid microarrays including gene chips comprise ordered arrays of nucleic acids that are covalently attached to a solid surface, see e.g., U.S. Pat. Nos. 5,871,928, 6,040,193, 6,262,776, 6,403,320, and 6,576,424. The fluorescent signal that is generated in the assay can be monitored and quantified with optical detectors including but not limited to fluorescence imagers, e.g. commercial instruments supplied by Hitachi Corp., San Bruno, Calif. or confocal laser microscopes (confocal fluorescence scanners), e.g. commercial instruments from General Scanning, Inc., Watertown, Mass.

In assays that are conducted on nucleic acid microarrays, the target nucleic acids may be provided as a mixture of nucleic acid sequences derived from any suitable biological sources. They can be derived from body fluid, solid tissue samples, tissue cultures or cells derived therefrom and the progeny thereof, and sections or smears prepared from any of these sources, or any other samples that contain nucleic acids.

Where expression pattern is assayed, the mRNA sequences are first typically amplified by reverse transcription PCR with universal primers prior to their use as the target sequences in the assay. In one embodiment, all nucleic acid sequences present in the test sample are simultaneously applied to the microarray for analysis, thus allowing the interaction of all target nucleic acid sequences with all nucleic acids that are present on the array. In another embodiment, the target nucleic acids applied to the array are pre-selected to yield a subset for refined hybridization analysis utilizing a microarray. For example, a limited number of target sequences can contain more than one stretch of specific nucleotide sequence to be analyzed, e.g. more than one single nucleotide polymorphism. The nucleic acid sequences of this setting may be amplified by PCR with the aid of specific primers prior to their analysis on the microarray.

In assaying for expression of multiples genes of a subject, target polynucleotides are allowed to form stable complexes with probes on the aforementioned arrays in a hybridization reaction. It will be appreciated by one of skill in the art that where antisense RNA is used as the target nucleic acid, the sequence immobilized on the array are chosen to be complementary to sequences of the antisense nucleic acids. Conversely, where the target nucleic acid pool is a pool of sense nucleic acids, the sequence immobilized on the array are selected to be complementary to sequences of the sense nucleic acids. Finally, where the nucleic acid pool is double stranded, the probes may be of either sense and/or antisense as the target nucleic acids include both sense and antisense strands.

In one embodiment, labeled probes are utilized to perform a competitive hybridization on a microarray. In this assay format, a target nucleic acid from a test sample competes with a probe of the present invention for binding of a known sequence immobilized on the microarray. The amount of labeled probes that will bind to the immobilized known sequences is inversely proportional to the concentration of corresponding target nucleic acids in the test sample.

The subject amplification and any other hybridization assays described herein can be used to detect any target nucleic acids from any sources suspected to contain the target. It is not intended to be limited as regards to the source of the sample or the manner in which it is made. Generally, the test sample can be biological and/or environmental samples. Biological samples may be derived from human or other animals, body fluid, solid tissue samples, tissue cultures or cells derived therefrom and the progeny thereof, sections or smears prepared from any of these sources, or any other samples that contain nucleic acids. Preferred biological samples are body fluids including but not limited to urine, blood, cerebrospinal fluid, spinal fluid, sinovial fluid, semen, ammoniac fluid, cerebrospinal fluid (CSF), and saliva. Other types of biological sample may include food products and ingredients such as dairy items, vegetables, meat and meat by-products, and waste. Environmental samples are derived from environmental material including but not limited to soil, water, sewage, cosmetic, agricultural and industrial samples, as well as samples obtained from food and dairy processing instruments, apparatus, equipment, disposable, and non-disposable items.

Polynucleotides labeled according to the invention may also be used in gel shift assays. Such an assay, also known as electrophoretic mobility shift assay (EMSA), gel mobility shift assay, band shift assay, or gel retardation assay, is a common technique used to study protein-DNA or protein-RNA interactions. This procedure can determine if a protein or mixture of proteins is capable of binding to a given DNA or RNA sequence, and can sometimes indicate if more than one protein molecule is involved in the binding complex. Labeled oligonucleotides may be used in gel shift assays by peforming electrophoresis and subsequently determining the extent of migration of the labeled oligonucleotides in the gel by visualizing the emission of the fluorescent label. Gel shift assays may be performed in vitro concurrently with DNase footprinting, primer extension, and promoter-probe experiments when studying transcription initiation, DNA replication, DNA repair or RNA processing and maturation. Methods of performing gel shift assays are known. See, e.g. Garner, M. M. and Revzin, A. (1981) "A gel electrophoresis method for quantifying the binding of proteins to specific DNA regions: application to components of the *Escherichia coli* lactose operon regulatory system." Nucleic Acids Res. 9:3047-3060 or Fried, M. and Crothers, D. M. (1981) "Equilibria and kinetics of lac repressor-operator interactions by polyacrylamide gel electrophoresis." Nucleic Acids Res., 9:6505-6525.

Fluorescently labeled polypeptides of the invention are useful in a wide variety of assays. Such assays can be performed to discern specific protein-protein interactions, protein-nucleic acid interaction, interactions between a protein of interest and candidate inhibitors or activators. Candidate inhibitors or activators include but are not limited to antisense oligonucleotides, double stranded RNAs, ribozymes, a ribozyme derivatives, antibodies, liposomes, small molecules, inorganic or organic compounds. The subject assays can also be performed to study enzymatic kinetics, for e.g., drug design, screen and/or optimization and can be performed using the fluorescently labeled polypeptides in solution or immobilized on a solid substrate.

Of particular interest is a specific interaction between a cell surface receptor and its corresponding ligand. Cell surface receptors are molecules anchored on or inserted into the cell plasma membrane. They constitute a large family of proteins, glycoproteins, polysaccharides and lipids, which serve not only as structural constituents of the plasma membrane, but also as regulatory elements governing a variety of biological functions. In another aspect, the specific protein-protein interaction involves a cell surface receptor and an immunoliposome or an immunotoxin. In yet another aspect, the specific protein-protein interaction may involve a cytosolic protein, a nuclear protein, a chaperon protein, or proteins anchored on other intracellular membranous structures. In yet another aspect, the specific protein-protein interaction is between a target protein (e.g., an antigen) and an antibody specific for that antigen.

A specific interaction between a labeled polypeptide and an interacting entity is assayed by mixing the two entities under conditions such interaction is suspected to occur. Typically, the interaction is visualized with the aid of an optical device. Where desired, these entities can be placed within an optical confinement (see, e.g., U.S. Pat. Nos. 7,267,673, and 7,170,050). Where single molecule is to be detected, each optical confinement contains only one target that is being investigated. This can be achieved by diluting a minute amount of target in a large volume of solution, such that deposition over an array of confinements results in a primary distribution, or a majority of confinements will have a single target molecule disposed there. The labeled polypeptide and the interacting entity can be immobilized onto the inner surface of the optical confinement by any of the methods available in the art. Such methods encompass the uses of covalent and noncovalent attachments effected by a variety of binding moieties. The choice of the binding moieties will depend on the nature of the labeled polypeptide and/or the interacting entity. One way to immobilize the labeled polypeptide or the proteinaceous probe involves the use of the streptavidin or avidin/biotin binding pair.

In one embodiment, the polypeptide to be reacted with a compound of the invention comprises 3 to about 80 amino acids. Examples of such polypeptides include, but are not limited to, neuropeptides, cytokines, toxins and peptidase or protease substrates. Fluorescently labeled-neuropeptides, -cytokines and -toxins may be used to map or visualize the distribution of the receptors specific to the respective peptides. As an example, when labeled with a compound of the invention, phalloidin, which is a toxin with a cyclic peptide structure, can be used to stain F-actin filaments in cells. As another example, when labeled with a fluorescent group of the invention, α-bungarotoxin, a peptide-based snake toxin, can be used to detect acetylcholine receptor. Peptidase or protease substrates labeled with a fluorescent group of the invention may be used to assay the activities of the peptidases or proteases, and used in screening drugs designed as inhibitors of the peptidases or proteases. For example, a peptide comprising a peptide sequence cleavable by a peptidase may be labeled at one end of the peptide sequence with a first fluorescent group, a fluorescence donor fluorescent group, selected from a fluorescent group of the invention and at the other end of the peptide sequence with a second fluorescent group, a fluorescence acceptor fluorescent group (such as another fluorescent group from the invention or a quencher), where the first dye and second dye form a fluorescence resonance energy transfer (FRET) pair. By detecting the fluorescence difference of either the donor fluorescent group or the acceptor fluorescent group of the FRET pair before and after the peptide is cleaved by said peptidase, the level of enzyme activity can be assessed.

Other polypeptide conjugates that can be prepared according to the invention include those of antibodies, lectins, enzymes, lipoproteins, albumins, avidin, streptavidin, annexins, protein A, protein G, transferrin, apotransferrin, phycobiliproteins and other fluorescent proteins, toxins, growth factors, tubulins, hormones, various receptors and ion channels.

In one embodiment, compounds of the invention may be reacted with antibodies. Such antibodies may be primary or secondary depending on the desired application. If the antigen to be detected is present in very small amounts, a secondary antibody may be used in order to provide signal amplification. Various secondary antibody isotypes may be labeled. Non-limiting examples of secondary antibody isotypes are Anti-mouse IgG, Anti-mouse IgM, Anti-rabbit IgG, Anti-rat IgG, Anti-rat IgM, Anti-guinea pig IgG, Anti-chicken IgG, Anti-hamster IgG, Anti-human IgG, Anti-human IgM, Anti-goat IgG, Anti-mouse IgG, Anti-rabbit IgG, Anti-rat IgG, Anti-sheep IgG, Anti-goat IgG, Anti-mouse IgG, Anti-human IgG, Anti-rat IgG, Anti-mouse IgG, Anti-human IgG, Anti-rat IgG, Anti-goat IgG, and Anti-rabbit IgG.

Alternatively, Fab fragments may be labeled with the compounds of the invention. Such fragments may be superior to whole antibody conjugates because they lack the Fc region, which would reduce nonspecific interactions with Fc receptor-bearing cell membranes and would allow better penetration into tissues.

Labeled secondary antibodies of the invention may be used in signal amplification kits such as those commercialized by Molecular Probes, Inc. Such kits could each provide two labeled antibodies specific to a primary antibodies, such as a mouse antibody. In one embodiment, a rabbit anti-mouse IgG antibody conjugate of the invention is first used to bind to the mouse-derived primary antibody. The fluorescence is then dramatically enhanced by the addition of a second conjugate of a goat anti-rabbit IgG antibody.

In yet another embodiment, the compounds of the invention may be used to label protein A and/or protein G. Protein A and protein G are bacterial proteins that bind with high affinity to the Fc portion of various classes and subclasses of immunoglobulins from a variety of species, such as Bovine, Cat, Chicken, Dog, Goat, Guinea pig, Horse, Human IgG1, IgG2, IgG3, IgG4, Human IgM, IgA, IgE, Human IgD, Mouse IgG1 or others, Pig, Rabbit, Rat or Sheep, which may be used in the detection of immunoglobulins. Alternatively, immunoglobins can be labeled with a compound of the invention and retains binding specificity to its target after such labeling. These labeled immunoglobins can be used for in-vitro or in-vivo detection of the target antigen. In some embodiments, the labeled immunoglobins comprise a fluorophore that has an absorption maximal wavelength equal to or greater than 750 nm. In other embodiments labeled immunoglobins comprise a fluorophore that has an absorption maximal wavelength equal to or greater than 685 nm. In various embodiments of the invention, such labeled immunoglobins bind to an antigen on a cancer cell. In some embodiments, the labeled immunoglobin binds to erb2.

Labeled antibodies prepared according to the invention may be primary antibodies for various applications. While secondary detection methods can provide significant signal amplification, a directly labeled primary antibody often produces lower background fluorescence and less nonspecific binding. Using primary antibodies also allows multiple primary antibodies of the same isotype or derived from the same species to be used in the same experiment when they are directly labeled.

Examples of such primary antibodies include polyclonal antibodies specific for reporter gene products. These include Anti-Green-Fluorescent Protein Antibodies, Anti-Glutathione S-Transferase Antibody, Anti-beta-Glucuronidase Antibody, Anti-beta-Galactosidase Antibody, Monoclonal Antibodies Specific for Epitope Tags, Penta His Antibody, Anti-HA Antibody and Anti-c-myc Antibody.

Organelle-specific labeled antibodies may also be prepared to label various subcellular organelles and components such as the endoplasmic reticulum, peroxisomes, mitochondria, or cytochrome c. Labeled antibodies may also be specific for proteins in the oxidative phosphorylation system, such as antibodies against cytochrome oxidase (Complex IV) or antibodies against Complexes I, II, III and V, or other mitochondrial proteins such as anti-mitochondrial porin antibodies or anti-pyruvate dehydrogenase antibodies.

In other embodiments, labeled antibodies specific for proliferation markers and cell-cycle control proteins may be prepared. Such antibodies include Anti-Bromodeoxyuridine Antibody (Anti-BrdU Antibody), which may for example be used in TUNEL assays, Anti-Human mRNA-Binding Protein HuR Antibody (Anti-HuR Antibody), Anti-Human Neuronal Protein HuC/HuD Antibody (Anti-Hu Antibody), Anti-cdc6 Peptide Antibody, Anti-CD Antibodies, Antibodies against D Cyclins/Cyclin-Dependent Kinase Inhibitors, and Anti-Phosphoinositide Antibodies.

Some labeled antibodies may be specific for structural cellular proteins. Examples of such antibodies are Anti-alpha-Tubulin Monoclonal Antibody, Anti-Glial Fibrillary Acidic Protein (GFAP) Antibody, Anti-Desmin Antibody, or Anti-Fibronectin Antibody. Additional antibodies suitable for use in the invention include antibodies specific for neuronal proteins such as Anti-Synapsin I Antibody or Anti-NMDA Receptor Antibodies. Other Polyclonal and Monoclonal Antibodies that may be labeled according to the invention include Anti-Human Golgin-97 Antibody, Anti-Human Transferrin Receptor Antibody, Antibodies against Matrix Metalloproteinases and Anti-Bovine Serum Albumin Antibody.

The specific interaction between an antigen and an antibody has been explored in the context of immunoassays utilizing the subject fluorescent compounds. The immunoassays can permit single-molecule detection or ensemble detection. The subject immunoassays can be performed to characterize biological entities, screen for antibody therapeutics, and determine the structural conformations of a target antigen. For instance, immunoassays involving antibodies that are specific for the biological entity or specific for a by-product produced by the biological entity have been routinely used to identify the entity by forming an antibody-entity complex. Immunoassays are also employed to screen for antibodies capable of activating or down-regulating the biological activity of a target antigen of therapeutic potential. Immunoassays are also useful for determining structural conformations by using anti-idotypic antibodies capable of differentiating target proteins folded in different conformations.

According to one embodiment of the invention, biomolecules labeled with a fluorescent group of the invention such as proteins are suitable for in vivo imaging, including without limitation imaging a biomolecule present inside a cell, a cell, tissue, organ or a whole subject. Where desired, the labeled biomolecules can be used to perform "In Cell Western" in which given molecules (e.g., a specific cellular protein) present inside a cell are stained and imaged.

The fluorescent groups of the invention and/or the labeled biomolecules of the present invention can be administered to a living subject in a variety of forms adapted to the chosen route of administration, i.e., orally, or parenterally. Parenteral administration in this respect includes, but is not limited to, administration by the following routes: intravenous, intramuscular, subcutaneous, parenteral, intraocular, intrasynovial, transepithelially including transdermal, opthalmic, sublingual, and buccal; topically including opthalmic, dermal, ocular, rectal and nasal inhalation via insufflation and aerosol and rectal systemic. In particular, proteins labeled with a fluorescent group of the invention comprising an mPEG as a water soluble polymer group may be advantageous. In vivo imaging may provide means for early detection, screening, diagnosis, image-guided surgical intervention, and treatment of various diseases. For example, Near IR fluorescent group-labeled toxin (Veiseh, et al. *Cancer Res.* 67(14), 6882(2007)) and antibody (Kulbersh, et al. *Arch Otolaryngol Head Neck Surg.* 133(5), 511(2007) have been used to detect and guide the surgical removal of tumors. In in-vivo imaging, a fluorescent probe, such as an antibody labeled with a fluorescent group, is first administered to an animal (such as a mammal). The animal is then imaged by applying an excitation light with a wavelength appropriate for the absorption of the fluorescent group and collecting the fluorescence signal at another wavelength appropriate for the emission of the fluorescent group. Typically, for efficient tissue penetration of both the excitation and emission lights, the absorption and emission wavelengths of the fluorescent group may be greater than 470 nm, greater than 550 nm, greater than 600 nm, or greater than 640 nm. Absorption and emission wavelengths may be less than 1,200 nm. Fluorescent groups with wavelengths in the 640 nm-1,200 nm range may be referred to as near infrared dyes, or near IR dyes, which are preferred for tissue or in vivo imaging. An important challenge for in vivo imaging using antibodies has been the relatively short half-life of the fluorescently labeled antibodies. It has been reported that antibodies labeled with more than 3 fluorescent group molecules were rapidly cleared from the body by translocating into the liver, where they became metabolized (BioProbes 52, 10-11, March 2007, by Molecular Probes, Inc). In order to extend the half-life of the labeled antibodies so that enough of the antibodies were available over time for detecting the target, it was necessary to lower the number of fluorescent group molecules per antibody (i.e., degree of labeling or DOL) to about 2. However, the lowering of DOL was at the expense of fluorescence brightness of the individual labeled antibody molecules. Thus, it would be desirable to have antibodies that are labeled with 3 or more fluorescent group molecules and that have a relatively long half-life in vivo. PEG is a known biocompatible material often used in functionalizing the surface of implantable medical devices (Balakrishanan, et al. Biomaterials 26(17), 3495(2005)) and in modifying drugs (Mehvar, et al. Pharm. Pharmaceut. Sci. 3, 125(2000); Wang, et al. J. Biochem. Cell Biology 34, 396(2002)). In practice of the subject invention, proteins, such as antibodies, may be labeled with single or multiple, such as more than 3, 4, 5, 6 or more fluorescent dye molecules of the invention and the antibodies labeled in such a manner can have a relatively long half-life in the body. In particular, the PEG group(s) in the fluorescent group can mask the fluorescent group such that an antibody labeled with multiple molecules of the fluorescent group is less immunogenic as compare to the same antibody labeled with a conventional fluorescent dye (such as Cy5.5, Cy7 or Alexa Fluor 750). In some aspects, PEG group(s) on the fluorescent group can mask or protect the antibody itself, making the antibody more resistant to hydrolysis by proteases.

In other embodiments of the invention, a method of in-vivo imaging of a subject is provided comprising the steps of administering to a subject in need thereof a biomolecule comprising a label which is a compound according to the invention the invention wherein the at least one reactive moiety of label has undergone a reaction which attached the label to the biomolecule and wherein the biomolecule further comprises a targeting moiety that binds to a binding partner on a cell of the subject which is indicative of the cell; binding the binding partner on the cell with the targeting moiety of the biomolecule thereby differentially labeling the cell relative to neighboring cells; directing exciting wavelength to the cell; and detecting emitted fluorescence from the cell of the subject thereby detecting the differentially labeled cell of the subject. The biomolecule may be an antibody, fragment of an antibody, protein, peptide, lipid or carbohydrate.

The compounds of the invention may also be used to produce labeled biomolecules for use in immunohistochemistry and immunocytochemistry experiments. In immunohistochemistry (IHC), the presence and location of proteins is determined within a tissue section by exploiting the principle of an antibody binding specifically to an antigens present in a biological tissue. Such experiments may, for example, be used in the diagnosis and treatment of cancer. Specific molecular markers are characteristic of particular cancer types and are known to persons skilled in the art. IHC can also be used in basic research to determine the distribution and localization of biomarkers in different parts of a tissue. Visualization of antibody-antigen interactions can be accomplished by reacting an antibody with a reactive fluorescent compound of the invention and using the labeled antibody to stain tissue sections. In immunocytochemistry, the labeled antibody is used to stain populations of cultured cells. These techniques can be combined with confocal laser scanning microscopy, which is highly sensitive and can also be used to visualise interactions between multiple proteins. Subcellular localization of proteins may also be possible using confocal microscopy.

Of particular interest is the use of the labeled polypeptide for conducing immunocytochemistry. Fluorescence immunocytochemistry combined with fluorescence microscopy provides visualization of biomolecules such as proteins and nucleic acids within a cell. One method uses primary antibodies hybridized to the desired target. Then, secondary antibodies conjugated with the subject fluorescent dyes and targeted to the primary antibodies are used to tag the complex. The complex is visualized by exciting the dyes with a wavelength of light matched to the dye's excitation spectrum.

Immunocytochemistry can also be employed to discern subcellular localization of a given protein or nucleic acid. For instance, colocalization of biomolecules in a cell is performed using different sets of antibodies for each cellular target. For example, one cellular component can be targeted with a mouse monoclonal antibody and another component with a rabbit polyclonal antibody. These are designated as the primary antibody. Subsequently, secondary antibodies to the mouse antibody or the rabbit antibody, conjugated to different fluorescent dyes of the present invention having different emission wavelengths, are used to visualize the cellular target.

The compounds of the invention or the labeled biomolecules of the invention can also be used to label cells or particles for a variety of applications. Accordingly, the present invention provides a method of individually labeling a cell within a population of cells whereby the cell is differentially labeled relative to neighboring cells within the population. The method typically comprises contacting the cell with a labeled biomolecule of the present invention, wherein said biomolecule comprises a targeting moiety that binds to a binding partner that is indicative of said cell, and thereby differentially labeling the cell relative to neighboring cells within the population. The targeting moiety can be any biomolecules that recognize a binding partner on the cell to be detected. The choice of the targeting moiety will vary depending on the cell that is to be labeled. For example, for detecting a cancer cell, a targeting moiety is selected such that its binding partner is differentially expressed on a cancer cell. A vast number of cancer markers are known in the art. They include without limitation cell surface receptors such as erb2, PDGF receptor, VEGF receptors, a host of intracellular proteins such as phosphatidylinositol 3-kinases, c-abl, raf, ras, as well as a host of nuclear proteins including transcription factors and other nucleic acid binding molecules. In some other embodiments, the cancer marker is Immunoglobulin epsilon Fc receptor II, Alk-1, CD20, EGF receptor, FGF receptor, NGF receptor, EpCam, CD3, CD4, CD11a, CD19, CD22, CD30, CD33, CD38, CD40, CD51, CD55, CD80, CD95, CCR2, CCR3, CCR4, CCR5, CTLA-4, Mucin 1, Mucin 16, Endoglin, Mesothelin receptor, Nogo receptor, folate receptor, CXCR4, insulin-like growth factor receptor, Ganglioside GD3, and alpha or beta Integrins. To differentially label various cell types, targeting moieties recognizing a cell-specific binding partner can be used. For example, there are a host of protein markers differentially expressed on T cells as opposed on B cells or other cells of different lineage. Neuronal markers, muscle cell markers, as well as markers indicative of cells of ectodermal, mesodermal or endodermal origins are also known in the art, all of which can be used depending on the intended applications. The targeting moieties can be antibodies, receptors, cytokines, growth factors, and any other moieties or combinations thereof that are recognized by a binding partner on the cell to be labeled. The cell which is labeled may be labeled intracellularly.

The differentially labeled cells can be imaged by directing exciting wavelength to the cell and detecting emitted fluorescence from the cell, in a number of in-vitro formats, either in solution or immobilized on a substrate.

The labeled cells and/or the intensity of the fluorescence may be detected or quantified by performing flow cytometry. Cells or particles labeled with the compounds of the invention or stained with labeled biomolecules of the invention may also be separated and isolated based on the specific properties of the label using fluorescence activated cell sorting (FACS). Such techniques are known in the art. Briefly, cells are labeled with a subject fluorescent dye and then passed, in a suspending medium, through a narrow dropping nozzle so that each cell is typically in a small droplet. A laser based detector system is used to excite fluorescence and droplets with positively fluorescent cells are given an electric charge. Charged and uncharged droplets are separated as they fall between charged plates and so collect in different tubes. The machine can be used either as an analytical tool, counting the number of labeled cells in a population or to separate the cells for subsequent growth of the selected population. Further sophistication can be built into the system by using a second laser system at right angles to the first to look at a second fluorescent label or to gauge cell size on the basis of light scatter.

Additional guidance for performing fluorescent cell sorting can be found in publications such as the following: Darzynkiewicz, Z., Crissman, H. A. and Robinson, J. P., Eds., Cytometry, Third Edition Parts A and B (Methods in Cell Biology, Volumes 63 and 64), Academic Press (2001); Davey, H. M. and Kell, D. B., "Flow cytometry and cell sorting of heterogeneous microbial populations: the importance of single-cell analyses," Microbiological Rev 60, 641-696 (1996); Givan, A. L., Flow Cytometry: First Principles, Second Edition, John Wiley and Sons (2001); Herzenberg, L. A., Parks, D., Sahaf, B., Perez, O., Roederer, M. and Herzenberg, L. A., "The history and future of the fluorescence activated cell sorter and flow cytometry: a view from Stanford," Clin Chem 48, 1819-1827 (2002); Jaroszeski, M. J. and Heller, R., Eds., Flow Cytometry Protocols (Methods in Molecular Biology, Volume 91), Humana Press (1997); Ormerod, M. G., Ed., Flow Cytometry: A Practical Approach, Third Edition, Oxford University Press (2000); Robinson, J. P., Ed., Current Protocols in Cytometry, John Wiley and Sons (1997); Shapiro, H. M., "Optical measurement in cytometry: light scattering, extinction, absorption and fluorescence," Meth Cell Biol 63, 107-129 (2001); Shapiro, H. M., Practical Flow Cytometry, Fourth Edition, Wiley-Liss (2003); Weaver, J. L., "Introduction to flow cytometry," Methods 21, 199-201 (2000).

Fluorescent compounds of the invention are also particularly suitable for applications where multiplexed detection of analytes is necessary, such as in full spectrum flow cytometry methods. In such methods, the entire emission spectrum of a given dye excited with one or more lasers (e.g. 1, 2, 3, 4, 5 or more lasers) is captured and stitched together using software to create a spectral signature that combines emission information from all lasers. Using spectral unmixing algorithms such as Ordinary Least Square (OLS), the contribution of each known fluorophore's spectrum to the total collected emission signal can be calculated. It is generally helpful for the spectral emission profile of each dye to be as distinct as possible, and therefore compounds of the invention may enable the simultaneous detection of at least 5, 10, 15, 20, 30, or 40 individual markers or colors.

Fluorescent compounds of the invention may also be used for fluorescence lifetime imaging (FLIM). FLIM is a useful technique for producing images based on the variation in the fluorescence decay characteristics of a fluorescent sample. It can be used as an imaging technique in confocal microscopy and other microscope systems. The lifetime of the fluorophore signal, rather than its intensity, is used to create the image in FLIM, which has the advantage of minimizing the effect of photon scattering in thick layers of sample. FLIM may be useful for biomedical tissue imaging, allowing to probe greater tissue depths than conventional fluorescence microscopy.

The compounds of the invention may be used in single molecule applications. Removal of ensemble averaging by observing individual molecules of fluorescent group may allow the determination of the mechanism of biological and chemical processes. Such processes may include the translocation of protein motors such as kinesin or myosin, formation, dissolution and translocation of cellular protein complexes and the mechanism of action of DNA or RNA polymerases. In such experiments, the present compounds may be used, for example, to label biomolecules which are attached to a surface such as a microscopy slide or flow chamber. Individual fluorophores may subsequently be observed using total internal reflection fluorescence microscopy.

The present compounds may also be used for the labeling of lipids. Lipids are involved in many biological processes, and the labeling of lipids and lipid rafts may is often a valuable method for studying their properties. Various lipid monolayers and bilayers may be labeled in live cells or artificial systems such as liposomes and micelles. For example, a live cell population may be labeled with a fluorescent conjugate prepared by reacting a compound of the invention and cholera toxin subunit B, which specifically interacts with lipid rafts. Such lipid rafts may then be crosslinked into distinct membrane patches by the use of an anti-cholera toxin antibody, which may be labeled with one of the present compounds.

The labeled polypeptides of the present invention find use as biosensors in prokaryotic and eukaryotic cells, e.g. as calcium ion indicators, as pH indicators, as phorphorylation indicators, as indicators of other ions including without limiting to magnesium, sodium, potassium, chloride and halides. For example, for detection of calcium ion, proteins containing an EF-hand motif are known to translocate from the cytosol to membranes upon binding to calcium ion. These proteins contain a myristoyl group that is buried within the molecule by hydrophobic interactions with other regions of the protein. Binding of calcium ion induces a conformational change exposing the myristoyl group which then is available for the insertion into the lipid bilayer. Labeling such an EF-hand containing protein with a subject fluorescent dye makes it an indicator of intracellular calcium ion concentration by monitoring the translocation from the cytosol to the plasma membrane. Such monitoring can be performed with the use of an optical detector, e.g., a confocal microscope. EF-hand proteins suitable for use in this system include, but are not limited to: recoverin (1-3), calcineurin B, troponin C, visinin, neurocalcin, calmodulin, parvalbumin, and the like.

For use as a pH indicator, a system based on hisactophilins may be employed. Hisactophilins are myristoylated histidine-rich proteins known to exist in Dictyostelium. Their binding to actin and acidic lipids is sharply pH-dependent within the range of cytoplasmic pH variations. In living cells membrane binding seems to override the interaction of hisactophilins with actin filaments. At pH of approximately 6.5 they typically locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By conjugating the subject fluorescent dye to hisactophilin, the intracellular distribution of the labeled hisactophilin can be followed by laser scanning, confocal microscopy or standard fluorescence microscopy. Quantitative fluorescence analysis can be done by performing line scans through cells (laser scanning confocal microscopy) or other electronic data analysis (e.g., using metamorph software (Universal Imaging Corp) and averaging of data collected in a population of cells.

The subject fluorescent proteins also find use in applications involving the automated screening of arrays of cells by using microscopic imaging and electronic analysis. Screening can be used for drug discovery and in the field of functional genomics: e.g., where the subject proteins are used as markers of whole cells to detect changes in multicellular reorganization and migration, e.g., formation of multicellular tubules (blood vessel formation) by endothelial cells, migration of cells through Fluoroblok Insert System (Becton Dickinson Co.), wound healing, neurite outgrowth; where the proteins are used as markers fused to peptides (e.g., targeting sequences) and proteins that allow the detection of change of intracellular location as indicator for cellular activity, for example: signal transduction, such as kinase and transcription factor translocation upon stimuli, such as protein kinase C, protein kinase A, transcription factor NFkB, and NFAT; cell cycle proteins, such as cyclin A, cyclin B1 and cyclinE; protease cleavage with subsequent movement of cleaved substrate, phospholipids, with markers for intracellular structures such as endoplasmic reticulum, Golgi apparatus, mitochondria, peroxisomes, nucleus, nucleoli, plasma membrane, histones, endosomes, lysosomes, microtubules, actin.

The subject fluorescent proteins also find use in high throughput screening assays. The subject fluorescent proteins are typically more stable than proteins lacking the subject fluorescent dyes. In some aspects, the fluorescent proteins can exhibit a serum half-life of more than 1 hour, 2 hours, 5 hours, or 24 hours or more.

The subject fluorescent proteins can be used as second messenger detectors, e.g., by conjugating the subject fluorescent dyes to specific signaling domains, e.g., calcium binding SH2-, SH3-, PH-, PDZ-domain and etc.

The examples below are for the purpose of illustrating the practice of the invention. They shall not be construed as being a limitation on the scope of the invention or claims.

EXAMPLES

Example 1: Preparation of Compound 1

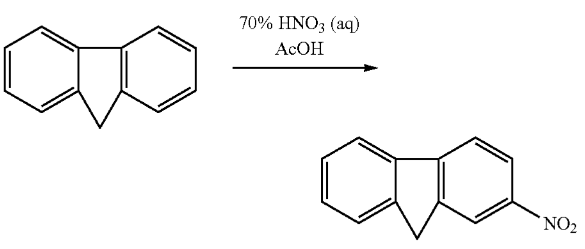

1

A mixture of fluorene (60 g) in AcOH (500 mL) was mechanically stirred in a 3-neck round-bottom flask and the temperature of the solution was raised to an internal temperature of 50° C. Then 70% nitric acid (aq) was added dropwise over the course of 15 minutes with continuous stirring. The temperature was raised to 70° C. and solid product began to form from the clear mixture. The reaction was monitored by TLC until a lower $R_f$ yellow spot formed (silica, 4/6, chloroform/hexane on silica). Once the reaction was complete and no fluorene remained, the reaction was cooled to room temperature. The solid was filtered out and washed with water (3×200 mL). The solid was dried under vacuum. The solid was recrystallized from EtOAc to give pure compound 1 (60 g).

Example 2: Preparation of Compound No. 2

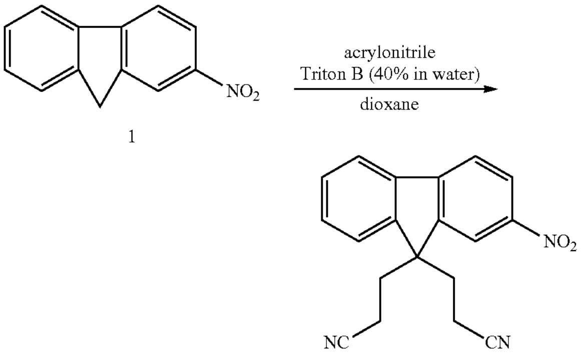

1

2

A mixture of compound 1 (56.4 g) in dioxane (400 mL) was mechanically stirred in a 3-neck round-bottom flask. The 40% Triton B solution (1.3 mL) was added and the reaction turned deep purple. After 5 minutes of stirring, acrylonitrile (37 mL) was added dropwise. The temperature rose to ~40° C. The reaction was stirred overnight. The reaction was checked by TLC (silica, 1/9, EtOAc/chloroform) and showed complete conversion of the starting material to a lower Rf spot. After the reaction was complete the reaction was concentrated. The solid product was recrystallized from organic solvent to give pure compound 2 (70 g).

Example 3: Preparation of Compound No. 3

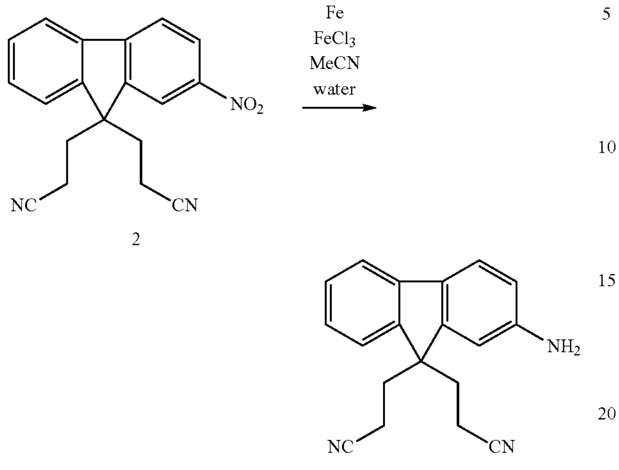

2

3

Compound 2 (70 g), iron powder (100 g), and iron chloride hexahydrate (1 g) were suspended in water (200 mL) and MeCN (1.5 L) in a 3-neck round-bottom flask and gently refluxed (internal temperature at 80° C.) overnight. TLC (silica, 3/97, MeOH/chloroform) showed complete conversion of compound 2 to a lower $R_f$ spot. The hot reaction was filtered through celite. The filtrate was concentrated and the solid product was recrystallized form organic solvent to give compound 3 (63 g).

Example 4: Preparation of Compound No. 4

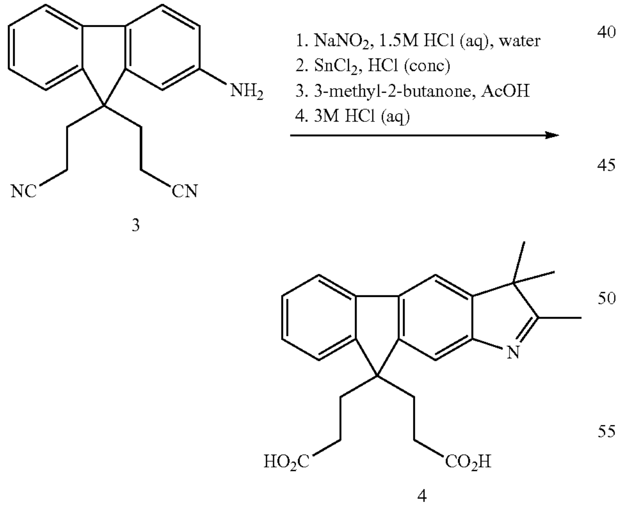

3

4

Compound 3 (63 g) was stirred in 1.5M HCl (aq) (600 mL) in a 3-necked round-bottom flask. The mixture was cooled to an internal temperature <5° C. A solution of sodium nitrite (16.7 g) in water (30 mL) was added dropwise while maintaining the internal temperature at <5° C. The reaction was stirred for 30 minutes at an internal temperature <5° C. A solution of tin chloride (140 g) in concentrated HCl (60 mL) was added dropwise. The internal temperature of the reaction was maintained at <15° C. during the addition. The reaction was stirred for 1 hour at room temp. The liquid was decanted off of the reaction. The gummy residue at the bottom of the flask was taken up in MeCN and concentrated and dried. TLC (silica, 10/90, MeOH/chloroform) showed complete conversion of compound 3 to a new spot. To the solid residue was added AcOH (500 mL) and 3-methyl-2-butanone (47 mL). The reaction was refluxed overnight. TLC (silica, 10/90, MeOH/chloroform) showed complete conversion of the intermediate to a higher $R_f$-spot. The warm reaction was hot filtered to remove any ammonium salts. The filtrate was evaporated and the crude solid was refluxed in aqueous 3M HCl (400 mL) overnight. The mixture was cooled to room temp. and the solid was filtered out of the solution after some neutralization (the pH did not go above 7 during neutralization). The product was recrystallized from organic solvent to give compound 4 (50 g).

Example 5: Preparation of Compound No. 5

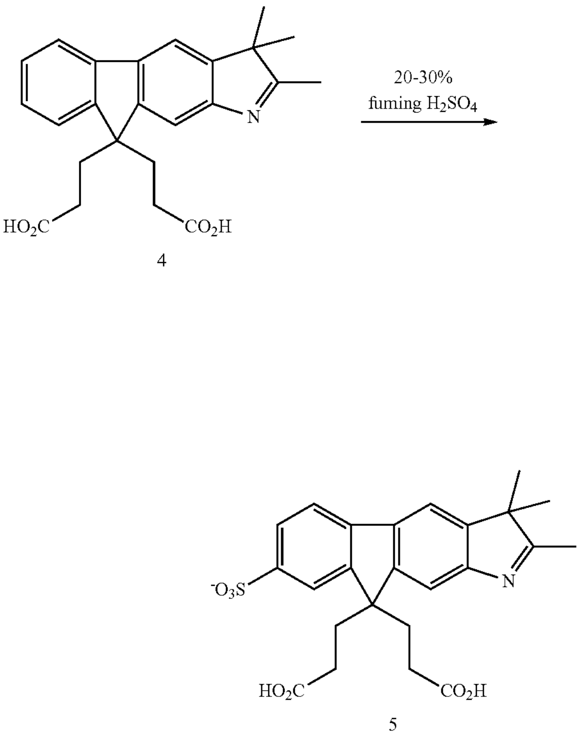

4

5

A portion of 20-30% fuming sulfuric acid (39 mL) was cooled in a round bottom flask with stir bar and cap in a freezer at −20° C. for 1 hour. To the acid was added compound 4 (10 g) with stirring. The flask was stirred in an ice bath to prevent the temperature from getting too high while compound 4 was dissolved. The reaction was stirred at rt overnight. The reaction was pipetted dropwise into $Et_2O$ (500 mL) which had been pre-cooled in a dry-ice/acetone bath. The gummy mixture in the ether was stirred for 1 hour. The ether layer was decanted and replaced with more ether. The gummy material was dissolved in water and neutralized with triethylamine. The solution was concentrated to dryness and the product was purified by silica chromatography (MeCN/water) to give compound 5 (10.5 g).

Example 6: Preparation of Compound No. 6

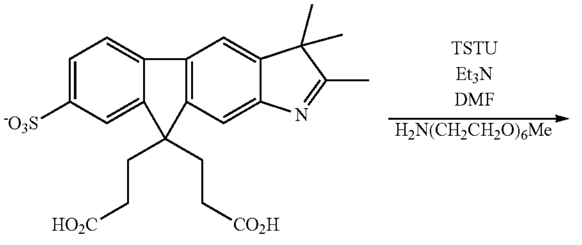

5

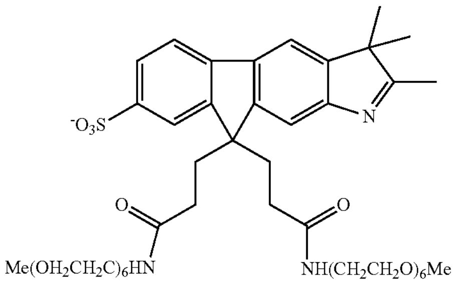

6

Compound 5 (724 mg) was dissolved in DMF (15 mL) and triethylamine (1.07 mL). TSTU (973 mg) was added. After 30 minutes, TLC of the reaction mixture (silica, 10/90, water/MeCN) showed complete conversion of compound 5 to a higher $R_f$ spot. The PEG6-amine (1.0 g) was added and the reaction was allowed to stir overnight at rt. TLC (silica, 10/90, water/MeCN) showed complete conversion of the bis-SE intermediate to a lower $R_f$ spot. The reaction was concentrated and the residue was purified by silica chromatography (water/MeCN) to give compound 6 (1.02 g).

Example 7: Preparation of Compound No. 7

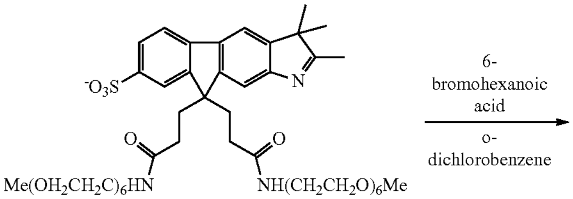

6

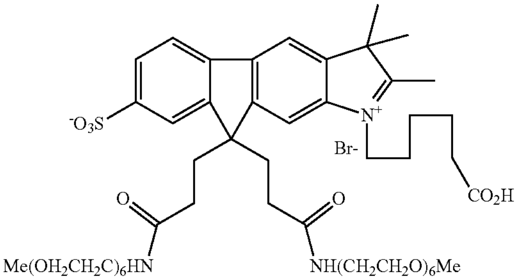

7

Compound 6 (2.797 g) and 6-bromohexanoic acid (1.06 g) were dissolved in o-dichlorobenzene (6 mL) in a dried/capped flask under argon. The reaction was heated at 110° C. overnight under an argon atmosphere. The residue was cooled to rt and vigorously stirred with ether several times, decanting the ether after each cycle. The remaining solid residue was dried to a constant weight to give compound 7 (2.70 g).

Example 8: Preparation of Compound No. 8

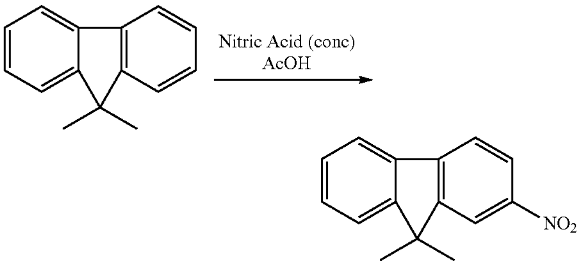

8

To a mixture of 9,9-dimethylfluorene (3.28 g) in AcOH (25 mL) at 0° C. was added fuming nitric acid (1.5 mL) dropwise. The reaction was stirred for 2 hours at rt. TLC of the reaction (silica, 95/5, hexane/DCM) showed complete conversion of the starting material to a lower $R_f$ spot. The reaction was added dropwise to water (300 mL) and the solid product was precipitated. The solid was filtered out and dried to a constant weight to give compound 8 (3.30 g)

Example 9: Preparation of Compound No. 9

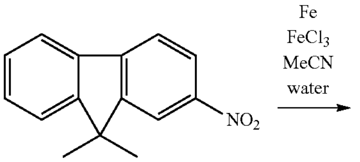

8

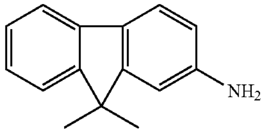

9

Compound 8 (3.3 g), 10% Pd/C (52 mg), and hydrazine hydrate (1.65 mL) were suspended in EtOH (55 mL) and refluxed for 2 hours. TLC (silica, hexane/EtOAc, 6/4) showed complete conversion of compound 8 to a lower $R_f$ spot. The hot reaction was filtered through celite (washed with methanol) and the filtrate was concentrated and dried to give compound 9 (2.89 g).

Example 10: Preparation of Compound No. 10

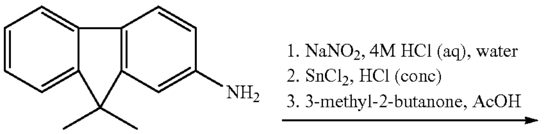

9

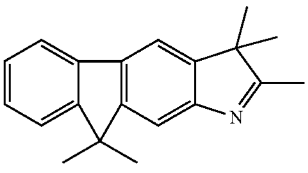

10

Compound 9 (2.89 g) was stirred in aqueous 4M HCl (240 mL) in a round-bottom flask. The mixture was cooled to an internal temperature <5° C. A solution of sodium nitrite (1.142 g) in water (10 mL) was added dropwise while maintaining the internal temperature at <5° C. The reaction was stirred for 30 minutes at internal temperature <5° C. A solution of tin chloride (10.5 g) in conc. HCl (10.5 mL) was added dropwise. The internal temperature of the reaction was maintained at <15° C. during the addition. The reaction was stirred for 2 hours at room temperature. Dichloromethane (250 mL) was added to the reaction mixture and the mixture was stirred for 1 hour. The solid was filtered out and dried. The aqueous layer was basicified with NaOH and more solid crashed out. This solid was filtered and dried as well. Both solids were combined and powdered to give the hydrazide intermediate. The hydrazide intermediate was dissolved in AcOH (11 mL) and 3-methyl-2-butanone (4.2 mL). The reaction was refluxed for 3 hours. The reaction was cooled to room temperature and concentrated. The residue was suspended in EtOAc (100 mL) and water (100 mL). The mixture was stirred while the aqueous layer was slowly neutralized by addition of aqueous sodium bicarbonate. The aqueous layer was extracted twice more with EtOAc. The EtOAc layers were combined, dried over magnesium sulfate, filtered, concentrated, and dried to give compound 10 (2.73 g).

Example 11: Preparation of Compound No. 11

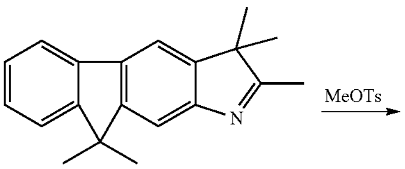

10

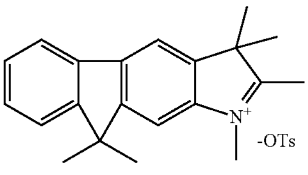

11

Compound 10 (112.7 mg) and methyl tosylate (400 mg) were mixed in a sealed tube. The reaction was heated at 120° C. overnight. The residue was cooled to room temperature and vigorously stirred with ether several times, decanting the ether after each cycle. The remaining solid residue was dried to a constant weight to give compound 11 (100 mg).

Example 12: Preparation of Compound No. 12

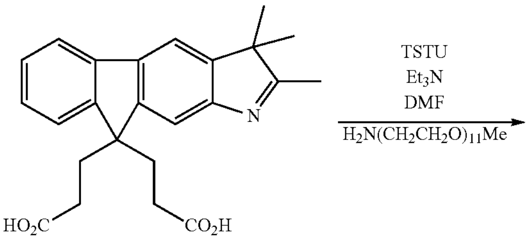

4

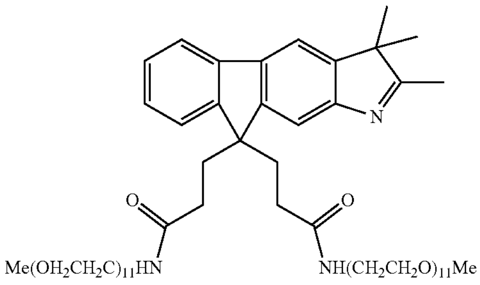

12

Compound 4 (391.5 mg) was dissolved in DMF (20 mL) and triethylamine (1.39 mL). TSTU (602 mg) was added. After 30 minutes, TLC of the reaction mixture (silica, 10/90, MeOH/DCM) showed complete conversion of compound 5 to a higher $R_f$ spot. The PEG11-amine (1.13 g) was added and the reaction was allowed to stir overnight at room temperature. TLC (silica, 10/90, MeOH/DCM) showed complete conversion of the bis-SE intermediate to a lower $R_f$ spot. The reaction was concentrated and the residue was purified on a silica column (MeOH/DCM) to give compound 12 (750 mg).

Example 13: Synthesis of Compound No. 13

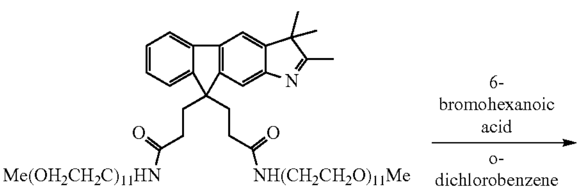

12

-continued

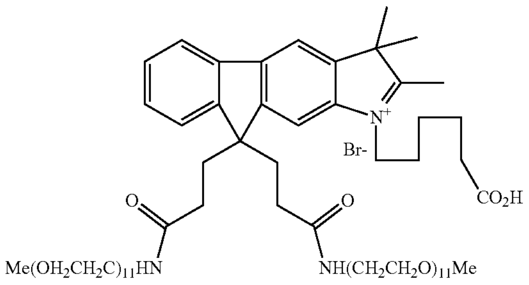

13

Compound 12 (693 mg) and 6-bromohexanoic acid (195 mg) were dissolved in o-dichlorobenzene (1 mL) in a dried/capped flask under argon. The reaction was heated at 110° C. overnight under an argon atmosphere. The residue was cooled to room temperature and vigorously stirred with ether several times, decanting the ether after each cycle. The remaining solid residue was dried to a constant weight to give compound 13 (740 mg).

Example 14: Synthesis of Compound No. 14

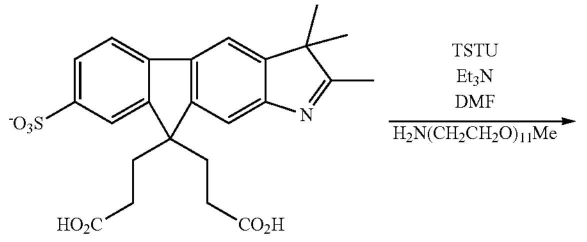

5

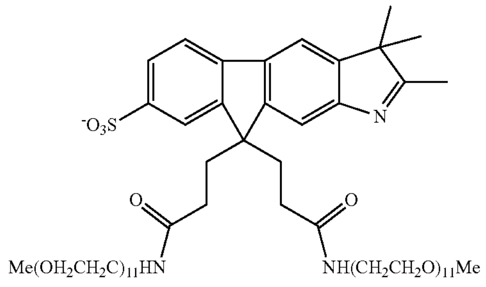

14

Compound 5 (724 mg) was dissolved in DMF (15 mL) and triethylamine (1.07 mL). TSTU (973 mg) was added. After 30 minutes, TLC of the reaction mixture (silica, 10/90, water/MeCN) showed complete conversion of compound 5 to a higher $R_f$ spot. The PEG11-amine (1.74 g) was added and the reaction was allowed to stir overnight at room temperature. TLC (silica, 10/90, water/MeCN) showed complete conversion of the bis-SE intermediate to a lower $R_f$ spot. The reaction was concentrated and the residue was purified on a silica column (water/MeCN) to give compound 14 (1.3 g).

Example 15: Synthesis of Compound No. 15

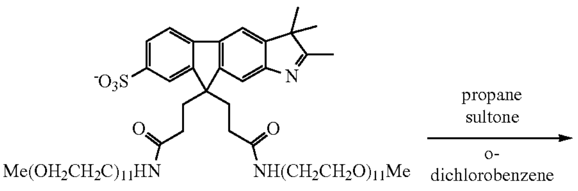

14

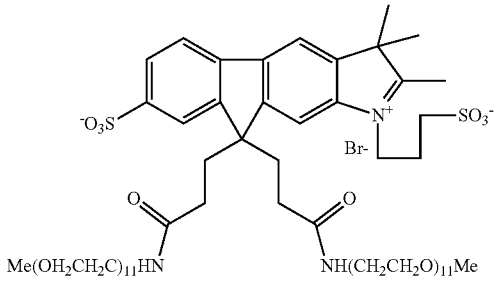

15

Compound 14 (733 mg) and propane sultone (122 mg) were dissolved in o-dichlorobenzene (1 mL) in a dried/capped flask under argon. The reaction was heated at 90° C. overnight under an argon atmosphere. The residue was cooled to room temperature and vigorously stirred with ether several times, decanting the ether after each cycle. The remaining solid residue was dried to a constant weight to give compound 15 (700 mg).

Example 16: Synthesis of Compound No. 16

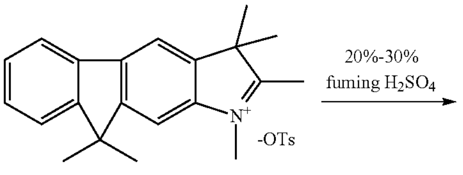

11

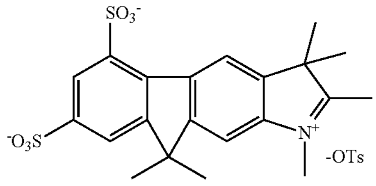

16

A portion of 20-30% fuming sulfuric acid (2 mL) was cooled in a round bottom flask with stir bar and cap in a freezer at −20° C. for 1 hour. To the acid was added compound 11 (85.3 mg). The flask was stirred in an ice bath to prevent the temperature from getting too high while compound 11 was dissolved. The reaction was stirred at room temperature overnight. The reaction was pipetted dropwise into $Et_2O$ (30 mL) which had been pre-cooled in a dry-ice/acetone bath. The gummy mixture in the ether was stirred for 1 hour. The ether layer was decanted and replaced with more ether. The gummy material was dissolved in water and neutralized with triethylamine. The solution was concentrated to dryness and the product was purified by silica chromatography (MeCN/water) to give compound 16 (50 mg).

Example 17: Synthesis of Compound No. 17

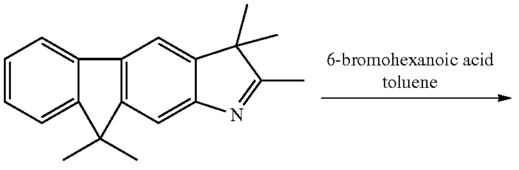

10

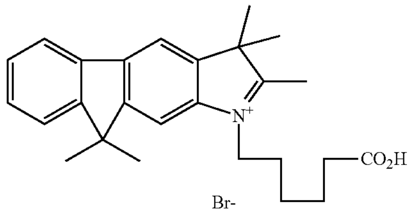

17

Compound 10 (2.5805 g) and 6-bromohexanoic acid (3.66 g) were dissolved in toluene (5 mL). The reaction was heated at 120° C. overnight. The residue was cooled to room temperature and vigorously stirred with EtOAc several times, decanting the EtOAc after each cycle. The remaining solid residue was dried to a constant weight to give compound 17 (2.50 g).

Example 18: Synthesis of Compound No. 18

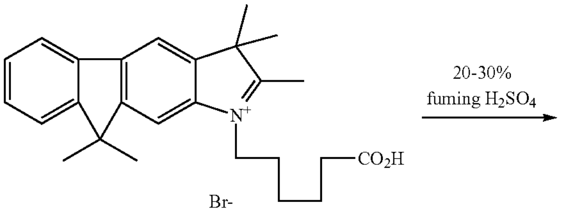

17

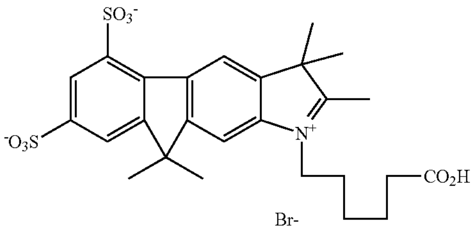

18

A portion of 20-30% fuming sulfuric acid (10 mL) was cooled in a round bottom flask with stir bar and cap in a freezer at −20° C. for 1 hour. To the acid was added compound 17 (590 mg). The flask was stirred in an ice bath to prevent the temperature from getting to high while compound 17 was dissolved. The reaction was stirred at room temperature overnight. The reaction was pipetted dropwise into $Et_2O$ (150 mL) which had been pre-cooled in a dry-ice/acetone bath. The gummy mixture in the ether was stirred for 1 hour. The ether layer was decanted and replaced with more ether. The gummy material was dissolved in water and neutralized with triethylamine. The solution was concentrated to dryness and the product was purified by silica chromatography (MeCN/water) to give compound 18 (400 mg).

Example 19: Synthesis of Compound No. 19

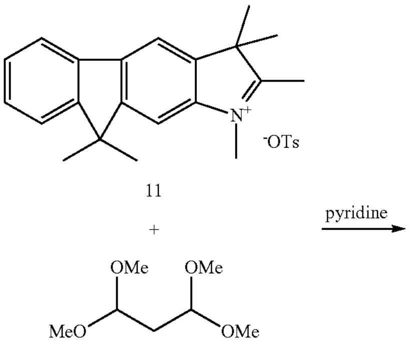

11

+

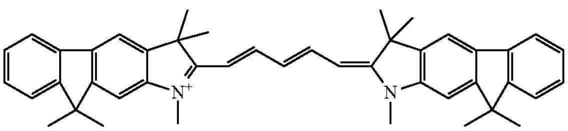

19

Compound 11 (127 mg) was dissolved in pyridine (2 mL) and brought to reflux. Then 1,1,3,3-tetramethoxypropane (0.46 mL) was added dropwise. The reaction was refluxed for 1 hour to give essentially complete conversion to a blue product. The reaction was concentrated and purified via silica chromatography (DCM/MeOH) to give pure compound 19 (30 mg) as a blue solid.

Example 20: Synthesis of Compound No. 20

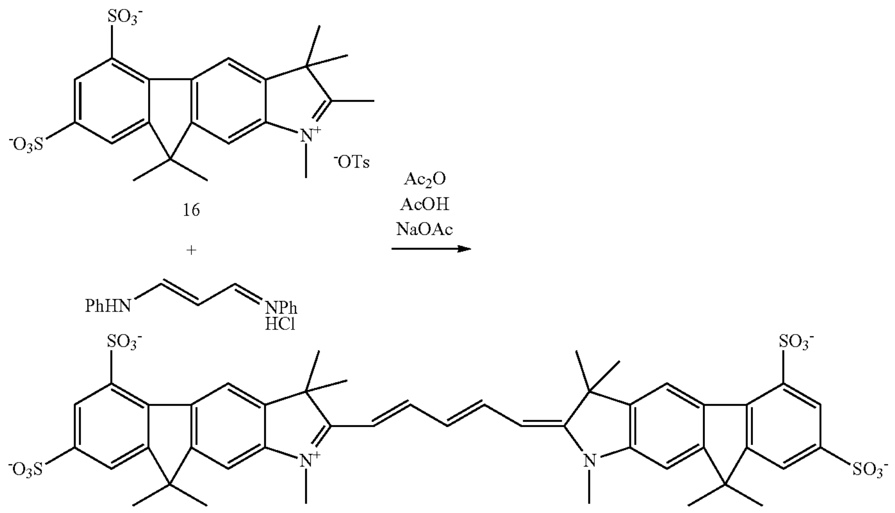

16

+

20

Compound 16 (25 mg) and malonaldehyde dinanilide hydrochloride (12.9 mg) were dissolved in AcOH (1 mL) and $Ac_2O$ (1 mL) and refluxed at 120° C. for 30 minutes. The reaction was cooled to 60° C. and then more compound 16 (25 mg) and NaOAc (81 mg) were added to the reaction. The reaction was refluxed at 120° C. for 2 hours. The deep blue solution was cooled to room temperature and concentrated at reduced pressure. The mixture was purified by preparative HPLC to give pure compound 20 (15 mg).

Example 21: Synthesis of Compound No. 21

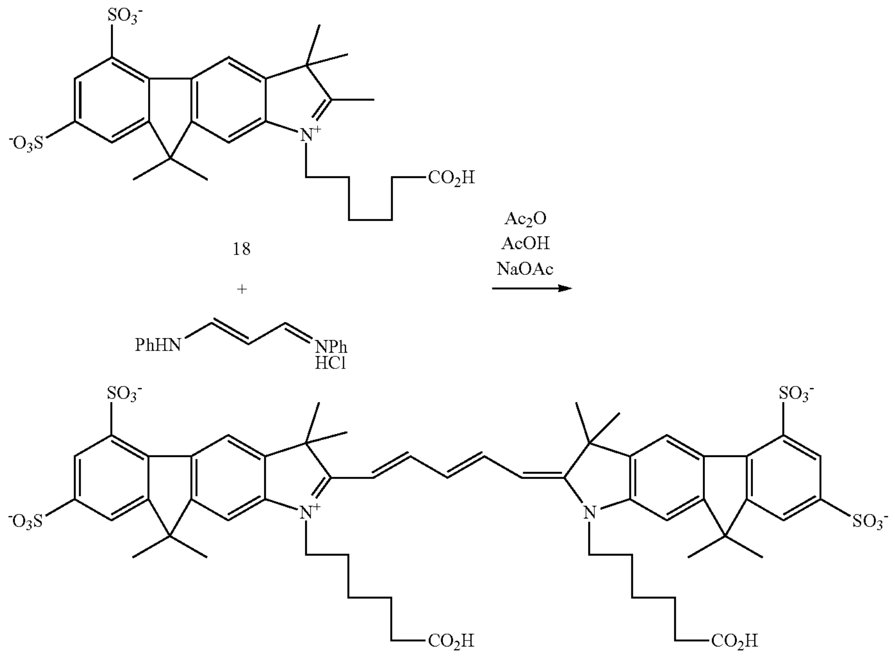

18

+

21

Compound 18 (28 mg) and malonaldehyde dinanilide hydrochloride (13.2 mg) were dissolved in AcOH (1 mL) and $Ac_2O$ (1 mL) and refluxed at 120° C. for 30 minutes. The reaction was cooled to 60° C. and then more compound 18 (28 mg) and NaOAc (146 mg) were added to the reaction. The reaction was refluxed at 120° C. for 2 hours. The deep blue solution was cooled to room temperature and concentrated at reduced pressure. The mixture was purified by preparative HPLC to give pure compound 21 (17 mg).

Example 22: Synthesis of Compound No. 22

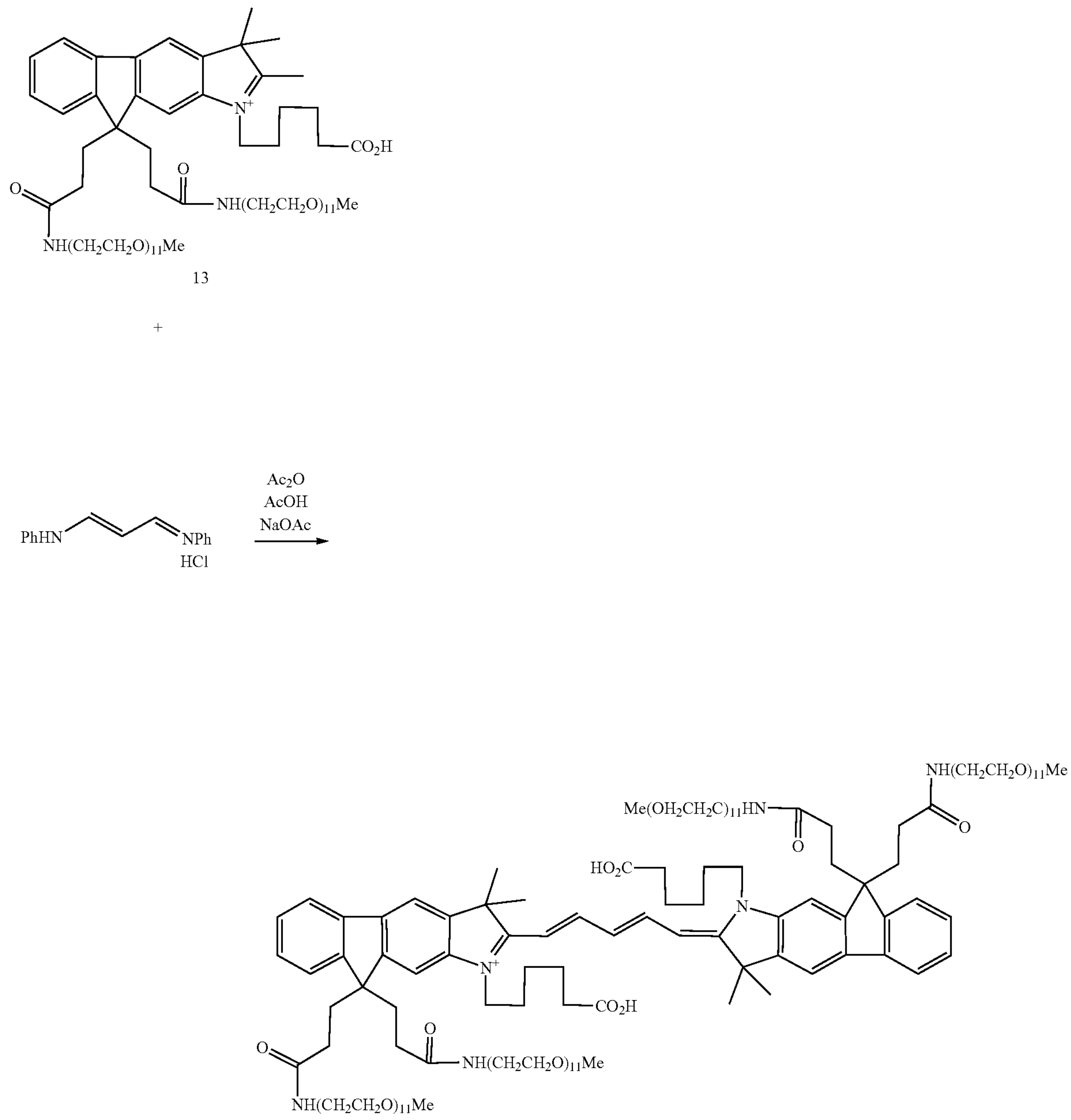

13

+

22

Compound 13 (47 mg) and malonaldehyde dinanilide hydrochloride (7.7 mg) were dissolved in AcOH (1 mL) and $Ac_2O$ (1 mL) and refluxed at 120° C. for 30 minutes. The reaction was cooled to 60° C. and then more compound 13 (47 mg) and NaOAc (44.3 mg) were added to the reaction. The reaction was refluxed at 120° C. for 1 hour. The deep blue solution was cooled to room temperature and concentrated at reduced pressure. The mixture was purified by preparative HPLC to give pure compound 22 (22 mg).

Example 23: Synthesis of Compound No. 23

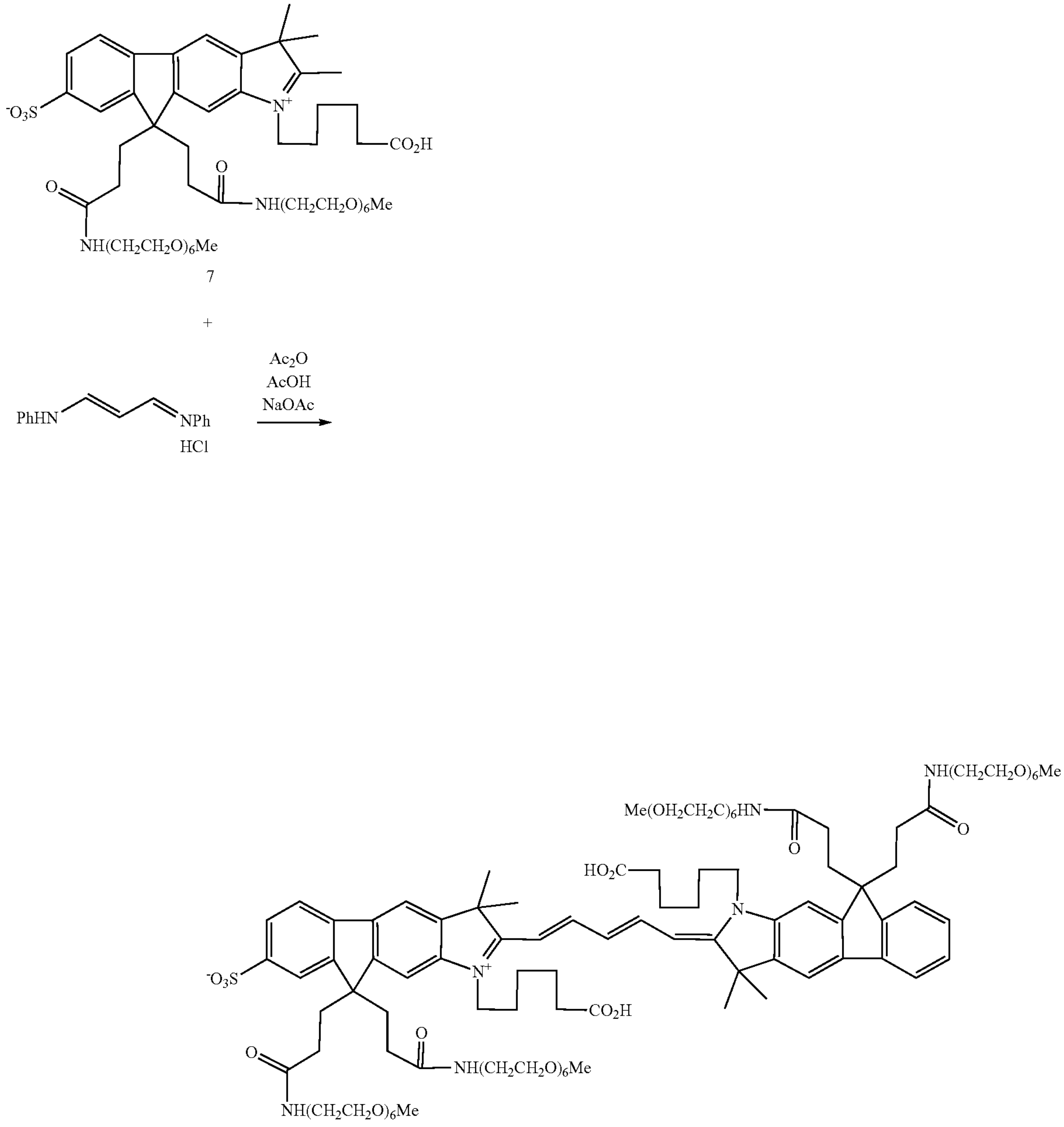

7

+

23

Compound 7 (114 mg) and malonaldehyde dinanilide hydrochloride (25.8 mg) were dissolved in AcOH (2 mL) and $Ac_2O$ (2 mL) and refluxed at 120° C. for 30 minutes. The reaction was cooled to 60° C. and then more compound 7 (114 mg) and NaOAc (41 mg) were added to the reaction. The reaction was refluxed at 120° C. for 1 hour. The deep blue solution was cooled to room temperature and concentrated at reduced pressure. The mixture was purified by preparative HPLC to give pure compound 23 (60 mg).

Example 24: Synthesis of Compound No. 24

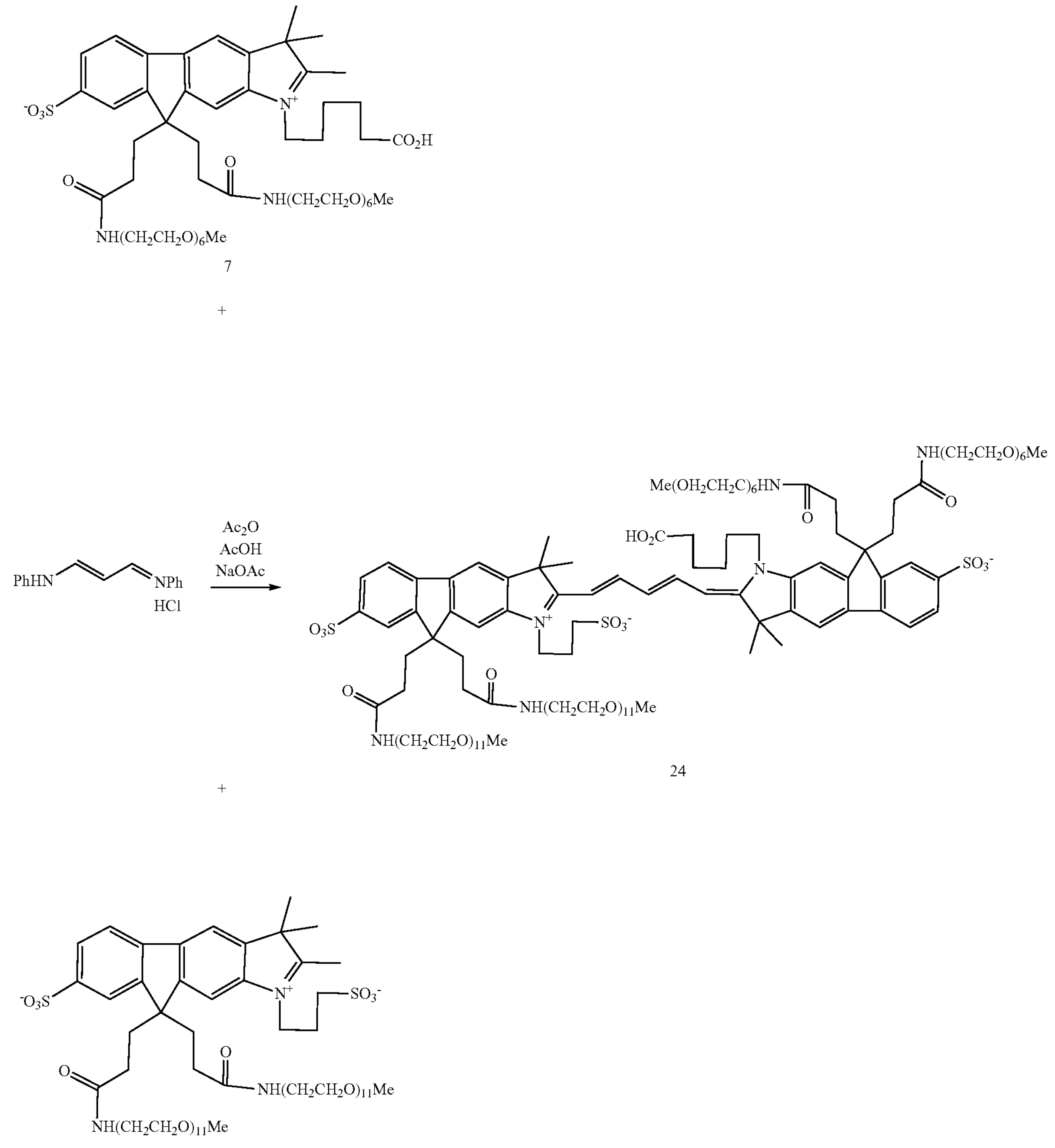

7

+

+

24

15

Compound 7 (114 mg) and malonaldehyde dinanilide hydrochloride (25.8 mg) were dissolved in AcOH (2 mL) and $Ac_2O$ (2 mL) and refluxed at 120° C. for 30 minutes. The reaction was cooled to 60° C. and then compound 15 (159 mg) and NaOAc (41 mg) were added to the reaction. The reaction was refluxed at 120° C. for 1 hour. The deep blue solution was cooled to room temperature and concentrated at reduced pressure. The mixture was purified by preparative HPLC to give pure compound 24 (75 mg).

Example 25: Synthesis of Compound No. 25

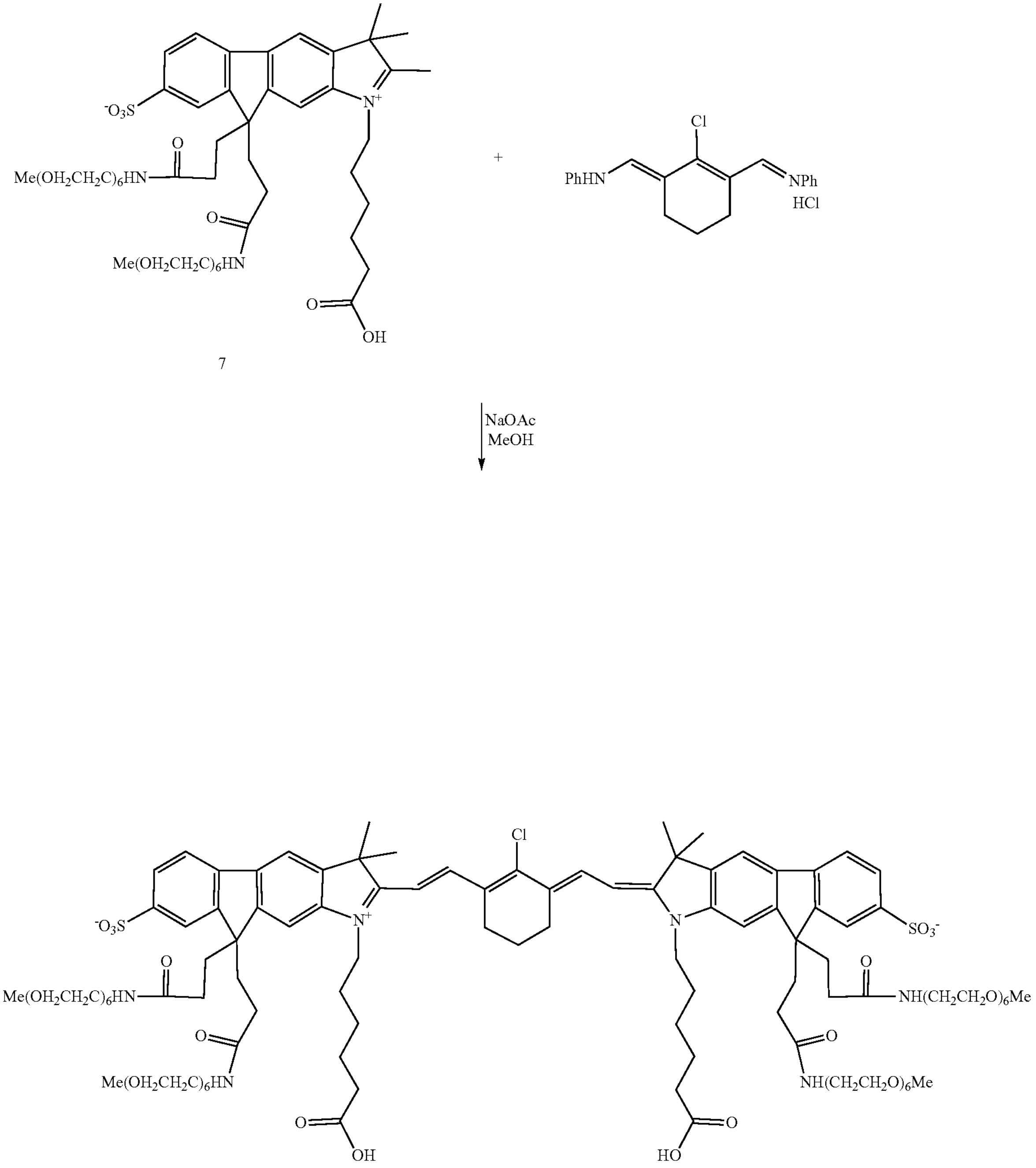

7

25

Compound 7 (60 mg), N-[(3-(Anilinomethylene)-2-chloro-1-cyclohexen-1-yl)methylene]aniline monohydrochloride (6.5 mg) and NaOAc (65 mg) were dissolved in MeOH (5 mL) and stirred at room temperature for 6 hours. The reaction was concentrated at reduced pressure. The mixture was purified by preparative HPLC to give pure compound 25 (20 mg).
Example 26: Synthesis of Compound No. 26
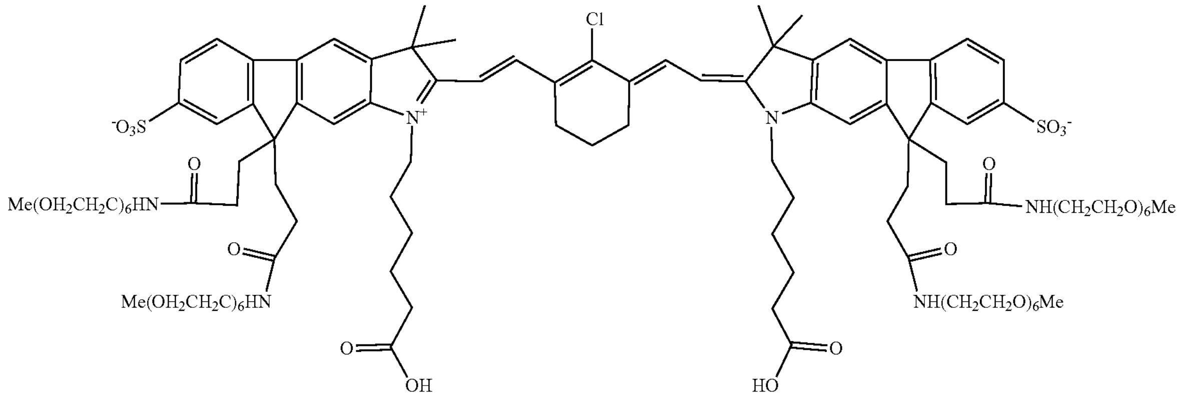
25
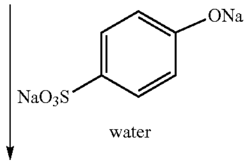
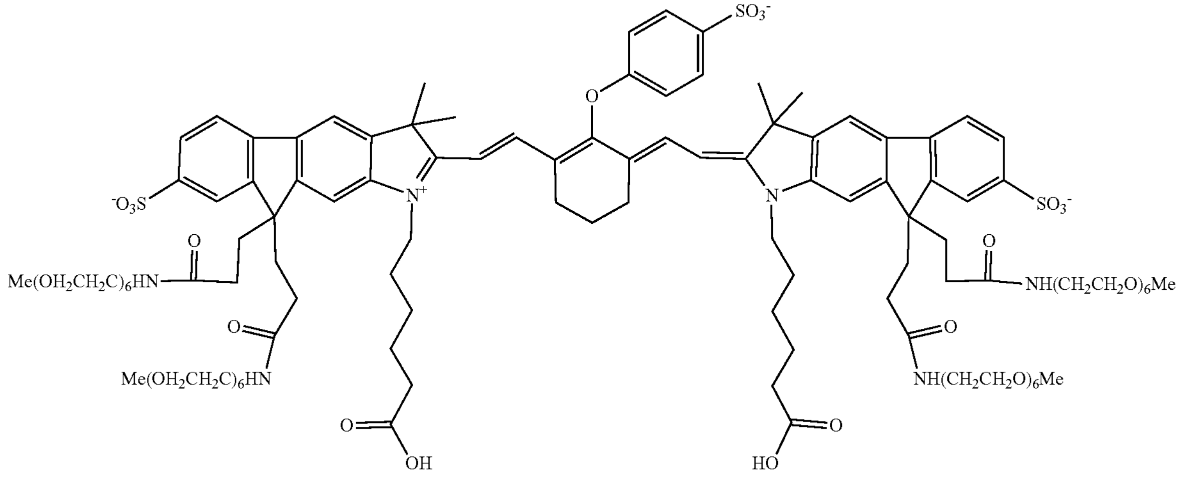
26

Compound 25 (18.3 mg) and sodium 4-oxidobenzenesulfonate (33 mg) were dissolved in water (0.5 mL) and heated at 60° C. for 6 hours. The mixture was purified by preparative HPLC to give pure compound 26 (8.3 mg).
Example 27: Synthesis of Compound No. 27
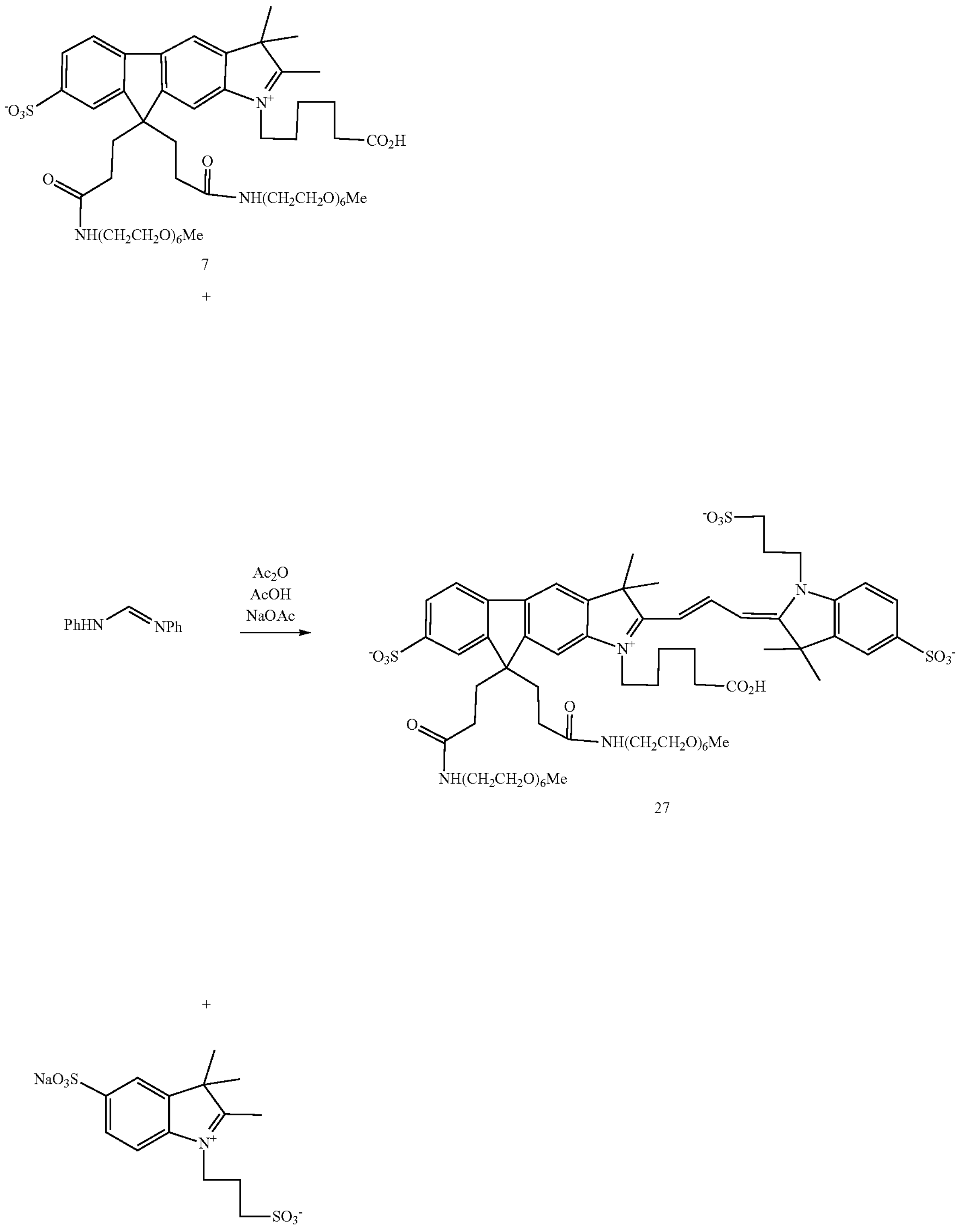
7 + + → 27

Compound 7 (48 mg) and N,N'-diphenylformamidine (40.2 mg) were dissolved in AcOH (0.5 mL) and $Ac_2O$ (0.5 mL) and refluxed at 120° C. for 30 minutes. The reaction was cooled to room temperature and pipetted into EtOAc (10 mL) with stirring. The yellow solid was filtered out of the solution and dried under vacuum. The yellow solid, NaOAc (17 mg), and 2,3,3-trimethyl-1-(3-sulfonatopropyl)-3H-indol-1-ium-5-sulfonate (15.8 mg) were dissolved in AcOH (0.5 mL) and $Ac_2O$ (0.5 mL) and the reaction was refluxed at 120° C. for 1 hour. The pink solution was cooled to room temperature and concentrated at reduced pressure. The mixture was purified by preparative HPLC to give pure compound 27 (14 mg).

Example 28: Synthesis of Compound No. 28

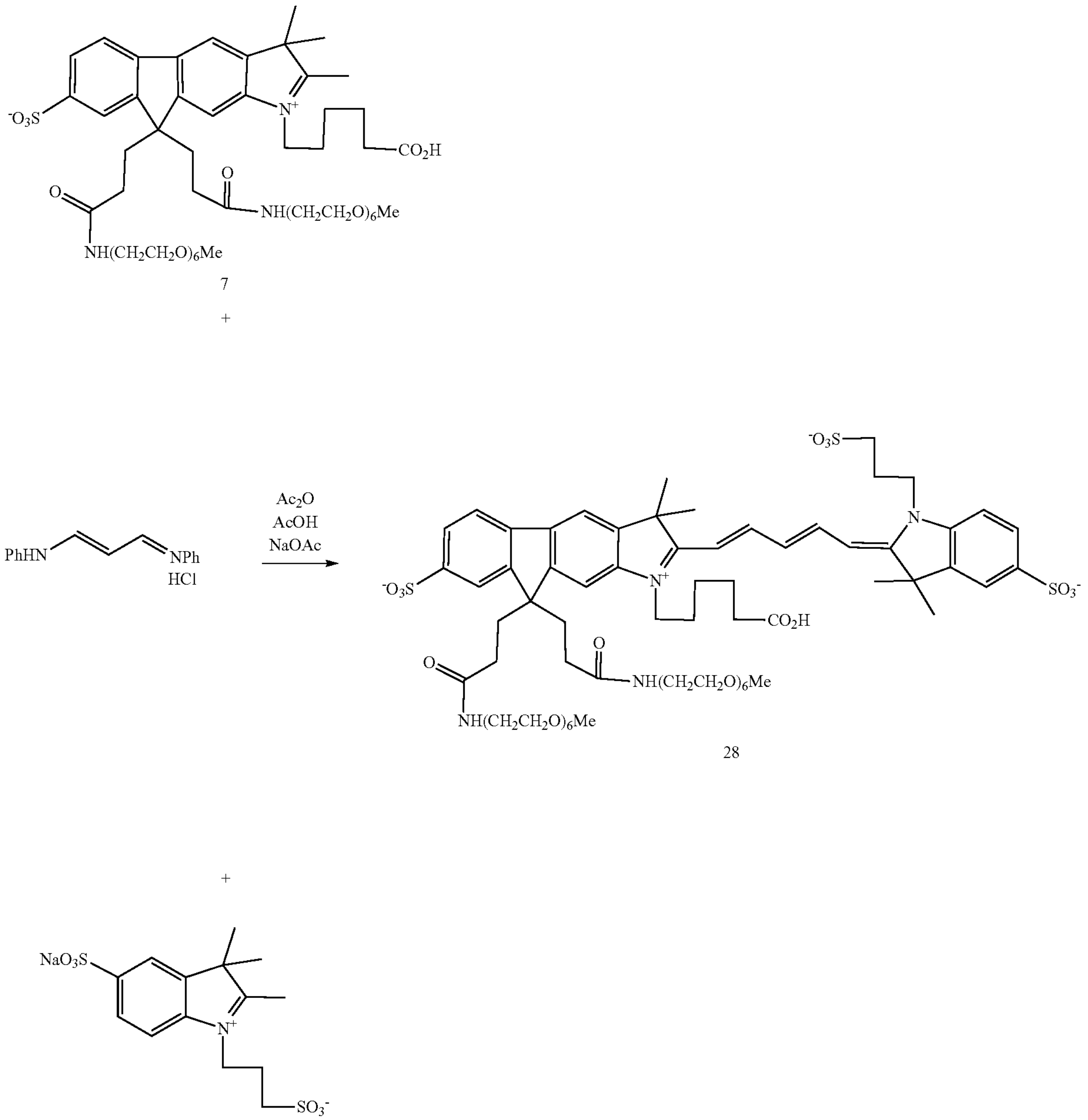

7

28

Compound 7 (48 mg) and malonaldehyde dinanilide hydrochloride (10.6 mg) were dissolved in AcOH (0.5 mL) and $Ac_2O$ (0.5 mL) and refluxed at 120° C. for 30 minutes. The reaction was cooled to 60° C. and then 2,3,3-trimethyl-1-(3-sulfonatopropyl)-3H-indol-1-ium-5-sulfonate (15.8 mg) and NaOAc (17 mg) were added to the reaction. The reaction was refluxed at 120° C. for 1 hour. The deep blue solution was cooled to room temperature and concentrated at reduced pressure. The mixture was purified by preparative HPLC to give pure compound 28 (20 mg).

Example 29: Synthesis of Compound No. 29

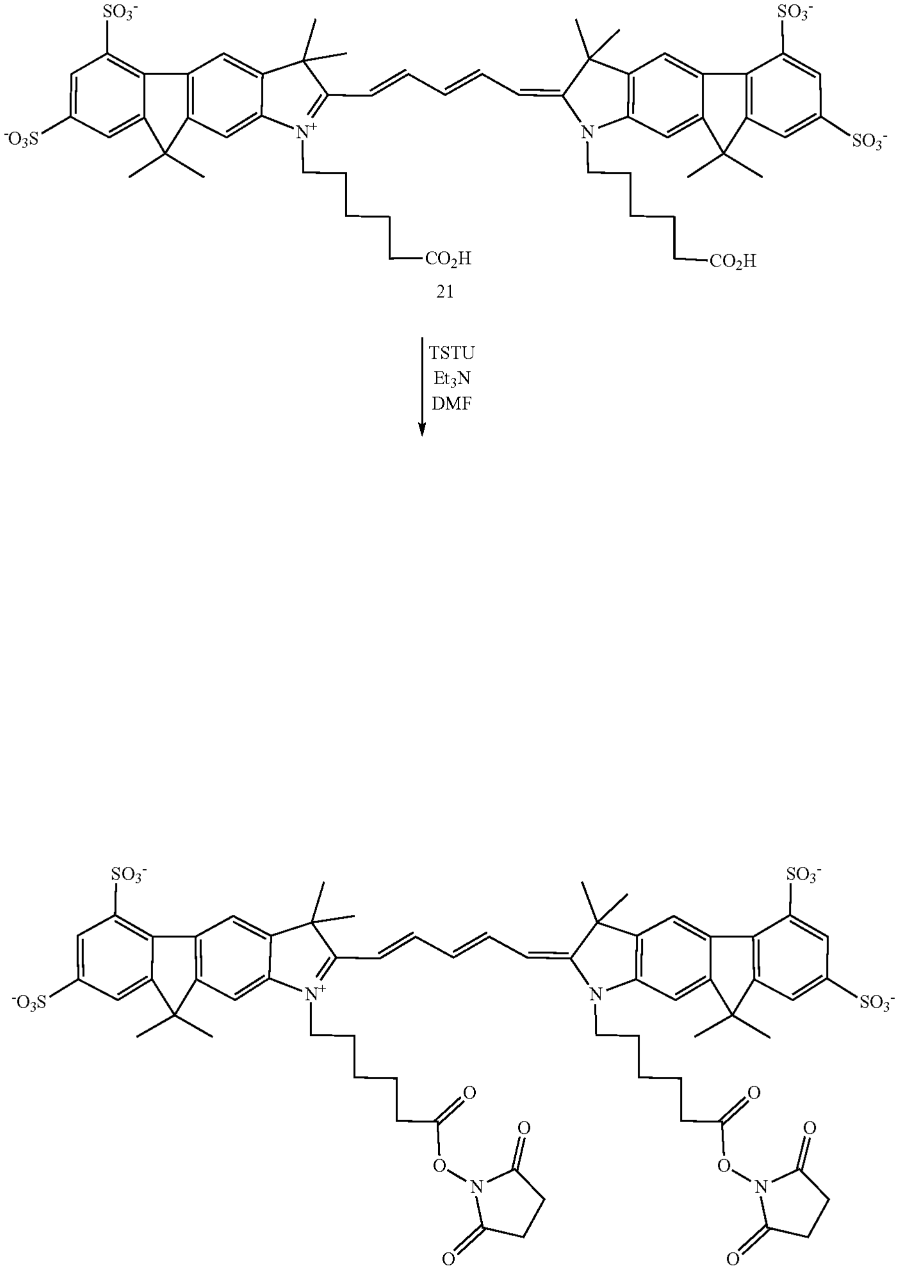

21

29

To a solution of compound 21 (16 mg) in DMF (0.5 mL) and $Et_3N$ (20 uL) was added TSTU (4.3 mg). The reaction was stirred for 15 minutes at room temperature. TLC (silica, 8/2, MeCN/water) showed complete conversion of compound 21 to a higher $R_f$ spot. The reaction was concentrated at reduced pressure. The blue residue was stirred with ether for several hours to remove any excess DMF. The ether layer was decanted and the residue was dried at reduced pressure to give compound 29 as a blue solid (16 mg). Compound 29 was shown to be readily reactive with primary amine containing compounds.

Example 30: Synthesis of Compound No. 30

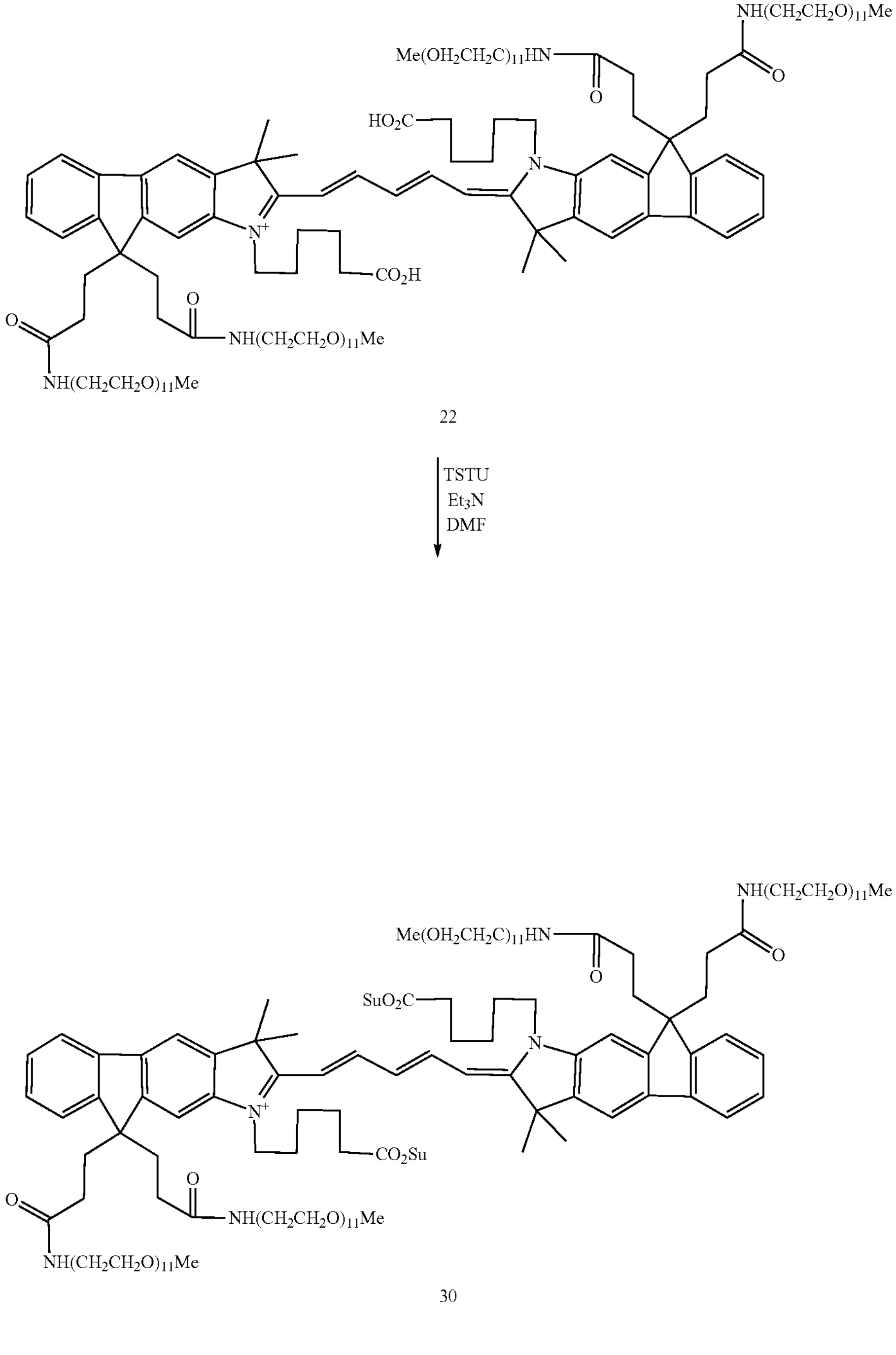

22

30

To a solution of compound 22 (19 mg) in DMF (0.5 mL) and $Et_3N$ (8.8 uL) was added TSTU (1.9 mg). The reaction was stirred for 15 minutes at room temperature. TLC (silica, 8/2, MeCN/water) showed complete conversion of compound 22 to a higher $R_f$ spot. The reaction was concentrated at reduced pressure. The blue residue was stirred with ether for several hours to remove any excess DMF. The ether layer was decanted and the residue was dried at reduced pressure to give compound 30 as a blue solid (19 mg). Compound 30 was shown to be readily reactive with 1° amine containing compounds.

Example 31: Synthesis of Compound No. 31

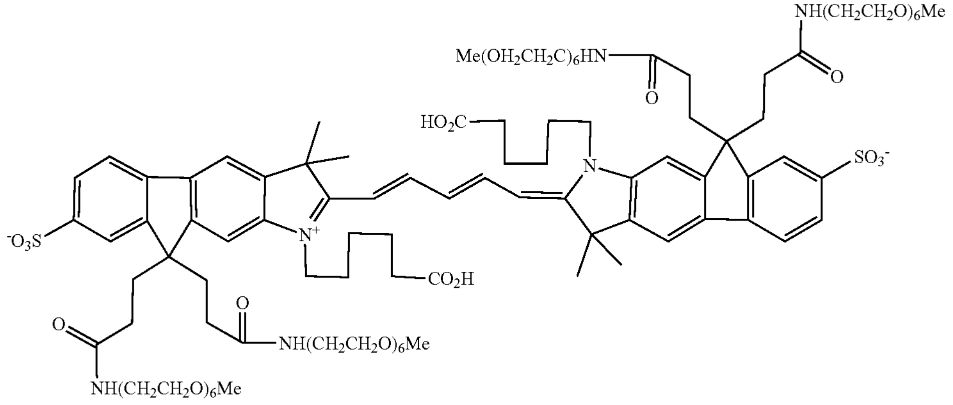

23

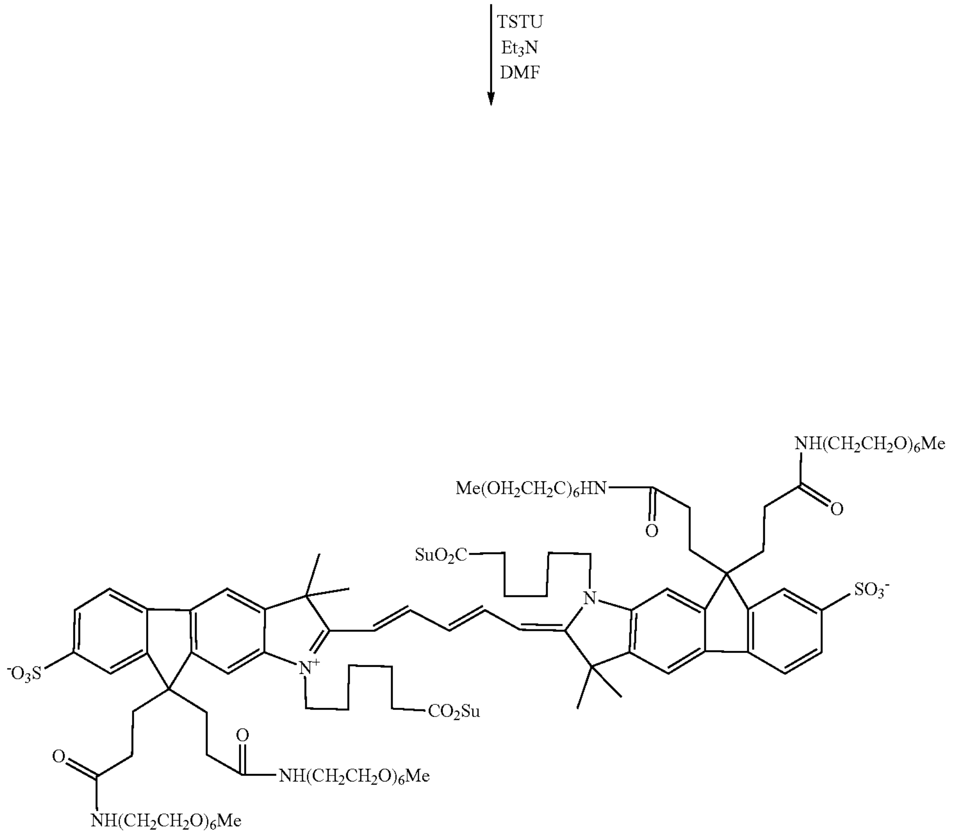

31

To a solution of compound 23 (55 mg) in DMF (1 mL) and $Et_3N$ (33 uL) was added TSTU (7.2 mg). The reaction was stirred for 15 minutes at room temperature. TLC (silica, 8/2, MeCN/water) showed complete conversion of compound 23 to a higher $R_f$ spot. The reaction was concentrated at reduced pressure. The blue residue was stirred with ether for several hours to remove any excess DMF. The ether layer was decanted and the residue was dried at reduced pressure to give compound 31 as a blue solid (53 mg). Compound 31 was shown to be readily reactive with 1° amine containing compounds.

Example 32: Synthesis of Compound No. 32

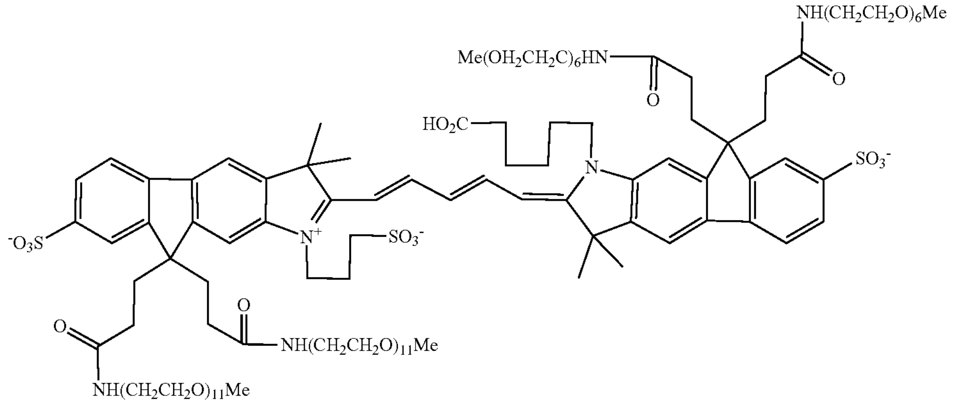

24

TSTU
$Et_3N$
DMF

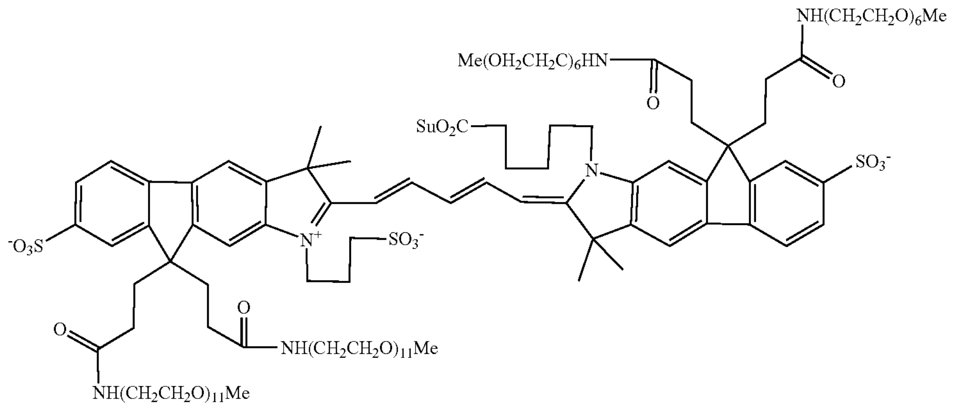

32

To a solution of compound 24 (68 mg) in DMF (1 mL) and $Et_3N$ (17.2 uL) was added TSTU (7.5 mg). The reaction was stirred for 15 minutes at room temperature. TLC (silica, 8/2, MeCN/water) showed complete conversion of compound 24 to a higher $R_f$ spot. The reaction was concentrated at reduced pressure. The blue residue was stirred with ether for several hours to remove any excess DMF. The ether layer was decanted and the residue was dried at reduced pressure to give compound 32 as a blue solid (60 mg). Compound 32 was shown to be readily reactive with 1° amine containing compounds.

Example 33: Synthesis of Compound No. 33

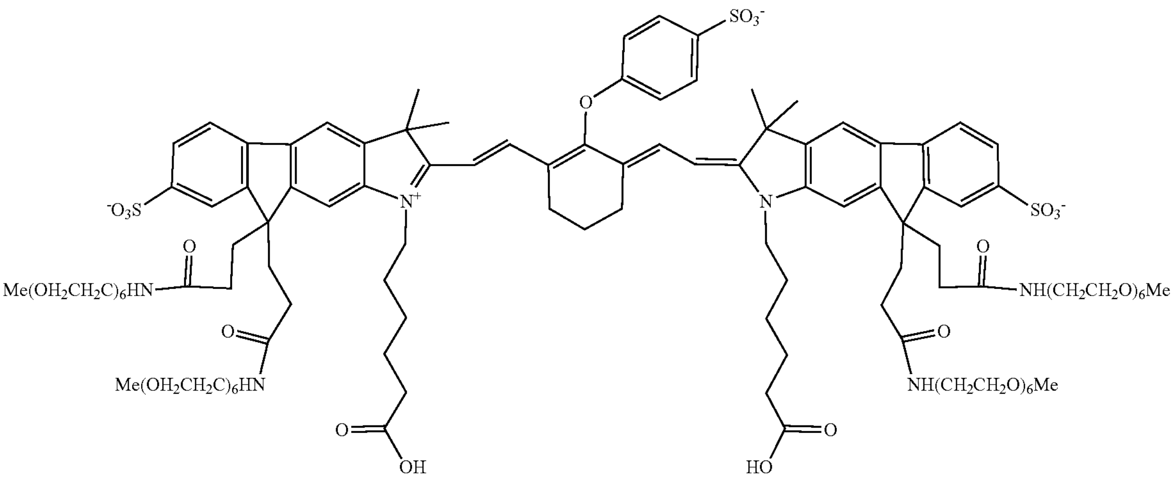

26

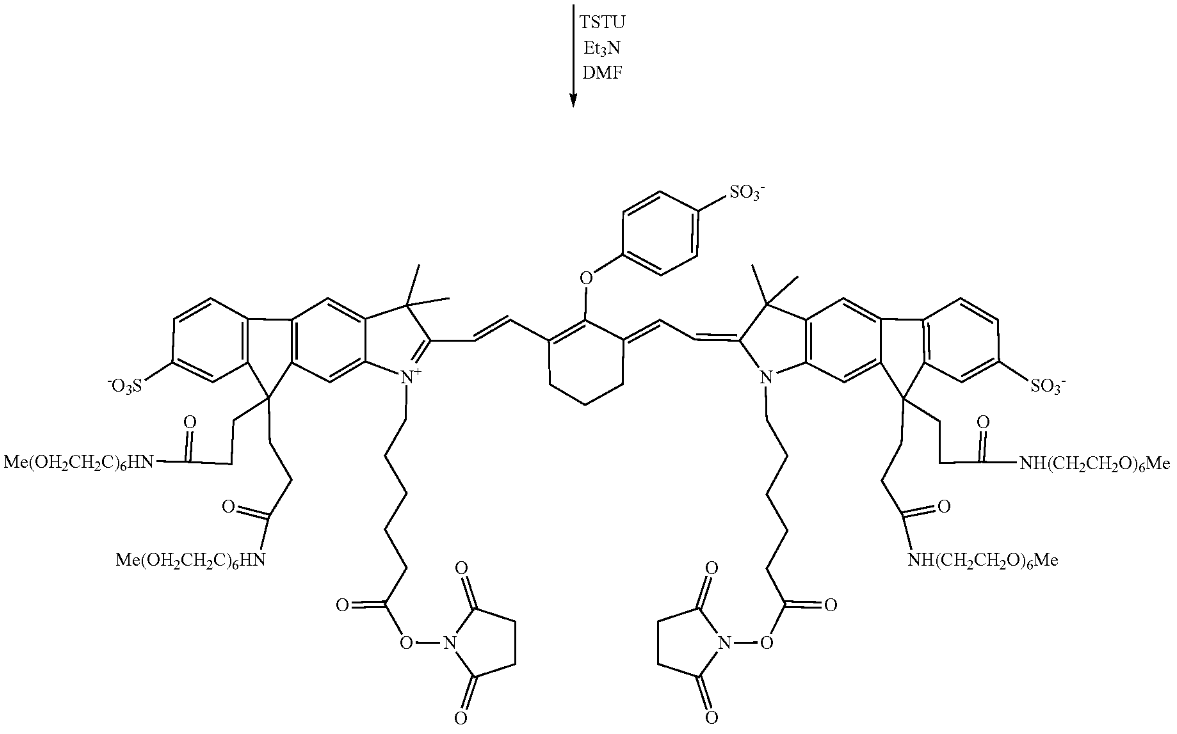

33

To a solution of compound 26 (7 mg) in DMF (0.3 mL) and $Et_3N$ (3.8 uL) was added TSTU (1.0 mg). The reaction was stirred for 15 minutes at room temperature. TLC (silica, 8/2, MeCN/water) showed complete conversion of compound 26 to a higher $R_f$ spot. The reaction was concentrated at reduced pressure. The green residue was stirred with ether for several hours to remove any excess DMF. The ether layer was decanted and the residue was dried at reduced pressure to give compound 33 as a green solid (7 mg). Compound 33 was shown to be readily reactive with 1° amine containing compounds.

Example 34: Synthesis of Compound No. 34

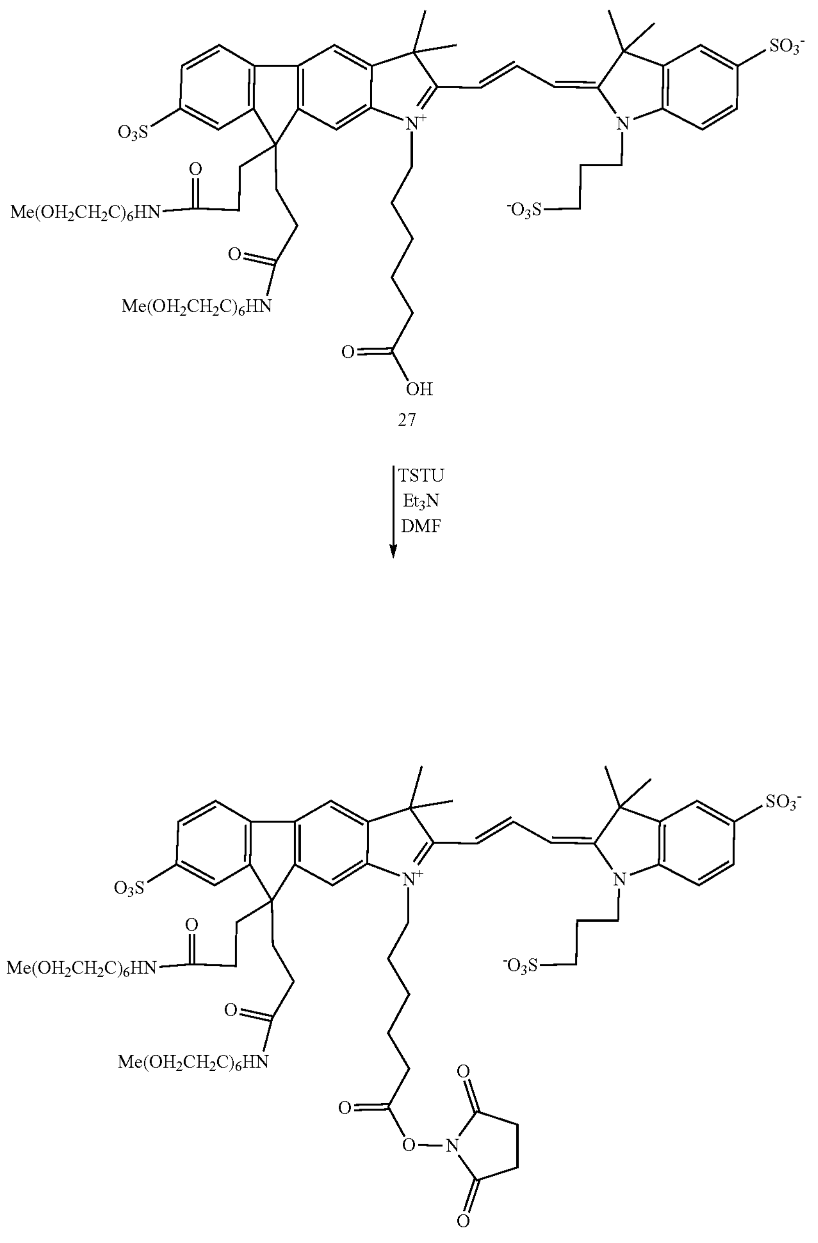

27

34

To a solution of compound 27 (13 mg) in DMF (0.5 mL) and $Et_3N$ (6 μL) was added TSTU (2.6 mg). The reaction was stirred for 15 minutes at room temperature. TLC (silica, 8/2, MeCN/water) showed complete conversion of compound 27 to a higher Rfspot. The reaction was concentrated at reduced pressure. The pink residue was stirred with ether for several hours to remove any excess DMF. The ether layer was decanted and the residue was dried at reduced pressure to give compound 34 as a pink solid (13 mg). Compound 34 was shown to be readily reactive with 1° amine containing compounds.

Example 35: Synthesis of Compound No. 35

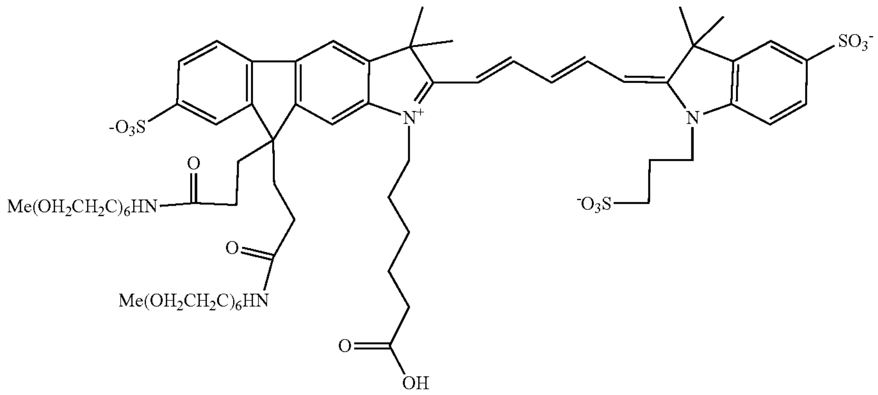

28

TSTU
$Et_3N$
DMF

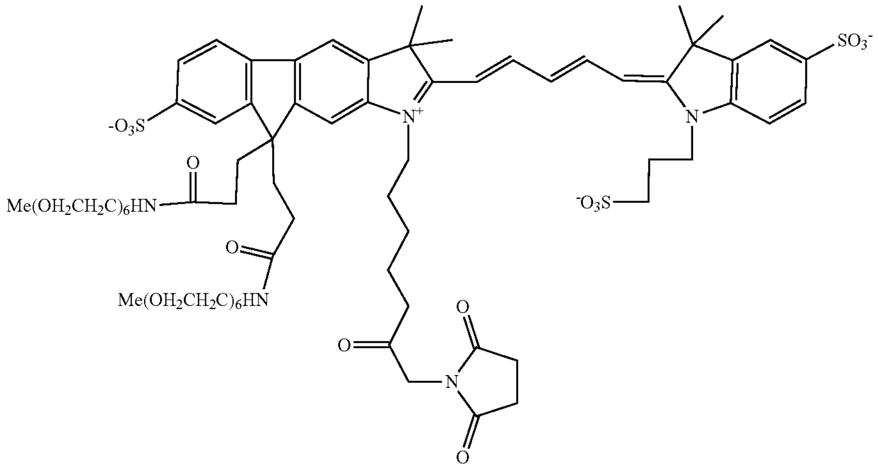

35

To a solution of compound 28 (19 mg) in DMF (0.5 mL) and $Et_3N$ (8.7 μL) was added TSTU (3.8 mg). The reaction was stirred for 15 minutes at room temperature. TLC (silica, 8/2, MeCN/water) showed complete conversion of compound 28 to a higher $R_f$ spot. The reaction was concentrated at reduced pressure. The blue residue was stirred with ether for several hours to remove any excess DMF. The ether layer was decanted and the residue was dried at reduced pressure to give compound 35 as a blue solid (19 mg). Compound 35 was shown to be readily reactive with 1° amine containing compounds.

Example 36: Preparation of Protein Dye-Conjugates

Fluorescent conjugates of goat anti-mouse IgG (GAM), goat anti-rabbit IgG (GAR), and streptavidin were prepared from the respective proteins and a reactive dye, following published procedures (U.S. Pat. No. 6,974,873; Haugland et al., *Meth. Mol. Biol.* 45, 205(1995); Haugland et al., *Meth. Mol. Biol.* 45, 223(1995); Haugland et al., *Meth. Mol. Biol.* 45, 235(1995); Haugland et al., *Current Protocols in Cell Biology,* 16.5.1-16.5.22(2000)). Briefly, an antibody or streptavidin at 1 mg/mL in 0.1 mM pH 8.5 sodium bicarbonate buffer was mixed with one of the reactive dye at various ratio of dye molecules/protein molecule. After incubating for about an hour at room temperature, the reaction mixture was separated by gel filtration using Sephadex G-25 equilibrated with PBS (pH 7.4).

Example 37: Preparation of an Oligonucleotide Dye-Conjugate

To a 5'-amine-modified, 18-base M13 primer sequence (100 μg) in $H_2O$ (4 μL) is added a solution of compound No. 10 (500 μg) in 0.1M sodium borate pH=8.5 buffer (200 μL). The mixture is stirred at room temperature overnight and 3 volumes of cold ethanol are added. The mixture is cooled to −20° C., centrifuged, the supernatant is decanted, the pellet is rinsed with ethanol and then dissolved in $H_2O$ (100 μL). The labeled oligonucleotide is purified by preparative HPLC. The desired peak is collected and evaporated to give the fluorescent oligonucleotide.

Figure 2:
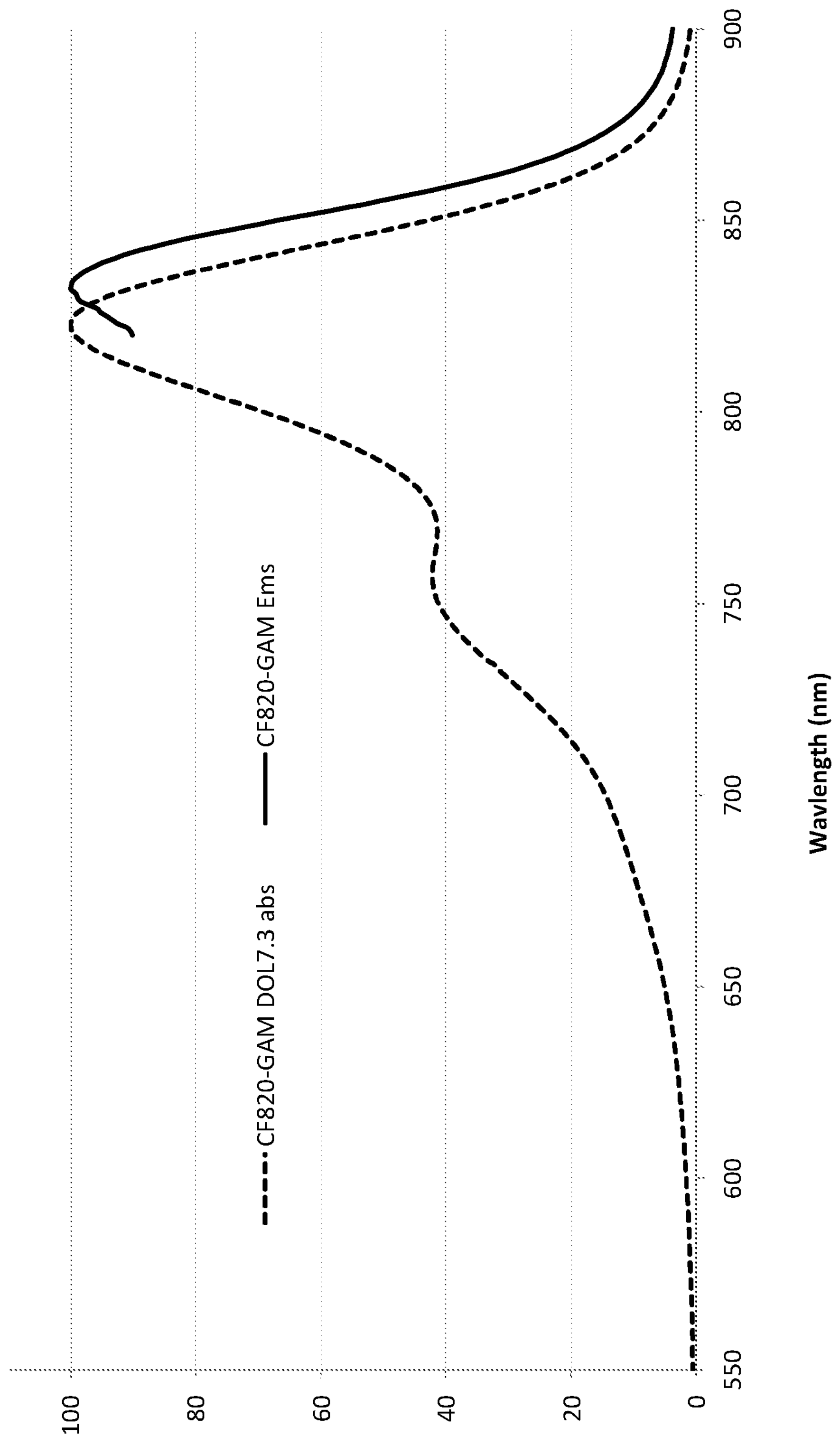
FIG. 2 shows absorption (dashed line) and emission (solid line) spectra of a compound of the invention conjugated to goat anti-mouse IgG.
Figure 3:
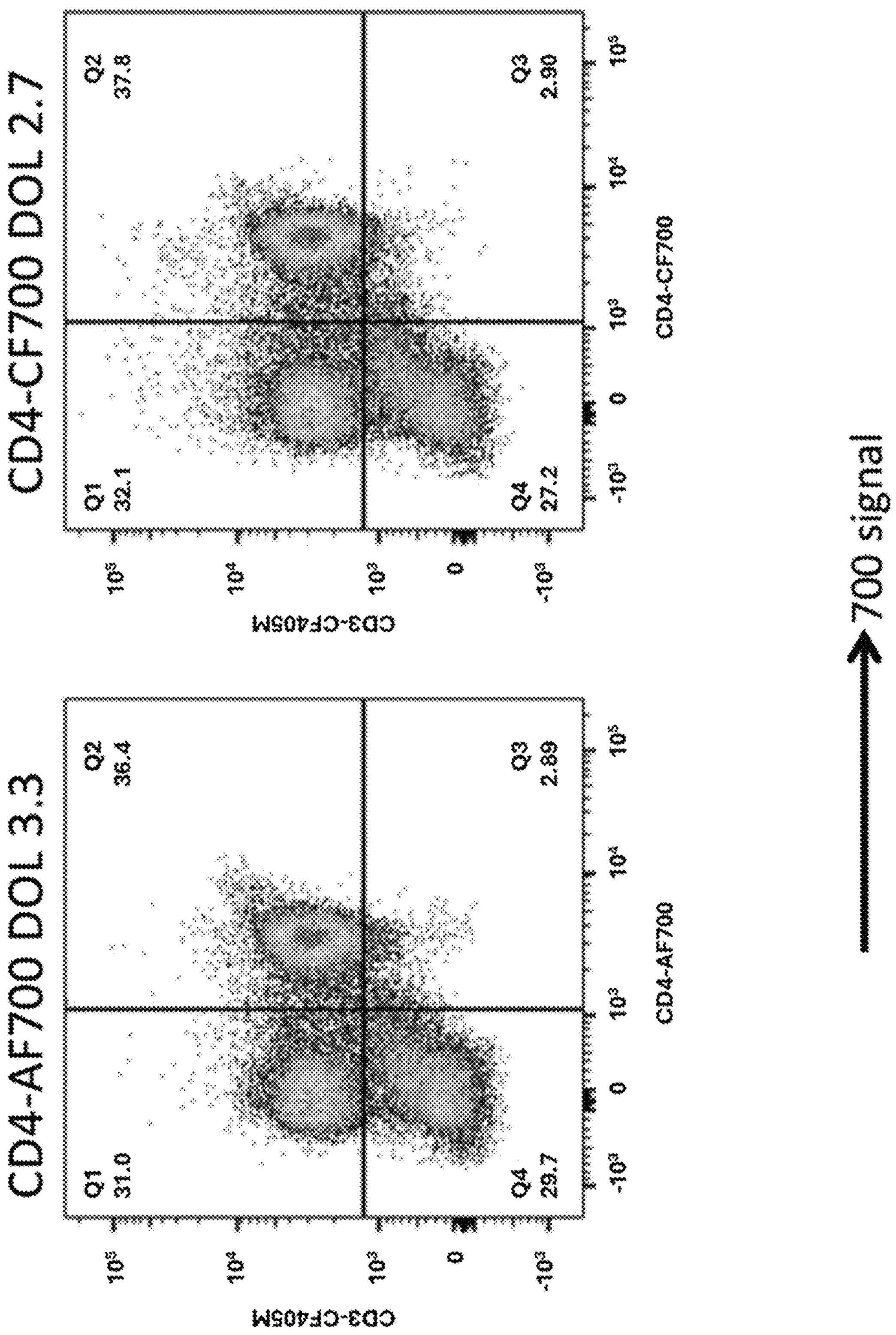
FIG. 3 is a graphical representation showing staining of peripheral blood mononuclear cells (PBMC) using anti-CD4 antibodies covalently conjugated with a compound of the invention relative to AF700, a prior art anti-CD4 conjugate.
Figure 4:
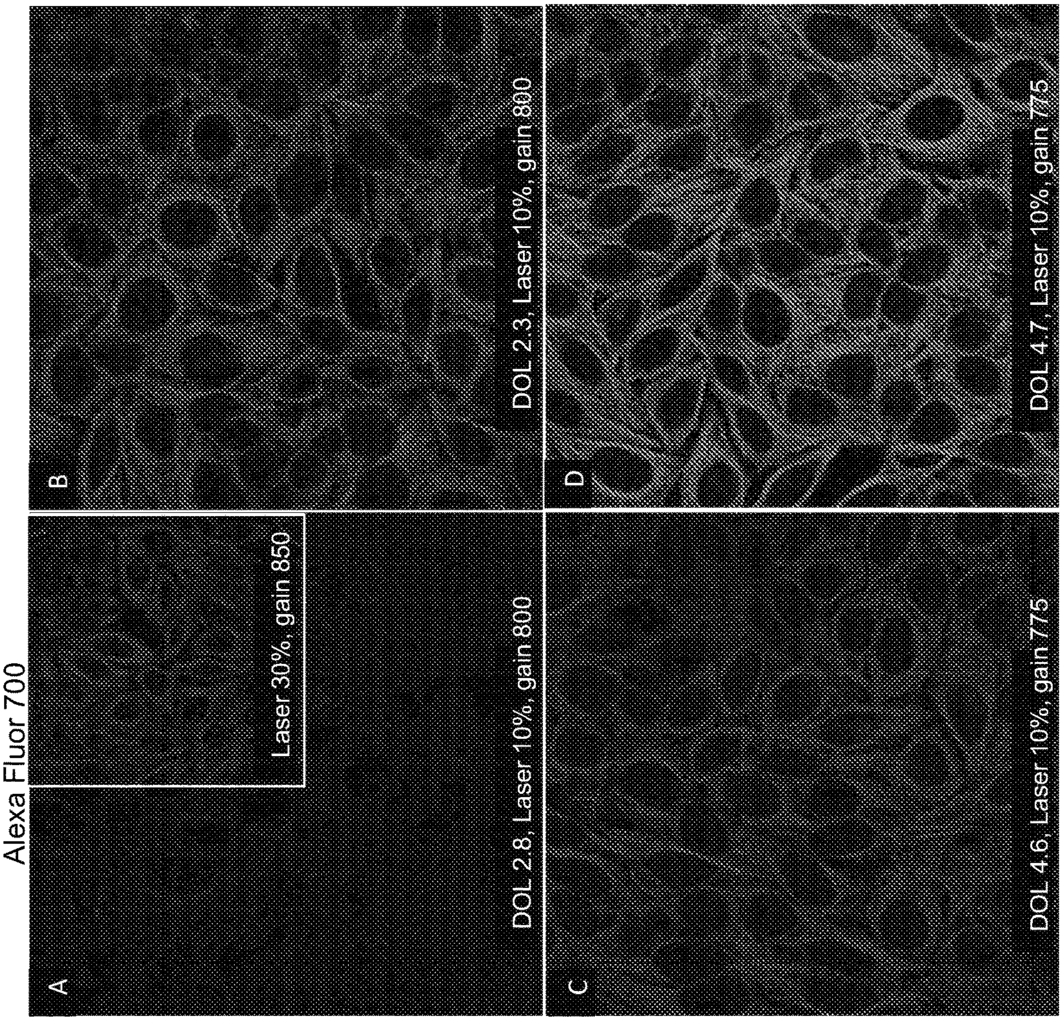
FIG. 4 shows microscopic images of HeLa cells fixed and stained with intracellular mouse anti-human tubulin antibodies (10 μg/mL) conjugated to a compound of the invention. Laser power, gain, and degree of labeling (DOL) are indicated at the bottom of each image. Panels A and C show data for AF700, and panels B and D show the compound of the invention. The inset in panel A shows the same field of view imaged using higher laser power and gain setting to confirm the presence of specific signal.
Figure 5:
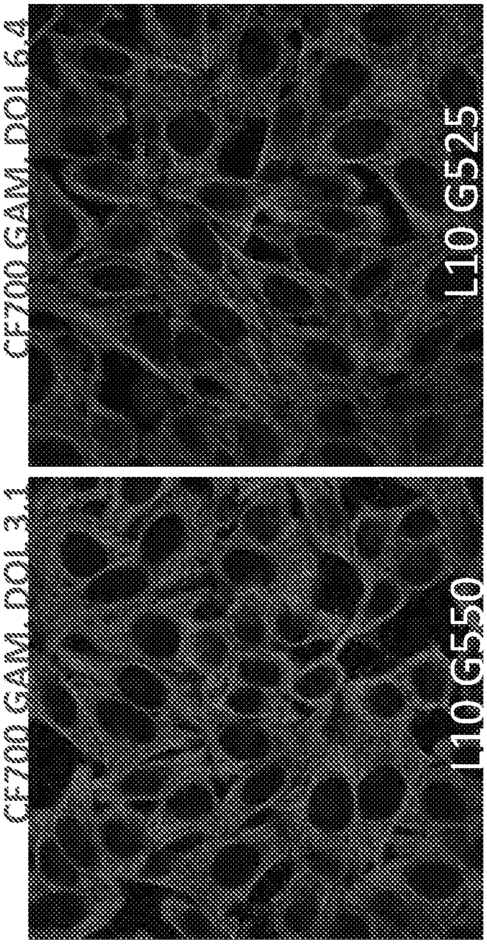
FIG. 5 shows microscopic images of HeLa cells fixed and stained with intracellular mouse anti-human tubulin antibodies (10 μg/mL) conjugated to a compound of the invention. Laser power and gain are indicated at the bottom of each image, and the degree of labeling (DOL) is shown at the top.
Figure 6:
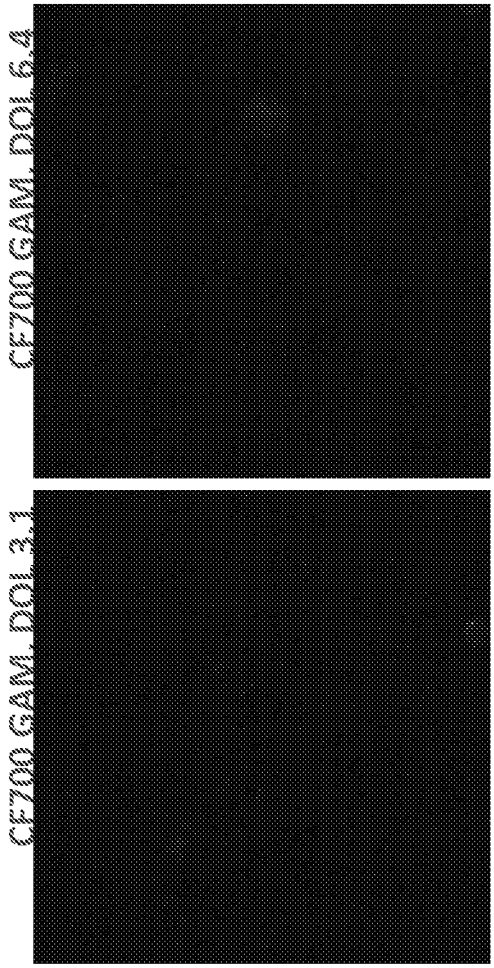
FIG. 6 shows a test of background fluorescence under the conditions of FIG. 5, using 10 μg/mL antibody concentration and no primary antibody; background fluorescence is very low.
Figure 7:
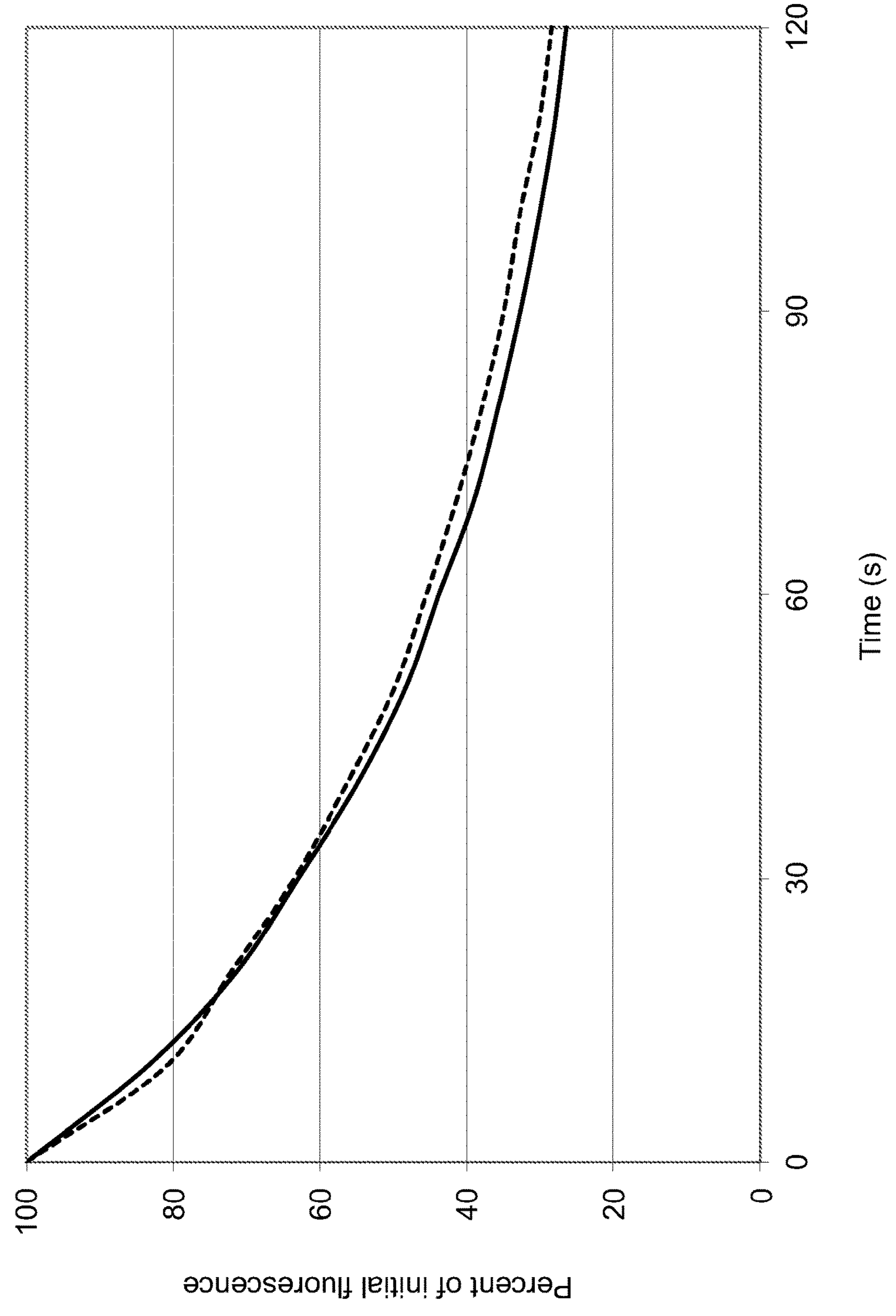
FIG. 7 shows a test of photostability of the antibody-dye conjugates used in FIG. 5 at DOL 3.1 (solid line) and DOL 6.4 (dashed line).
Figure 8:
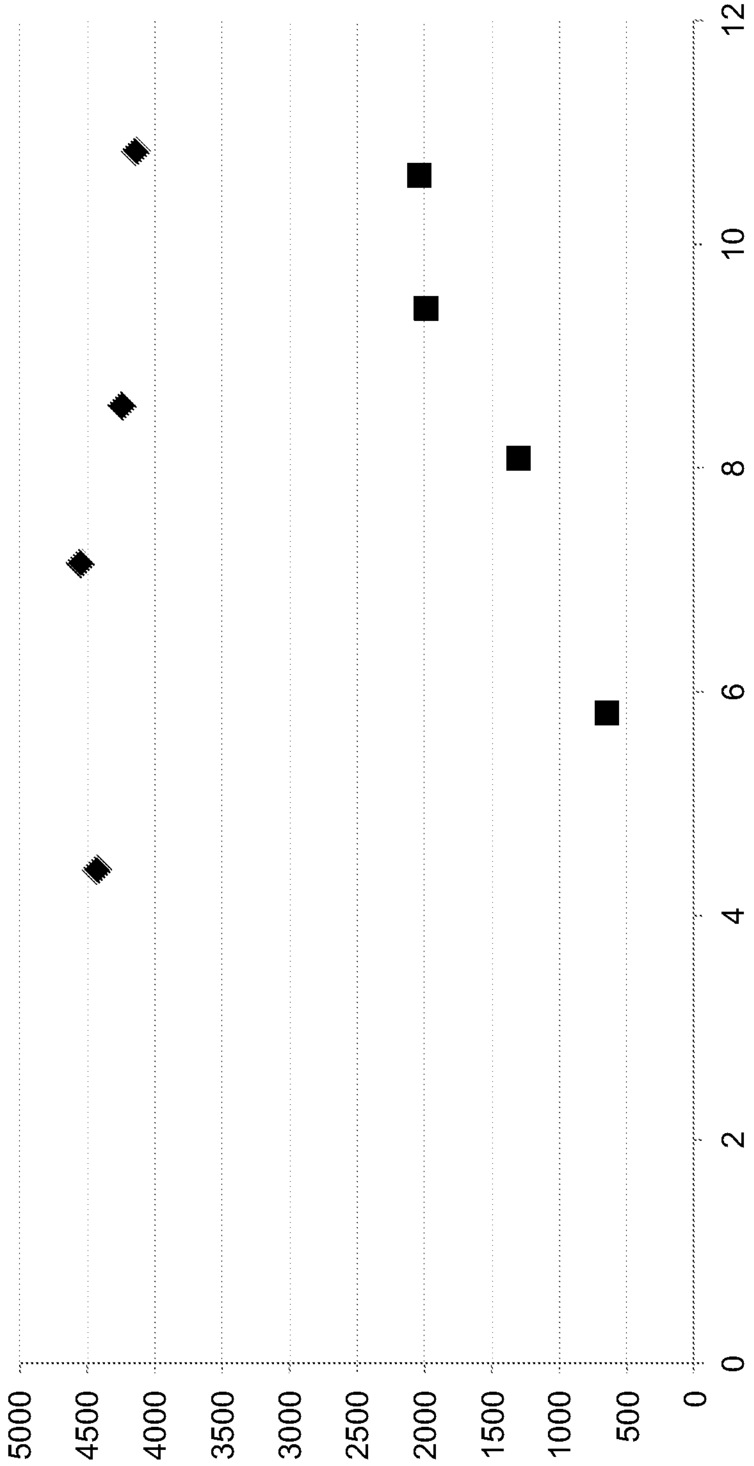
FIG. 8 shows peak emission fluorescence of an antibody-dye conjugate of the invention relative to prior art conjugate of DyLight™ 800 at equivalent degree of labeling.
Figure 9:
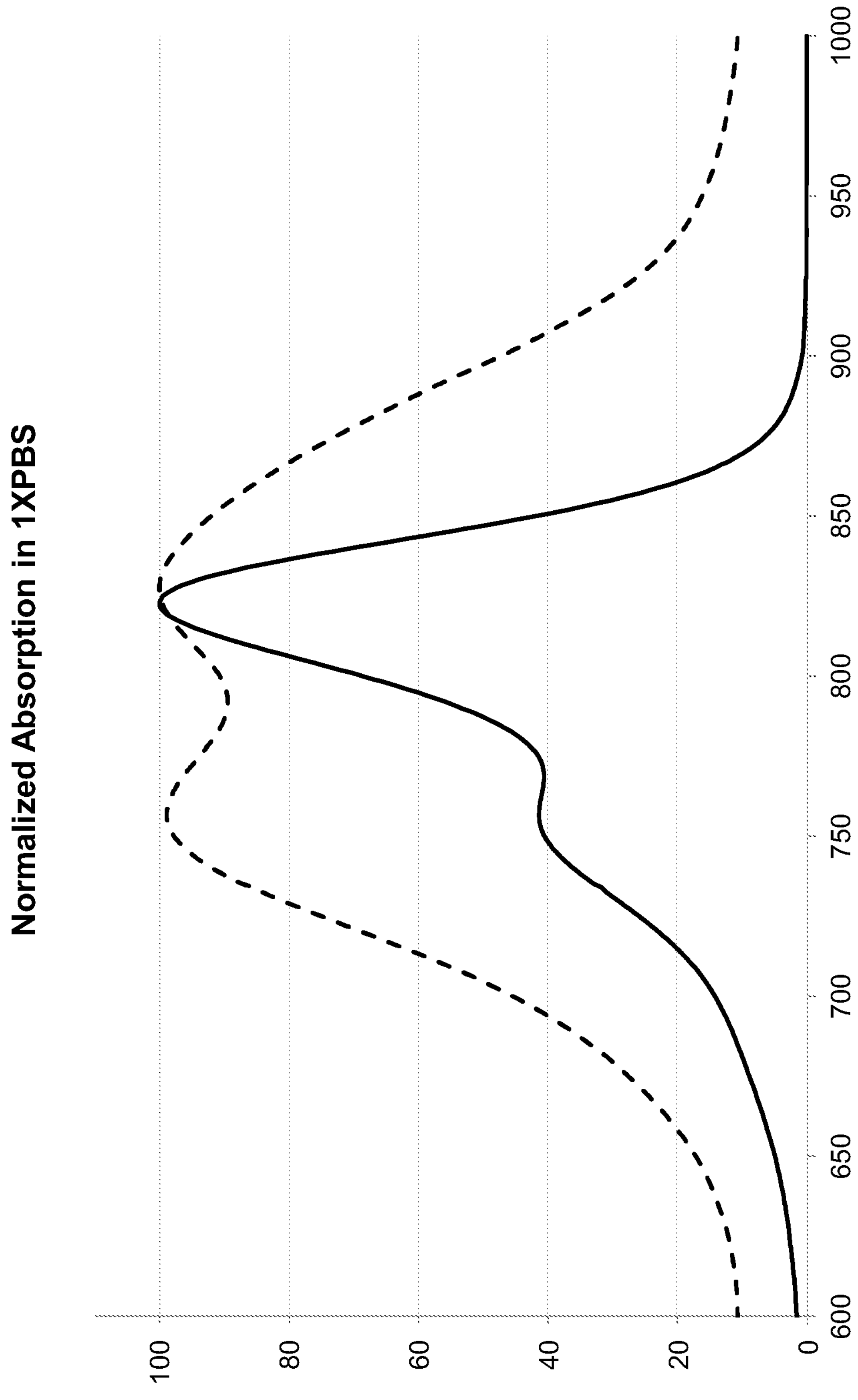
FIG. 9 shows normalized emission spectra in 1×PBS of the dye conjugates of FIG. 8 (solid line: compound of the invention; dashed line: DyLight™ 800).

Example 38: Flow Cytometry Analysis of Cells Intracellularly Stained with Dye-Antibody Conjugates One million Jurkat cells were fixed, permeabilized and stained with IgG1 isotype or intracellular mouse anti-human CD3 primary antibody (0.375 ug) followed by 1 ug of goat-anti-mouse conjugated to AlexaFluor700 or a compound of the invention. Fluorescence was detected on a BD FACS Calibur flow cytometer using the FL4 channel. The results are shown in FIG. 2, where the bars represent the fluorescence geometric means of the populations stained with isotype control (black bars) or CD3 (white bars) antibody. The data are also plotted as signal-to-noise ratio (i.e., relative fluorescence geometric means of the CD3 stained cell population over the respective isotype controls) vs. DOL in FIG. 3.

Example 39. PBMC Staining Using Flow Cytometry

Cryopreserved human PBMC cells were thawed and cultured overnight at 37° C. according to standard protocols. Cells were collected by centrifugation, washed, and resuspended in FACS buffer (PBS/2% FBS/0.1% sodium azide). For each sample, 1 million cells in 1 mL FACS buffer were incubated with 0.5 μg/tube of a compound of the invention or Alexa Fluor 700 monoclonal mouse anti-CD4 conjugate (helper T-cell marker) for 30 minutes on ice. In some experiments, CF405 monoclonal mouse anti-CD3 conjugate was used to label all T-cells. After staining, cells were collected by centrifugation, washed once with FACS buffer, and resuspended in 1 mL FACS buffer. Fluorescence was measured for 10,000 events in the Alexa Fluor 700 channel of a BD LSRII flow cytometer (633 nm laser, 685 nm long-pass filter, 710/50 nm bandpass filter).

Example 40: Immunofluorescence Staining and Photostability Measurements

HeLa cells were cultured in coverglass-bottom 96-well plates. One to three days after seeding, cells were rinsed with HBSS buffer, fixed with ice-cold methanol at −20° C. for 5-10 minutes, and rinsed with PBS. Cells were stored at 4° C. in PBS with 0.02% sodium azide before staining. Cells were blocked for 30 minutes at room temperature in PBS with 2% fish gelatin, 0.01% Triton X-100, 0.02% sodium azide, then incubated for 2 hours at room temperature with 2 μg/mL monoclonal mouse-anti-tubulin antibody diluted in the same buffer used for blocking. Control cells with no primary antibody were left in blocking buffer. Cells were rinsed twice with PBS, then washed three times for five minutes per wash with PBS. Cells were incubated with secondary antibodies diluted in the same buffer used for blocking for 1-2 hours at room temperature. Secondary antibodies were used at 2 μg/mL or 10 μg/mL. Cells were rinsed twice with PBS, then washed three times for five minutes per wash with PBS. Cells were imaged in PBS on a Zeiss LSM700 confocal imaging system, or on an Olympus IX71 epifluorescence microscope using the Q-Imaging Retiga 2000R digital camera and ImagePro Express v 6.0. For photostability measurements, fluorescence was imaged every 10 seconds for 120 seconds, and the mean fluorescence intensity at each time point was recorded. Results are shown in FIGS. 4-7. Goat anti-mouse conjugates prepared using compounds of the invention showed markedly brighter signal compared to Alexa Fluor 700 goat anti-mouse conjugates at comparable degree of labeling (DOL) values. The presence of specific signal was confirmed using a higher laser power and gain setting. Background fluorescence of secondary antibody in the absence of primary antibody was very low for all conjugates, even at higher laser power and gain setting.

Example 41. Western Blots Using Dye Conjugates

Figure 10:
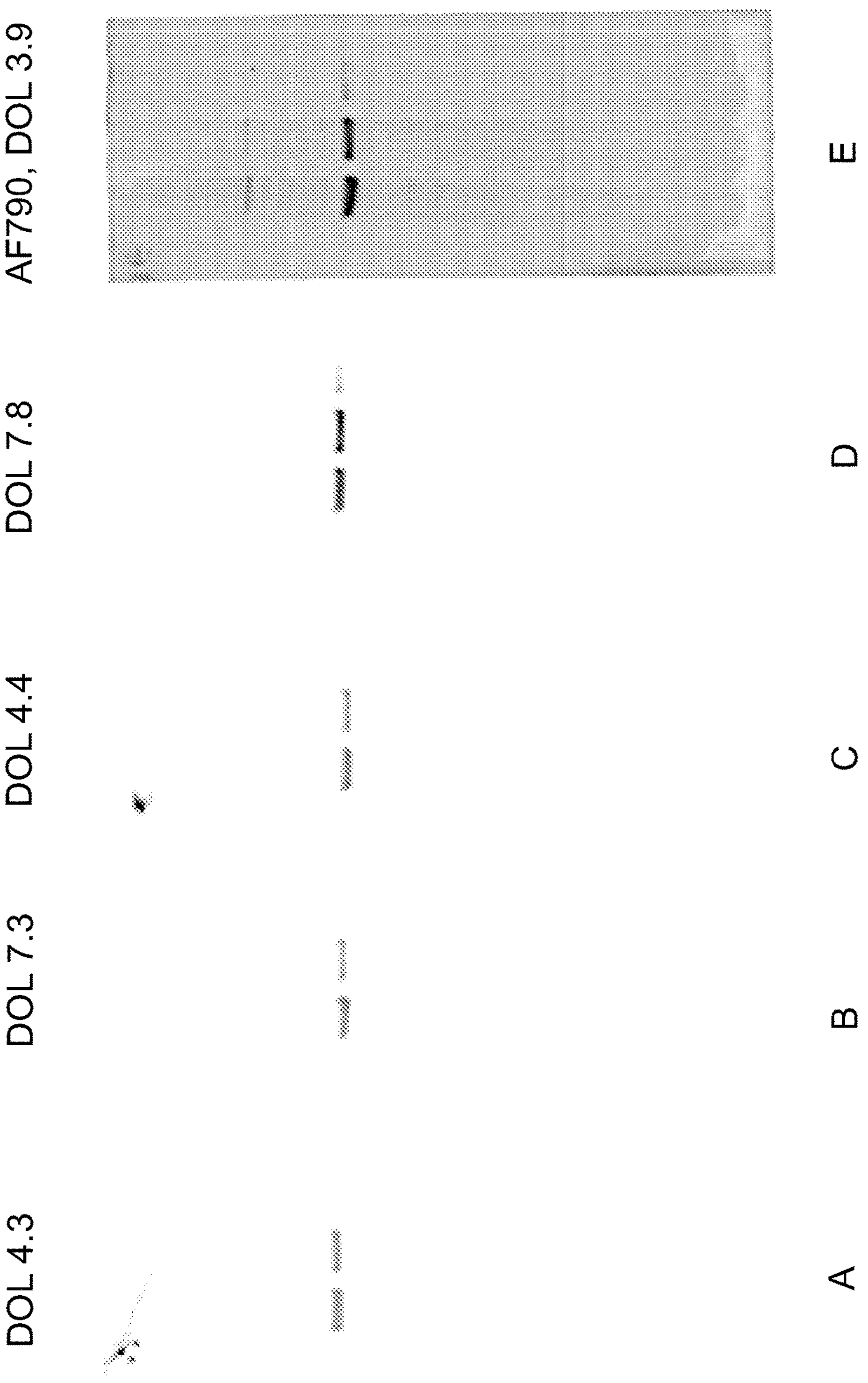
FIG. 10 shows Western Blots obtained using dye conjugates of the invention (panels A-D) as well as using a prior art dye conjugate (AlexaFluor 790, panel E).

Western Blots were run using standard methods in the art. Briefly, HeLa cells were lysed and diluted to 1, 0.1, and 0.01 mg/mL. After adding LDS (lithium dodecyl sulfate), loading buffer and DTT (Dithiothreitol), 10 μL of lysate was loaded to each lane. SDS-PAGE gels were run using 4-12% Bis-Tris gel in 1×MES (2-(N-morpholino)ethanesulfonic acid) running buffer at 200V for 35 min. Protein bands were transferred to PVDF (Polyvinylidene fluoride) membranes using semi-dry transferring method. 2% fish gelatin in TBST was used as the blocking buffer, primary antibody binding buffer and secondary antibody binding buffer. TBST alone was used in the washing steps. Membranes were scanned at 800 nm on a LiCOR Odyssey instrument. Results (color inverted) are shown in FIG. 10. Specific signal with minimal background was observed using conjugates of the invention (A, B, C, D). A prior art dye conjugate was also tested (AlexaFluor790, E) and showed very high background fluorescence.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention d escribed herein may be employed in practicing the invention. It is intended that the following claims define the scope of the invention and that methods and structures within the scope of these claims and their equivalents be covered thereby.

What is claimed is:

1. A compound of Formula 1a or 1b:

Formula 1a

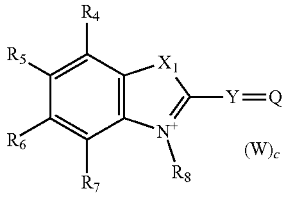

Formula 1b

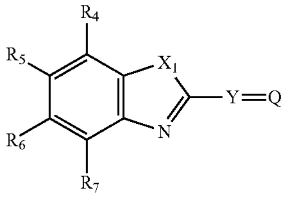

wherein:

$X_1$ is O, S, $NR_1$ or $CR_2R_3$;

$R_1$, $R_2$ and $R_3$ are independently substituted or unsubstituted alkyl, $(R)_p$—$(L)_q$—, or $R_2$ and $R_3$ taken together form a 3-8 membered ring optionally substituted by $(R)_p$-$(L)_q$—;

$R_4$, $R_5$, $R_6$, and $R_7$ are independently hydrogen, halo, —CN, alkoxy, alkyl, aryl, heteroaryl, amino, alkylamino, dialkylamino, alkanecarboxamido, alkanesulfonamido, aminocarbonyl, N-alkylaminocarbonyl, N,N-dialkylaminocarbonyl, N,N,N-trialkylammoniumalkyl, aminosufonyl, N-alkylaminosulfonyl, N,N-dialkylaminosulfonyl, phosphonyl, carboxylate, azide, nitro, arylazo, or $(R)_p$—$(L)_q$—;

at least one substituent pair of $R_4$ and $R_5$, $R_5$ and $R_6$, or $R_6$ and $R_7$, taken together with the atoms it is attached to, is a substituent pair forming a fused ring system according to Formula 1c:

Formula 1c

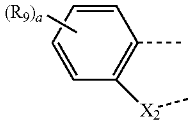

where the dashed lines represent the bonds of the substituent pair connecting to Formula 1a or 1b;

$R_9$ is halo, —CN, alkoxy, alkyl, aryl, heteroaryl, amino, alkylamino, dialkylamino, alkanecarboxamido, alkanesulfonamido, aminocarbonyl, N-alkylaminocarbonyl, N,N-dialkylaminocarbonyl, N,N,N-trialkylammoniumalkyl, aminosufonyl, N-alkylaminosulfonyl, N,N-dialkylaminosulfonyl, phosphonyl, sulfonate, carboxylate, azide, nitro, arylazo, or $(R)_p$—$(L)_q$—;

a is 0, 1, 2, 3, or 4;

$X_2$ is $CR_{11}R_{12}$, where each $R_{11}$ and $R_{12}$ is substituted or unsubstituted alkyl, $(R)_p$—$(L)_q$—, or $R_{11}$ and $R_{12}$ taken together form a 3-8 membered ring, optionally substituted by $(R)_p$—$(L)_q$—;

Y is a bridge unit that permits electron delocalization optionally comprising $(R)_p$—$(L)_q$—;

Q is optionally substituted aryl or heteroaryl;

$R_8$ is H, substituted or unsubstituted alkyl, substituted or unsubstituted aryl, substituted or unsubstituted heteroaryl, or $(R)_p$—$(L)_q$—; or $R_8$ taken together with $R_7$ forms a saturated or unsaturated 5- or 6-membered ring, optionally substituted; or $R_8$, taken together with a substituent on the moiety Y, forms a 5- or 6-membered saturated or unsaturated ring; or $R_8$, taken together with a substituent on the moiety Q, forms a macrocycle;

W is a counter ion;

c is an integer indicating the number of W such that the overall charge of Formula 1 is zero;

each R of each $(R)_p$—$(L)_q$— substituent is independently i) a reactive group capable of forming a covalent bond upon reacting with a reaction substrate; ii) a water-soluble group; or iii) a biopolymer;

each L of each $R)_p$—$(L)_q$— substituent is independently a linking moiety formed of one or more chemical bonds and containing about 1-100 atoms;

each p of each $R)_p$—$(L)_q$— is independently an integer of about 1 to about 20;

each q of each $R)_p$—$(L)_q$— is independently an integer of 0 to about 20; and the compound of Formula 1a or 1b comprises at least one substituent which is $R)_p$—$(L)_q$—.

2. The compound of claim 1, wherein at least one of $R_1$, $R_2$, $R_3$, $R_4$, $R_5$, $R_6$, $R_7$, $R_8$, $R_9$, $R_{10}$, $R_{11}$ and $R_{12}$ is $(R)_p$—$(L)_q$—.

3. The compound of claim 1, wherein $R)_p$—$(L)_q$— comprises an R which is a reactive group capable of forming a covalent bond upon reacting with a reaction substrate.

4. The compound of claim 1, wherein $R)_p$—$(L)_q$— comprises an R which is a water-soluble group.

5. The compound of claim 4, wherein the water-soluble group comprises a polyalkylene oxide group.

6. The compound of claim 1, wherein $(R)_p$—$(L)_q$— comprises an R which is a biopolymer.

7. The compound of claim 6, wherein the biopolymer is a protein, nucleic acid, lipid, or microparticle.

8. The compound of claim 7, wherein the biopolymer is a protein.

9. The compound of claim 8, wherein the protein is a monoclonal or polyclonal antibody.

10. The compound of claim 1, wherein the compound comprises a first $(R)_p$—$(L)_q$—where R is a reactive group capable of forming a covalent bond upon reacting with a reaction substrate, and a second $(R)_p$—$(L)_q$—where R is a water-soluble group.

11. The compound of claim 1, wherein Y is a methine or polymethine unit.

12. The compound of claim 11, wherein Y is a tri-, penta-or heptamethine unit.

13. The compound of claim 1, wherein Y is a cyclic group.

14. The compound of claim 13, wherein Y is a heterocyclic group.

15. The compound of claim 13, wherein Y is a 4, 5, or 6-membered ring.

16. The compound of claim 1, wherein Y comprises a $(R)_p$—$(L)_q$—.

17. The compound of claim 1, wherein Y is optionally substituted.

18. The compound of claim 17, wherein Y is substituted with alkyl, alkoxy, alkylthio, aryl, aryloxy, arylthio, alkylamino, N-acylated alkylamino, or halogen.

19. The compound of claim 1, wherein Y is:

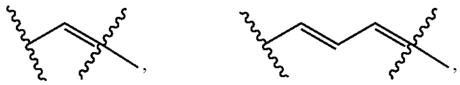
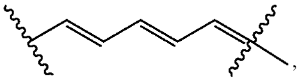
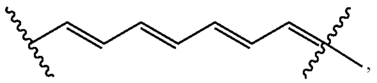
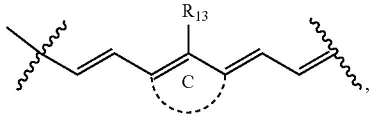
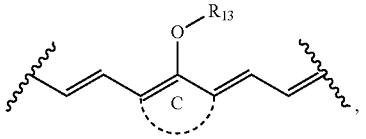
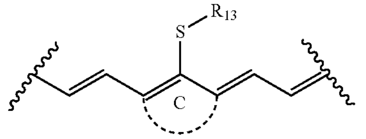
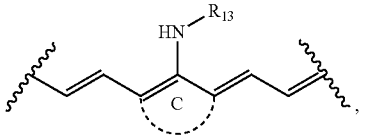
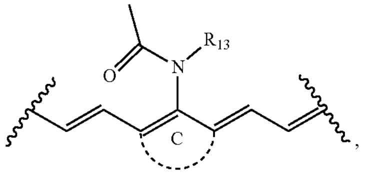
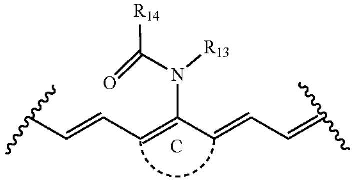

or

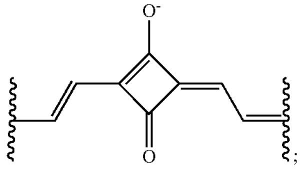

wherein C is a five-or six-membered cyclic group; $R_{13}$ is H, alkyl, aryl, heteroaryl, or $(R)_p$—$(L)_q$—; and $R_{14}$ is alkyl, aryl, heteroaryl, or $(R)_p$—$(L)_q$—.

20. The compound of claim 1, wherein Q is:

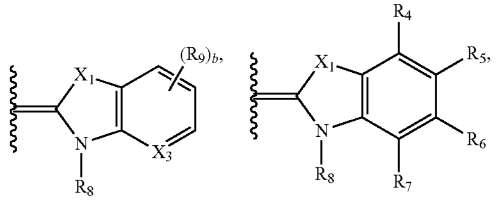
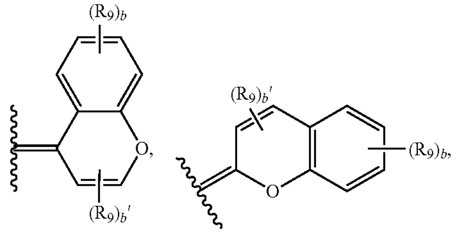
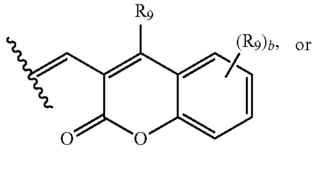

or

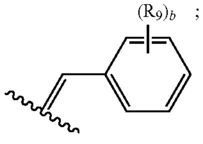

$X_3$ is

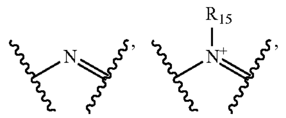

or

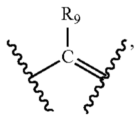

where $R_{15}$ is H, alkyl or $(R)_p$—$(L)_q$—;

b is 0, 1, 2, 3, 4 or 5 structurally permissible for each of the rings; and b' is 0, 1 or 2.

21. The compound of claim 20, wherein Q is

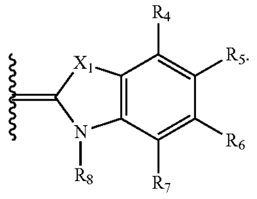

22. The compound of claim 21, wherein Q is

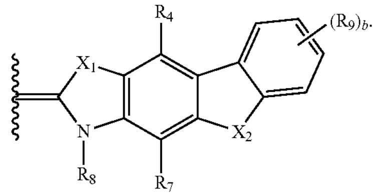

23. The compound of claim 1, wherein each a is independently 0 or 1.

24. The compound of claim 1, comprising at least one $R_9$ which is sulfonate.

25. The compound of claim 1, wherein $X_1$ is $CR_2R_3$.

26. The compound of claim 1, where $R_8$ is alkyl, substituted with sulfonate.

27. The compound of claim 1, where $R_8$ is alkyl, substituted with $(R)_p$—$(L)_q$—.

28. The compound of claim 1, where R is a reactive group capable of forming a covalent bond upon reacting with a reaction substrate, p is 1, and q is 0.

29. The compound of claim 1 or 2, where $R_8$ is alkyl, substituted with amino.

30. The compound of claim 1, where $R_8$, taken together with a substituent on the moiety Q, forms a macrocycle.

31. The compound of claim 1 or 2, wherein $R_5$ and $R_6$ forms a fused ring system according to Formula 1a.

32. The compound of claim 1 or 2, wherein $R_{11}$ and $R_{12}$ are independently alkyl.

33. The compound of claim 1 or 2, wherein $R_{11}$ and $R_{12}$ are methyl.

34. The compound of claim 1 or 2, wherein $R_{11}$ and $R_{12}$ taken together form a 3-8 membered ring.

35. The compound of claim 1 or 2, wherein the compound has the Formula 2:

Formula 2

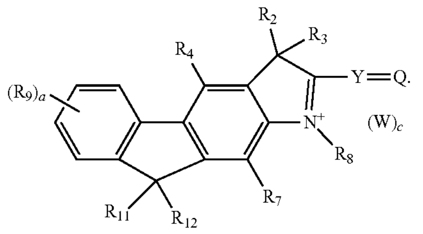

36. The compound of claim 35, comprising at least one $R_9$ which is sulfonate.

37. The compound of claim 35, wherein at least one of $R_2$, $R_3$, $R_8$, $R_9$, $R_{11}$ and $R_{12}$ is $(R)_p$—$(L)_q$—.

38. The compound of claim 37, wherein R is a reactive group capable of forming a covalent bond upon reacting with a reaction substrate.

39. The compound of claim 37, wherein R is a biopolymer.

40. The compound of claim 37, wherein R is a water-soluble group.

41. The compound of claim 35, wherein at least one of $R_2$, $R_3$, $R_8$, $R_9$, $R_{11}$ and $R_{12}$ is $(R)_p$—$(L)_q$—, where R is a water-soluble polymer, a reactive group capable of forming a covalent bond upon reacting with a reaction substrate, or a biologically active molecule, and further wherein at least one $R_9$ is sulfonate.

42. The compound of claim 35, wherein the compound has the formula:

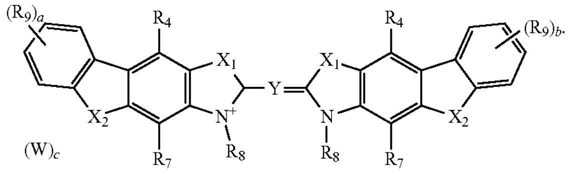

43. The compound of claim 1, wherein $R_8$ is not methyl.

44. The compound of claim 1, wherein the compound is selected from a group consisting of:

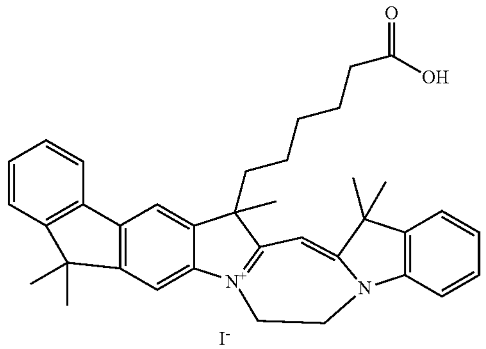

,

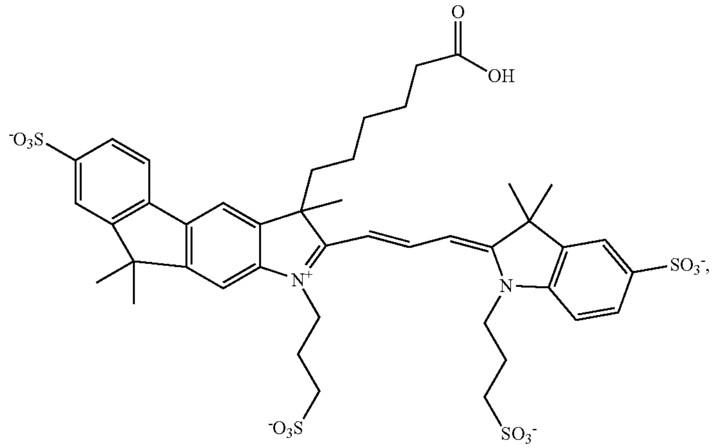

-continued
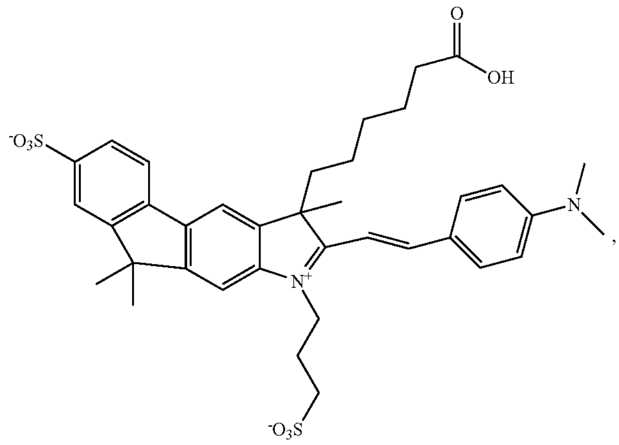
,
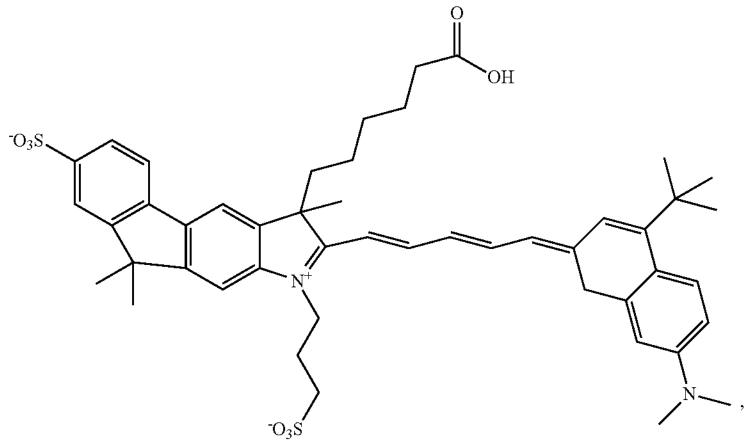
,
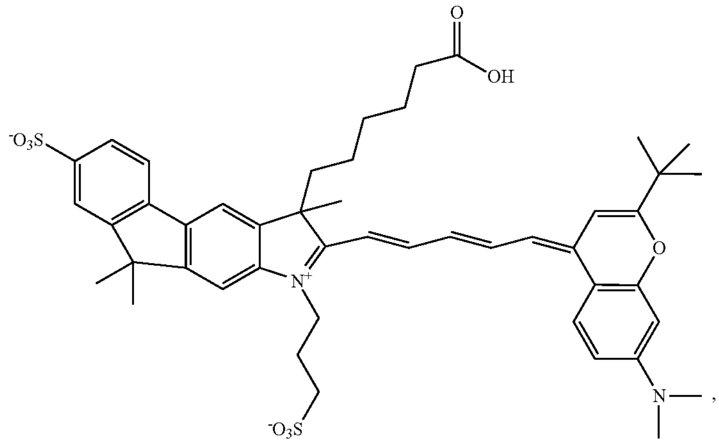
,

-continued
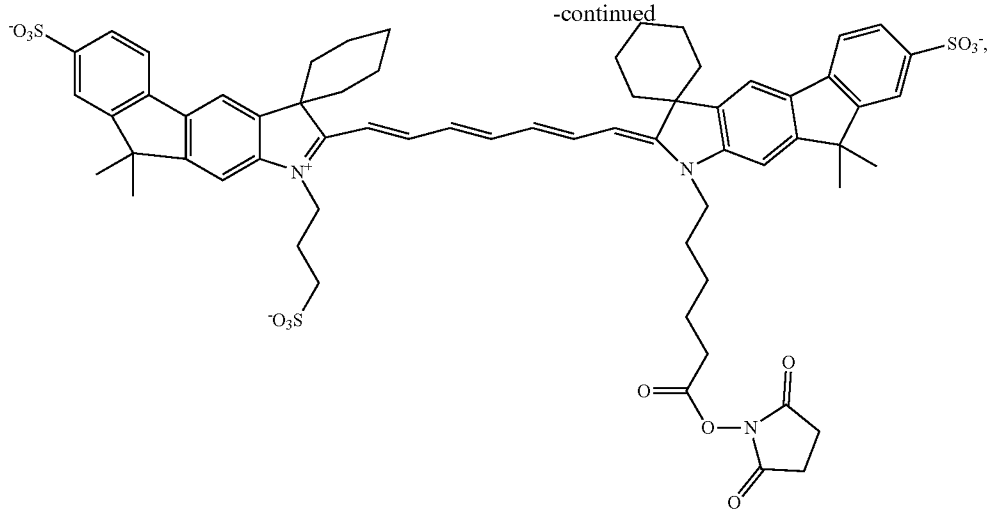
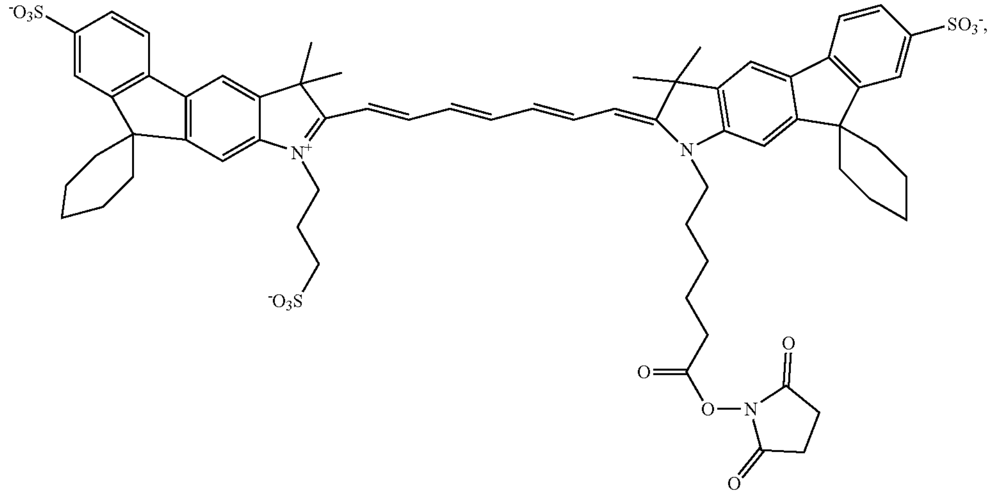
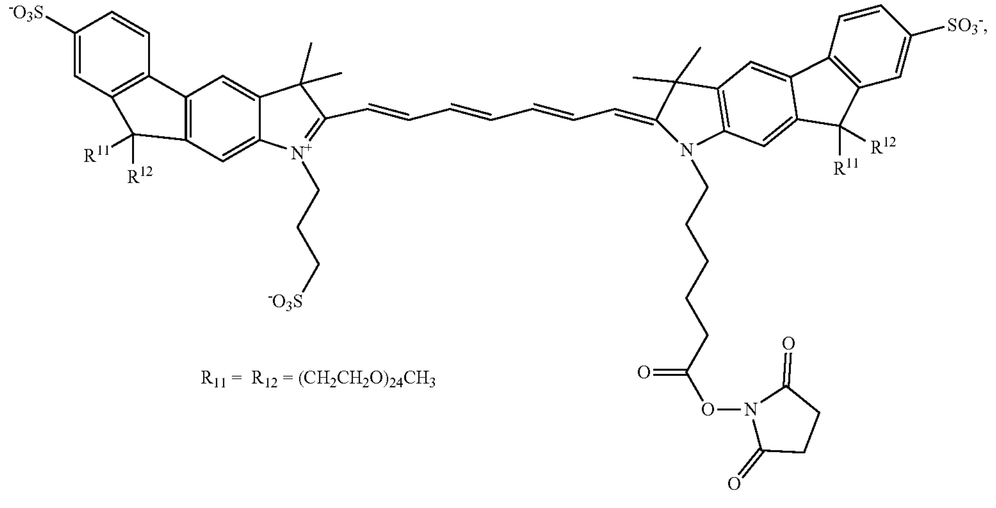
$R_{11} = R_{12} = (CH_2CH_2O)_{24}CH_3$ -continued
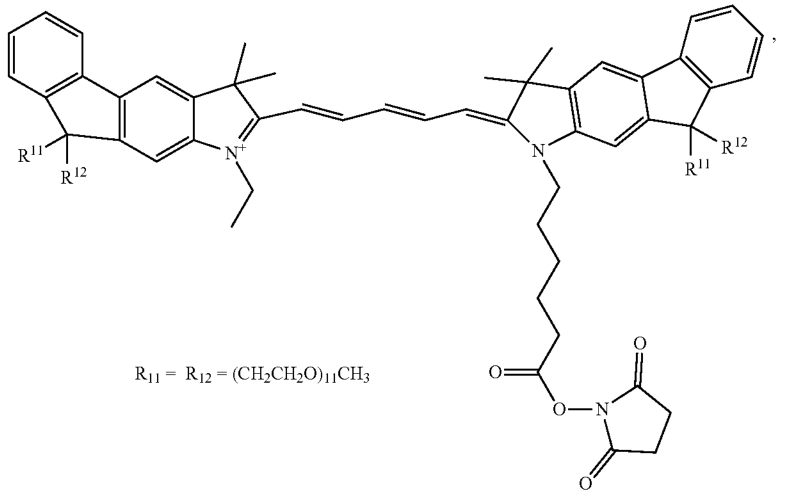
$R_{11} = R_{12} = (CH_2CH_2O)_{11}CH_3$
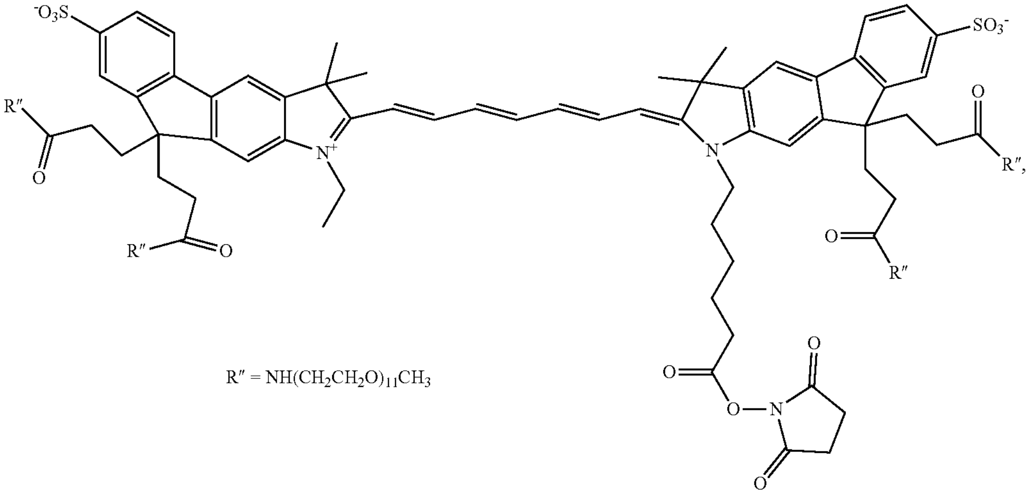
$R'' = NH(CH_2CH_2O)_{11}CH_3$
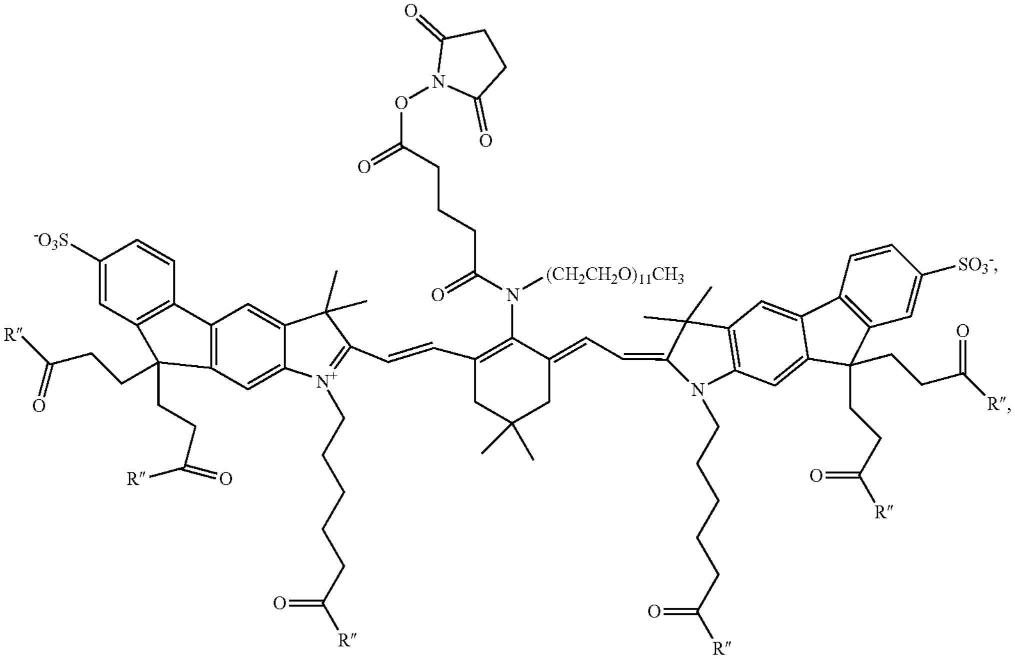
$R'' = NH(CH_2CH_2O)_6CH_3$ -continued
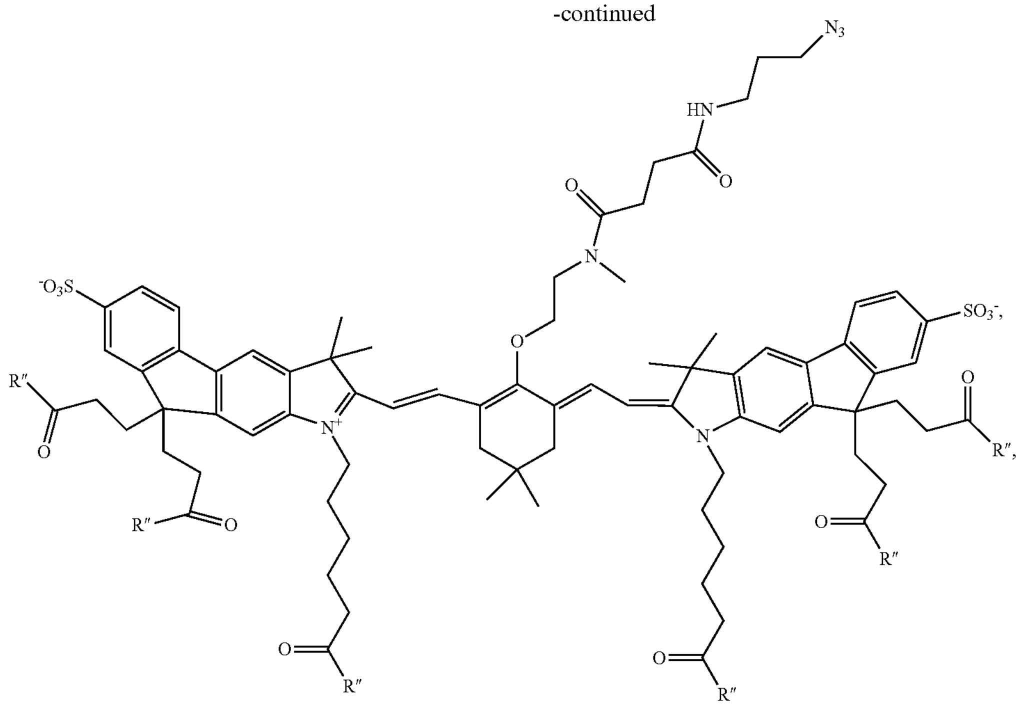
R″ = $NH(CH_2CH_2O)_4CH_3$
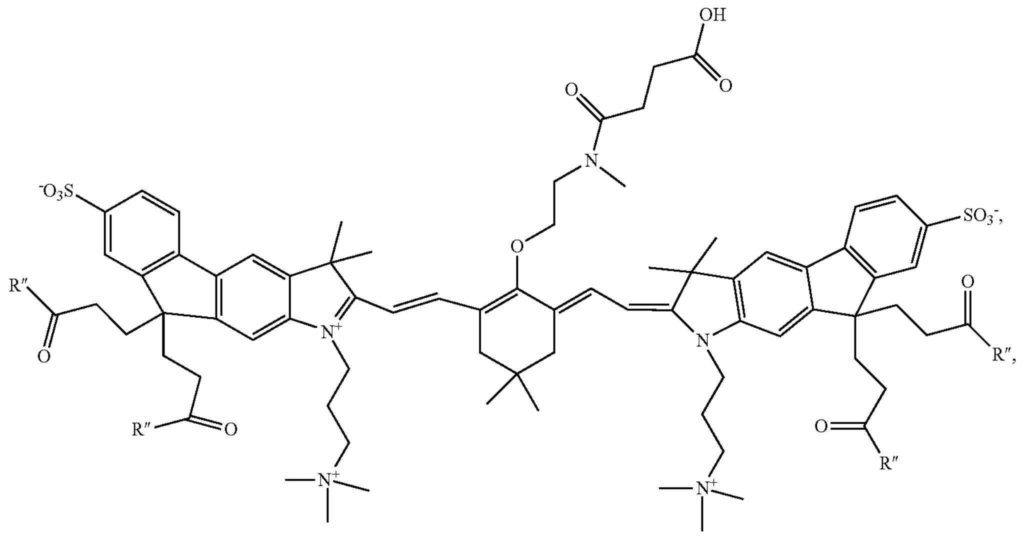
R″ = $NH(CH_2CH_2O)_{11}CH_3$
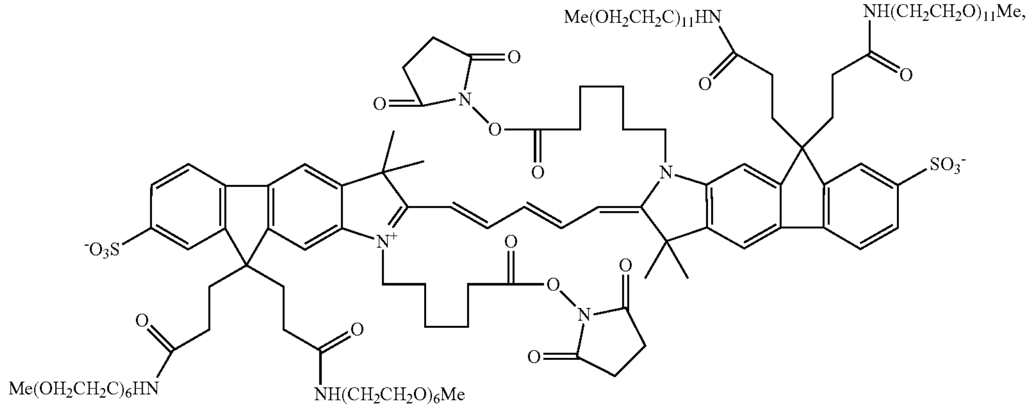

-continued
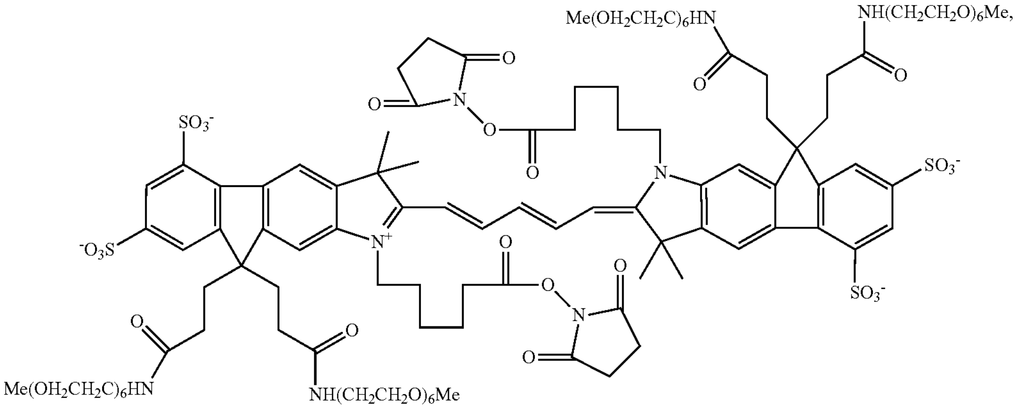
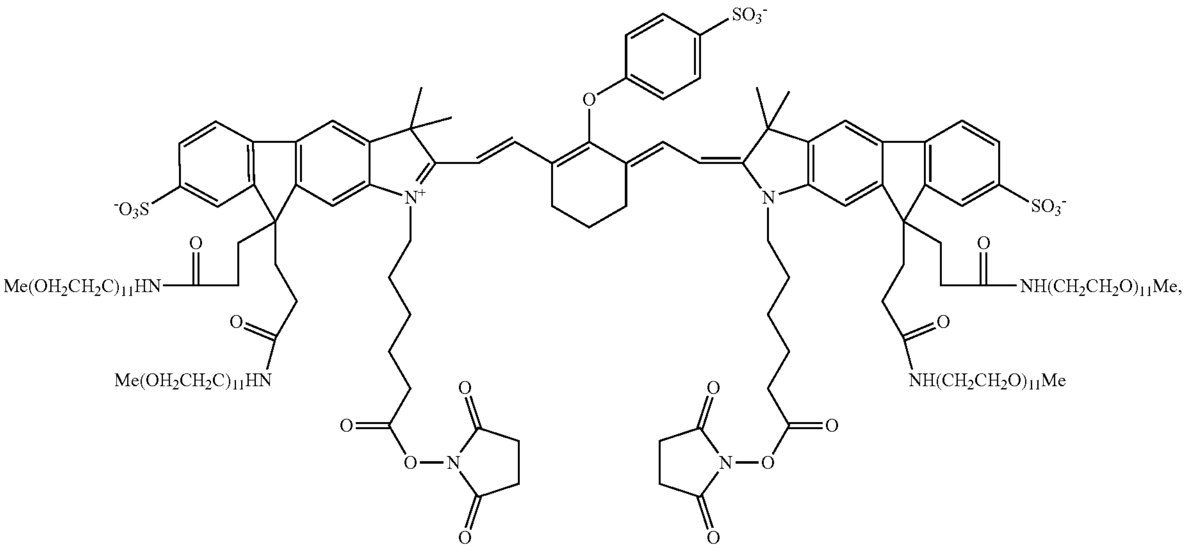
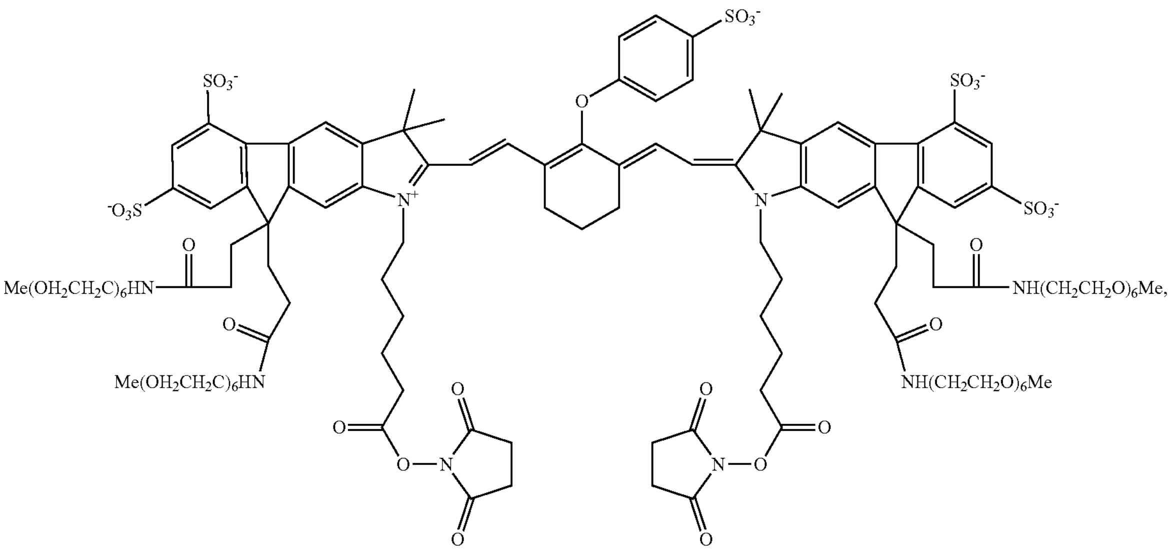

-continued
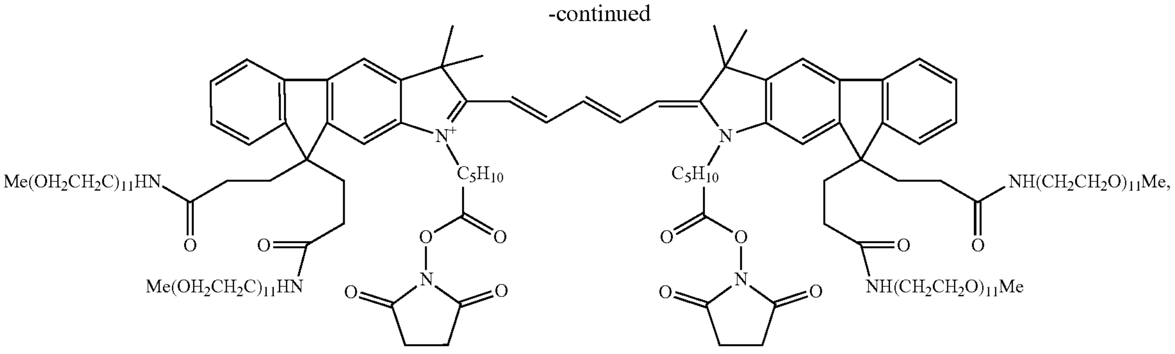
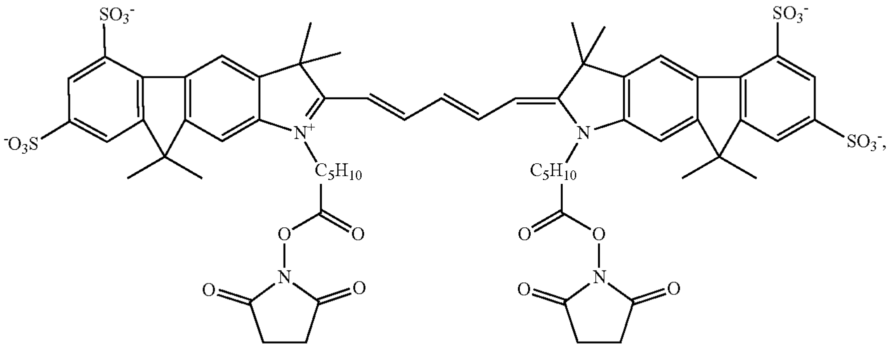
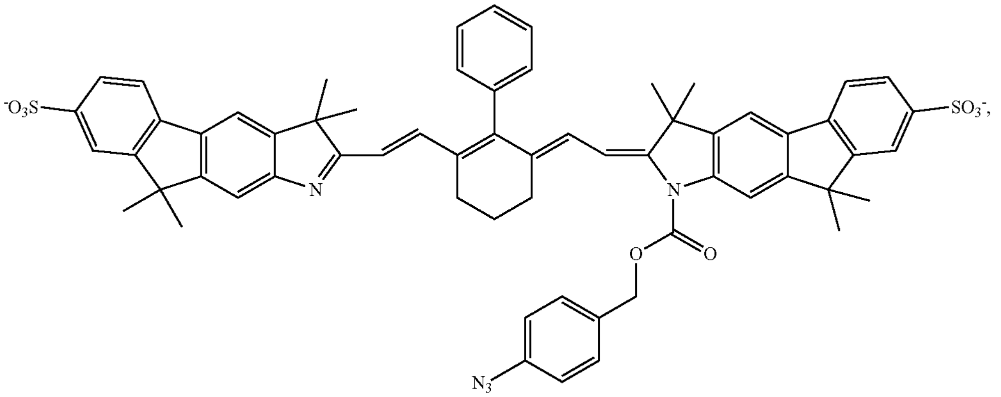
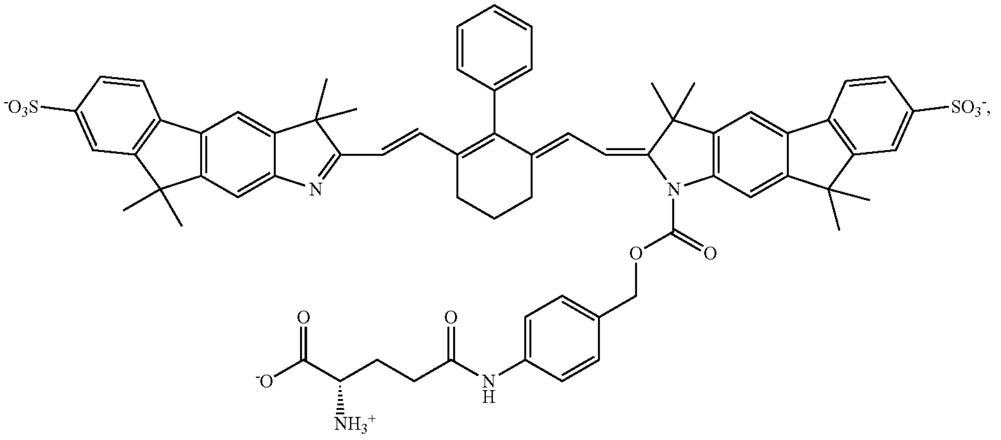

-continued

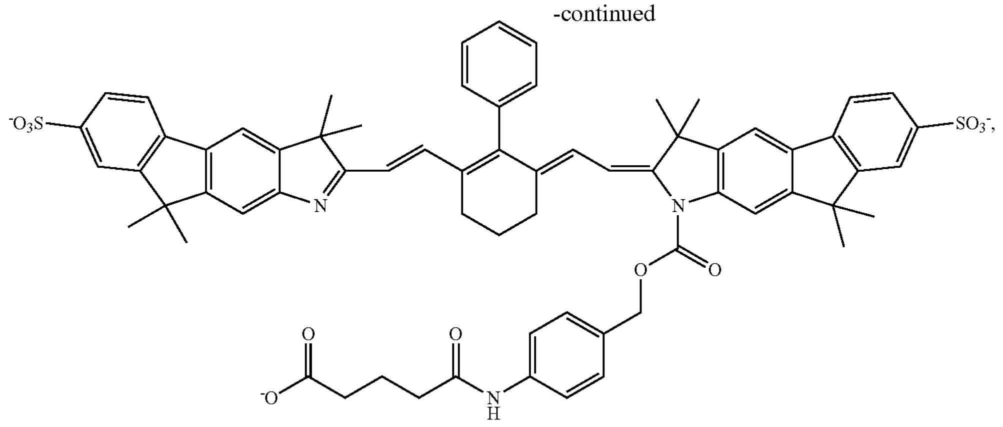

[[or]] and

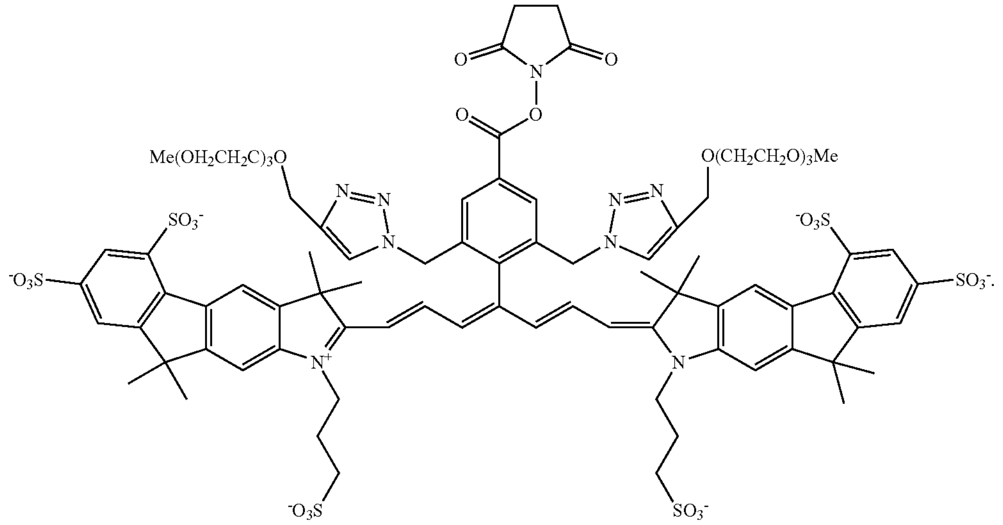

45. The compound of claim 1, wherein the compound has an absorption maximum equal to or greater than about 660 nm.

46. The compound of claim 1, wherein the compound has an absorption maximum of between about 660 and about 1250 nm.

47. A compound of Formula 3a or 3b:

wherein:

Formula 3a

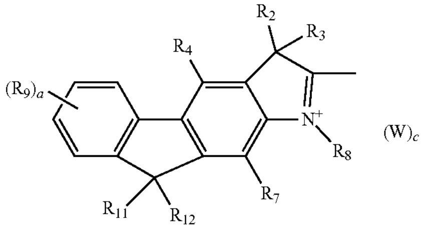

-continued

Formula 3b

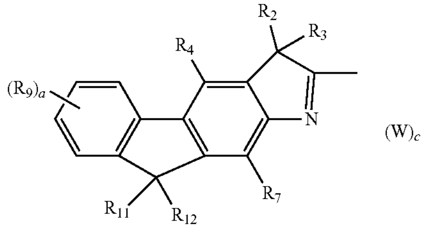

$R_2$ and $R_3$ are independently substituted or unsubstituted alkyl, $(R)_p$—$(L)_q$—, or $R_2$ and $R_3$ taken together form a 3-8 membered ring optionally substituted by $(R)_p$—$(L)_q$—;

$R_4$, and $R_7$ are independently hydrogen, halo, —CN, alkoxy, alkyl, aryl, heteroaryl, amino, alkylamino, dialkylamino, alkanecarboxamido, alkanesulfonamido, aminocarbonyl, N-alkylaminocarbonyl, N,N-dialkylaminocarbonyl, N,N,N-trialkylammoniumalkyl, aminosufonyl, N-alkylaminosulfonyl, N,N-dialkylaminosulfonyl, phosphonyl, carboxylate, azide, nitro, arylazo, or $(R)_p$—$(L)_q$—;

$R_9$ is halo, —CN, alkoxy, alkyl, aryl, heteroaryl, amino, alkylamino, dialkylamino, alkanecarboxamido, alkanesulfonamido, aminocarbonyl, N-alkylaminocarbonyl, N,N-dialkylaminocarbonyl, N,N,N-trialkylammoniumalkyl, aminosufonyl, N-alkylaminosulfonyl, N,N-dialkylaminosulfonyl, phosphonyl, sulfonate, carboxylate, azide, nitro, arylazo, or $(R)_p$—$(L)_q$—;

a is 0, 1, 2, 3, or 4;

$R_8$ is H, substituted or unsubstituted alkyl, substituted or unsubstituted aryl, substituted or unsubstituted heteroaryl, or $(R)_p$—$(L)_q$—; or $R_8$ taken together with $R_7$ forms a saturated or unsaturated 5-or 6-membered ring, optionally substituted;

W is a counter ion;

c is an integer indicating the number of W such that the overall charge of Formula 1 is zero;

each R of each $(R)_p$—$(L)_q$— substituent is independently i) a reactive group capable of forming a covalent bond upon reacting with a reaction substrate; ii) a water-soluble group; or iii) a biopolymer;

each L of each $(R)_p$—$(L)_q$— substituent is independently a linking moiety formed of one or more chemical bonds and containing about 1-100 atoms;

each p of each $(R)_p$—$(L)_q$— is independently an integer of about 1 to about 20;

each q of each $(R)_p$—$(L)_q$— is independently an integer of 0 to about 20; and the compound of Formula 3a or 3b comprises at least one substituent which is $(R)_p$—$(L)_q$—.

* * * * *